US011521731B2

(12) United States Patent
Chen et al.

(10) Patent No.: US 11,521,731 B2
(45) Date of Patent: *Dec. 6, 2022

(54) CHARGING DEVICE FOR A PHYSIOLOGICAL SIGNAL TRANSMITTER

(71) Applicant: BIONIME CORPORATION, Taichung (TW)

(72) Inventors: Chieh-Hsing Chen, Taichung (TW); Chun-Mu Huang, Taichung (TW)

(73) Assignee: BIONIME CORPORATION, Taichung (TW)

( * ) Notice: Subject to any disclaimer, the term of this patent is extended or adjusted under 35 U.S.C. 154(b) by 0 days.

This patent is subject to a terminal disclaimer.

(21) Appl. No.: 17/144,266

(22) Filed: Jan. 8, 2021

(65) Prior Publication Data

US 2021/0217521 A1 Jul. 15, 2021

Related U.S. Application Data

(60) Provisional application No. 62/960,855, filed on Jan. 14, 2020.

(51) Int. Cl.
*G16H 20/17* (2018.01)
*A61M 5/172* (2006.01)
(Continued)

(52) U.S. Cl.
CPC .......... *G16H 20/17* (2018.01); *A61B 5/0004* (2013.01); *A61B 5/0015* (2013.01);
(Continued)

(58) Field of Classification Search
CPC ...... G16H 20/17; G16H 40/67; A61B 5/0004; A61B 5/0015; A61B 5/0031; A61B 5/073;
(Continued)

(56) References Cited

U.S. PATENT DOCUMENTS

2007/0276293 A1* 11/2007 Gertner ................ A61F 5/0083
600/593
2017/0266454 A1* 9/2017 Amir .................... A61N 1/0563
(Continued)

*Primary Examiner* — Kerri L McNally
(74) *Attorney, Agent, or Firm* — Volpe Koenig

(57) ABSTRACT

A charging device for a physiological signal transmitter is disclosed, wherein the physiological signal transmitter is to receive and externally transmit a physiological signal from a subcutaneous tissue of a living body, and has a first electrical connecting port. The charging device comprises a transmitter placing seat, a charging module and a locking module. The transmitter placing seat includes a bearing surface, and a first opening. The bearing surface disposes thereon the physiological signal transmitter; and the first opening aligns therewith the first electrical connecting port of the physiological signal transmitter. The charging module includes a second electrical connecting port, a third electrical connecting port and a circuit assembly. The second electrical connecting port is disposed in the first opening and moveable between a first position and a second position. The third electrical connecting port is for connecting thereto a power source. The circuit assembly is for performing charging and charging control on the physiological signal transmitter, and the circuit assembly is electrically connected to the second electrical connecting port and the third electrical connecting port. The locking module is extendable or retractable on the bearing surface for releasably positioning the physiological signal transmitter, wherein the charging module is driven to move the second electrical connecting port from the first position to the second position to be electrically connected to the first electrical connecting port, and the locking module is driven to protrude out of the bearing surface to fix the transmitter.

18 Claims, 46 Drawing Sheets

(51) Int. Cl.

| | |
|---|---|
| *A61B 5/00* | (2006.01) |
| *A61B 5/07* | (2006.01) |
| *H02J 7/00* | (2006.01) |
| *G16H 40/67* | (2018.01) |
| *A61B 5/145* | (2006.01) |
| *H01R 13/631* | (2006.01) |
| *H01R 13/642* | (2006.01) |
| *H01R 13/66* | (2006.01) |
| *H01R 33/945* | (2006.01) |
| *H01R 43/26* | (2006.01) |
| *H01R 13/639* | (2006.01) |

(52) U.S. Cl.
CPC ............ *A61B 5/0031* (2013.01); *A61B 5/073* (2013.01); *A61B 5/14532* (2013.01); *A61B 5/6801* (2013.01); *A61B 5/72* (2013.01); *A61M 5/1723* (2013.01); *G16H 40/67* (2018.01); *H01R 13/631* (2013.01); *H01R 13/639* (2013.01); *H01R 13/642* (2013.01); *H01R 13/665* (2013.01); *H01R 13/6675* (2013.01); *H01R 33/945* (2013.01); *H01R 43/26* (2013.01); *H02J 7/0031* (2013.01); *H02J 7/0045* (2013.01); *A61B 5/14503* (2013.01); *A61B 2560/0456* (2013.01); *A61B 2562/166* (2013.01); *A61B 2562/18* (2013.01); *A61B 2562/227* (2013.01); *A61M 2205/35* (2013.01); *A61M 2205/8237* (2013.01); *A61M 2205/8262* (2013.01); *H01R 2201/12* (2013.01)

(58) Field of Classification Search
CPC ..... A61B 5/14532; A61B 5/6801; A61B 5/72; A61M 5/1723; H01R 13/631; H01R 13/639; H01R 13/642; H01R 13/665; H01R 13/6675; H01R 33/945; H01R 43/26; H02J 7/0031; H02J 7/0045
USPC ..................................................... 340/539.12
See application file for complete search history.

(56) References Cited

U.S. PATENT DOCUMENTS

| | | | | |
|---|---|---|---|---|
| 2017/0358942 | A1* | 12/2017 | Pugh | H02J 50/80 |
| 2018/0177579 | A1* | 6/2018 | Sayet | A61F 2/004 |
| 2019/0298184 | A1* | 10/2019 | Jain | A61B 5/02416 |

* cited by examiner

CHARGING DEVICE FOR A PHYSIOLOGICAL SIGNAL TRANSMITTER

CROSS-REFERENCE TO RELATED APPLICATION AND CLAIM OF PRIORITY

The application claims the benefit of the U.S. Provisional Application No. 62/960,855, filed on Jan. 14, 2020, at the USPTO, the disclosures of which are incorporated herein in their entirety by reference.

FIELD OF THE INVENTION

The present invention relates to a charging device, and more particularly to a charging device applied to a transmitter. The transmitter is a reusable electronic device for collecting physiological signals of the living body and transmitting them out in a continuous physiological signal measuring device, and the charging device is used to charge the transmitter.

BACKGROUND OF THE INVENTION

With the recent advancements of current technology and changing lifestyles, some tests which had to be tested in the hospital in the past have now changed to home measurement. In particular, the change in lifestyles has led to an increase in patients with chronic diseases, which has accelerated the development of this industry. The measurement of blood glucose is a testing item, and the measurement of blood glucose concentration in the blood is an important step for effectively monitoring and treating diabetes. For the past two decades, the continuous glucose monitoring (CGM) system has developed rapidly. In addition, because the CGM system must be worn by the user for a long time, the miniaturization of the device has become an inevitable trend. Generally, the basic structure of the CGM system mostly includes a sensor, a transmitter and a sensor inserter. The sensor is used to measure the physiological signal corresponding to the glucose concentration in the human body. The transmitter is usually assembled with a patch base with a transmitter installed to receive and transmit the physiological signal. The sensor inserter is usually a mechanical device for attaching the patch base with the sensor installed to the skin surface of the living body, and enabling a part of the transmitter to be implanted under the skin of the user. The transmitter is a relatively expensive electronic element and usually contains the processing element for processing the signal from the transmitter and transmitting the processed signal in a wireless way. Therefore, ideally if the transmitter is a reusable element, the purposes of environmental protection and cost reduction can be achieved. Hence, in order to allow the transmitter to be reused, it is necessary to supplement the power for the transmitter. In order to avoid the pollution of the waste battery which may be caused by using the ordinary battery, the battery in the transmitter is mostly a rechargeable battery. Thus, in this technical field, a charger used in conjunction with the transmitter is required.

In order to overcome the drawbacks in the prior art, a charging device for a physiological signal transmitter and a charging method for the same is disclosed. The particular design in the present invention not only solves the problems described above, but also it is easy to implement. Thus, the present invention has utility for the industry.

SUMMARY OF THE INVENTION

In order to achieve the purpose of charging the transmitter, the present invention provides a charger to charge the reusable transmitter. When in use, the transmitter is disassembled from the patch base, and inserted into the charging device for charging.

In accordance with one aspect of the present invention, a charging device for a physiological signal transmitter is provided, wherein the physiological signal transmitter is to receive and transmit a physiological signal from a subcutaneous tissue of a living body, and has a first electrical connecting port connecting to the charging device for charging. The charging device comprises a transmitter placing seat, a charging module and a control module. The transmitter placing seat includes a bearing surface and a first opening. The bearing surface disposes thereon the physiological signal transmitter, and the first opening aligns therewith the first electrical connecting port of the physiological signal transmitter. The charging module includes a second electrical connecting port, a third electrical connecting port and a circuit assembly. The second electrical connecting port is disposed in the first opening and moveable between a first position and a second position. The third electrical connecting port is connectible to a power source. The circuit assembly controls a charging of the physiological signal transmitter, wherein the circuit assembly is electrically connected to the first electrical connecting port via the second electrical connecting port, and inputs therefrom a power from the power source by connecting to the third electrical connecting port. The control module controls an operation between the charging device and the physiological signal transmitter in a safe state and includes an operating portion and a locking portion. The operating portion is mechanically coupled with the second electrical connecting port, the operating portion is controlled to drive the second electrical connecting port to move between the first position and the second position, and is electrically separated or connected with the first electrical connecting port. The locking portion is mechanically coupled with the operating portion, and controlling the operating portion for driving the locking portion to protrude or retract along the bearing surface so as to determine whether the physiological signal transmitter is at a predetermined position to prohibit or allow an access of the physiological signal transmitter, wherein when the physiological signal transmitter is placed on the bearing surface, the operating portion is controlled to drive the second electrical connecting port to move from the first position to the second position to be electrically connected to the first electrical connecting port, and the locking portion is driven to protrude out of the bearing surface to position the physiological signal transmitter for locking the physiological signal transmitter from being removed, so as to prevent the first electrical connecting port and the second electrical connecting port from being damaged while electrically connecting because the physiological signal transmitter is taken out or placed, so as to achieve the safe state; when the operating portion drives the second electrical connecting port to move from the second position to the first position to separate the first electrical connecting port from the second electrical connecting port, and the operating portion drives the locking portion retracts from the bearing surface for unlocking the physiological signal transmitter, so as to allow the first connection port and the second connection port to be separated before the removal of the physiological signal transmitter to achieve the safety state.

In accordance with one aspect of the present invention, a charging device for a physiological signal transmitter is provided, wherein the physiological signal transmitter is to receive and transmit a physiological signal from a subcutaneous tissue of a living body, and has a first electrical connecting port. The charging device comprises a transmitter placing seat, a charging module and a control module. The transmitter placing seat includes a bearing surface and a first opening. The bearing surface disposes thereon the physiological signal transmitter; and the first opening aligns therewith the first electrical connecting port; The charging module includes a second electrical connecting port, a third electrical connecting port and a circuit assembly. The second electrical connecting port is disposed in the first opening and moveable between a first position and a second position. The third electrical connecting port is connectible to a power source. The circuit assembly is for performing charging and charging control on the physiological signal transmitter, and the circuit assembly is electrically connected to the second electrical connecting port and the third electrical connecting port. The control module for controlling a safety of electrical connection between the physiological signal transmitter and the charging module, includes an operating portion and a locking portion. The operating portion is coupled with the charging module for driving the second electrical connecting port to move and electrically connect with the first electrical connecting port. The locking portion is extendable or retractable on the bearing surface for releasably positioning the physiological signal transmitter, wherein, when the physiological signal transmitter is placed on the bearing surface, the operating portion drives the second electrical connecting port to move from the first position to the second position to be electrically connected to the first electrical connecting port, and the locking portion is driven to protrude out of the bearing surface to locate the physiological signal transmitter.

In accordance with one aspect of the present invention, a charging device for a physiological signal transmitter is disclosed, wherein the physiological signal transmitter is to receive and externally transmit a physiological signal from a subcutaneous tissue of a living body, and has a first electrical connecting port. The charging device comprises a transmitter placing seat, a charging module and a locking module. The transmitter placing seat includes a bearing surface, and a first opening. The bearing surface disposes thereon the physiological signal transmitter; and the first opening aligns therewith the first electrical connecting port of the physiological signal transmitter. The charging module includes a second electrical connecting port, a third electrical connecting port and a circuit assembly. The second electrical connecting port is disposed in the first opening and moveable between a first position and a second position. The third electrical connecting port is for connecting thereto a power source. The circuit assembly is for performing charging and charging control on the physiological signal transmitter, and the circuit assembly is electrically connected to the second electrical connecting port and the third electrical connecting port. The locking module is extendable or retractable on the bearing surface for releasably positioning the physiological signal transmitter, wherein the charging module is driven to move the second electrical connecting port from the first position to the second position to be electrically connected to the first electrical connecting port, and the locking module is driven to protrude out of the bearing surface to fix the transmitter.

The effects of the present invention are that the present invention can provide power to the transmitter, and has a foolproof efficacy. This can prevent the damage to the charger or the transmitter resulting from the wrong transmitter disposing direction by the user. Because the direction of the electrical connection between the transmitter and the charger has an angle with the disposing direction of the transmitter on the charger, the present invention also has an ingenious mechanism to enable the charging connector to move so as to be electrically connected with the charger for charging. In addition, the present invention also has a safety mechanism, which can prevent the improper impact caused by the movement of the charging connector when the transmitter is not correctly placed. Furthermore, in order to prevent the transmitter from shaking or even falling out on the charger, the charger also has a positioning mechanism, which can block the transmitter so that it is not easily detached from the charger.

The above objectives and advantages of the present invention will become more readily apparent to those ordinarily skilled in the art after reviewing the following detailed descriptions and accompanying drawings, in which:

DETAILED DESCRIPTION OF THE PREFERRED EMBODIMENTS

The present invention will now be described more specifically with reference to the following embodiments. It is to be noted that the following descriptions of preferred embodiments of this invention are presented herein for the purposes of illustration and description only; they are not intended to be exhaustive or to be limited to the precise form disclosed.

Figure 1A:
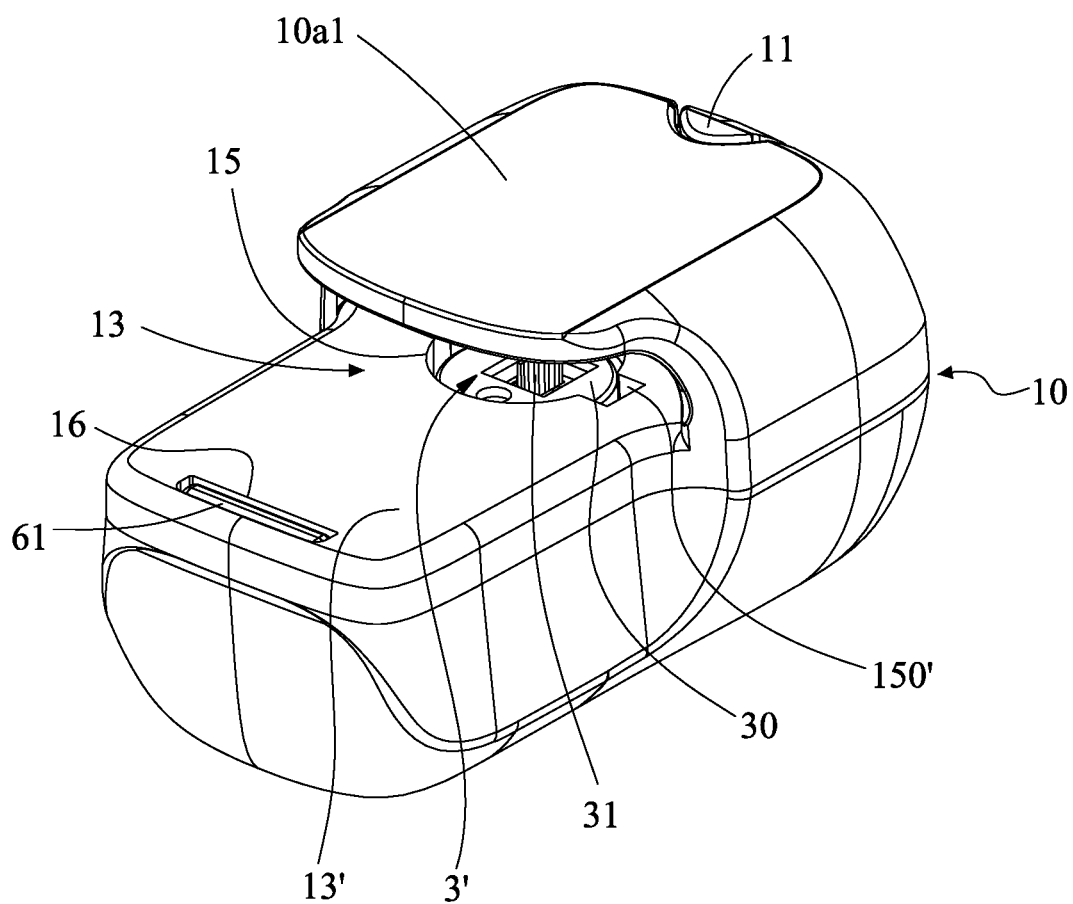
FIG. 1A is a three-dimensional view of the appearance of a charging device without the disposition of a transmitter according to an embodiment of the present invention.
Figure 1B:
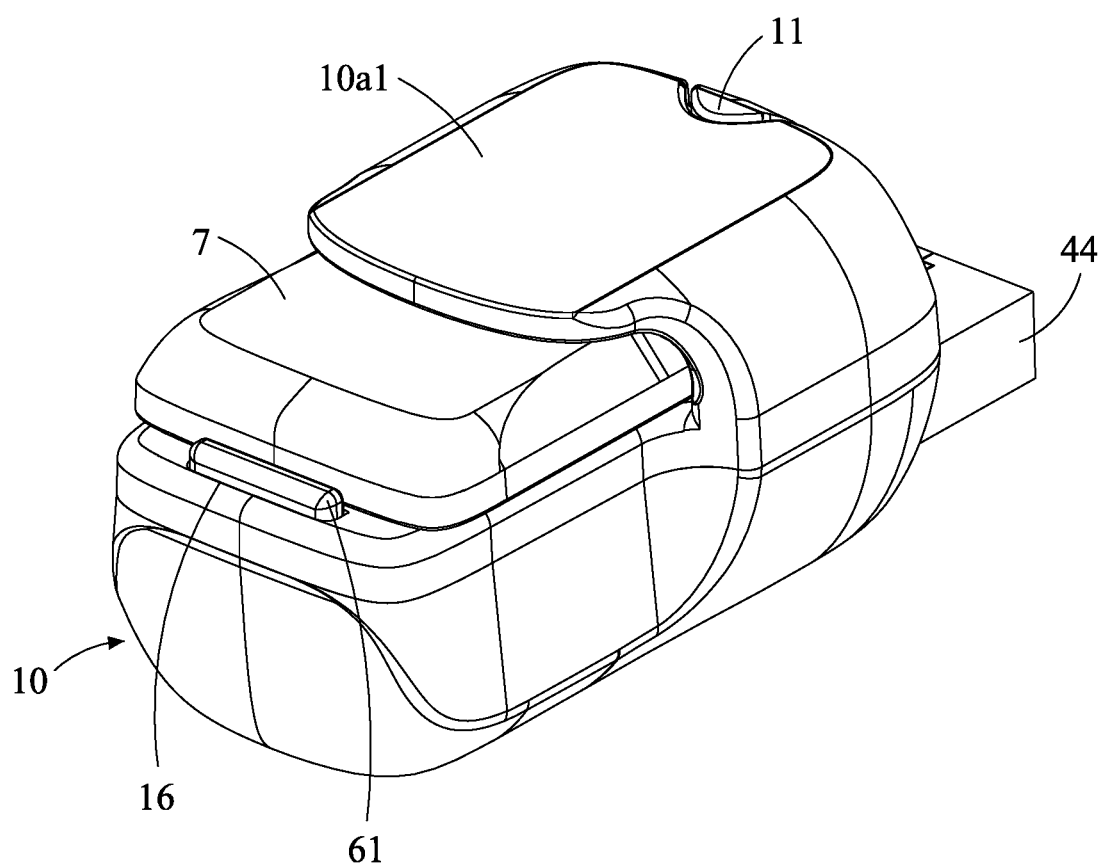
FIG. 1B is a three-dimensional view of the appearance of a charging device with the disposition of a transmitter according to an embodiment of the present invention.
Figure 1C:
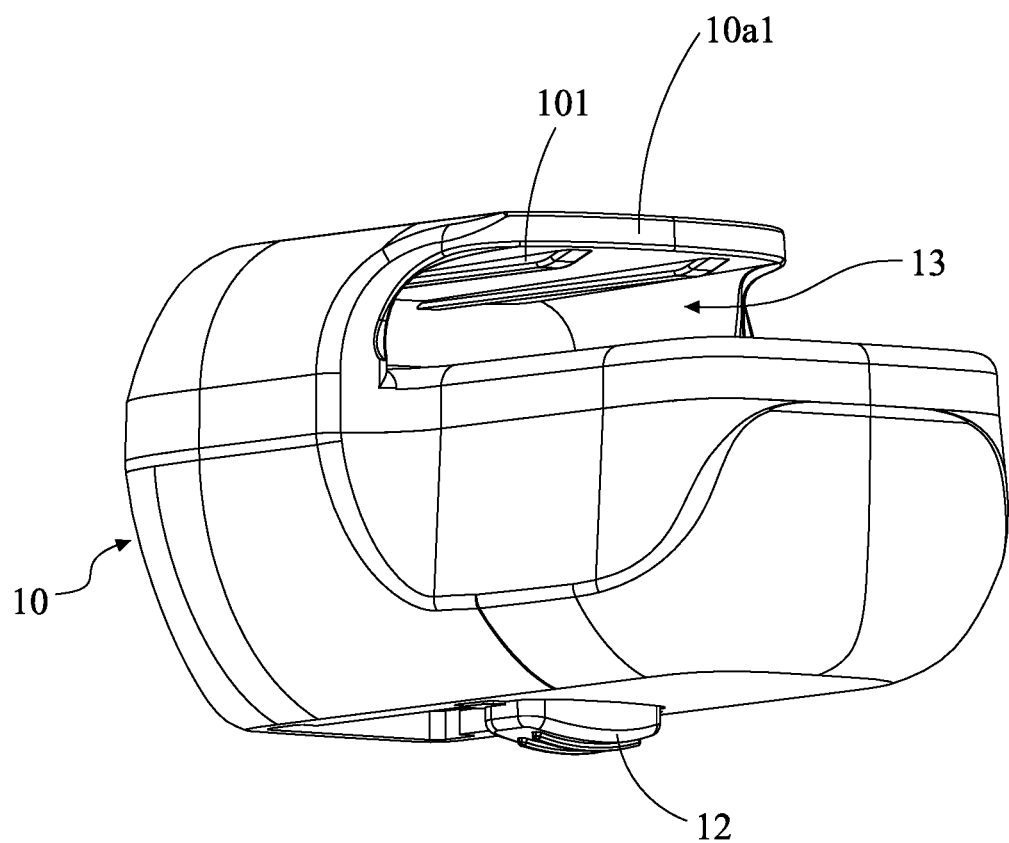
FIG. 1C shows the charging device of FIG. 1A from another angle.
Figure 1D:
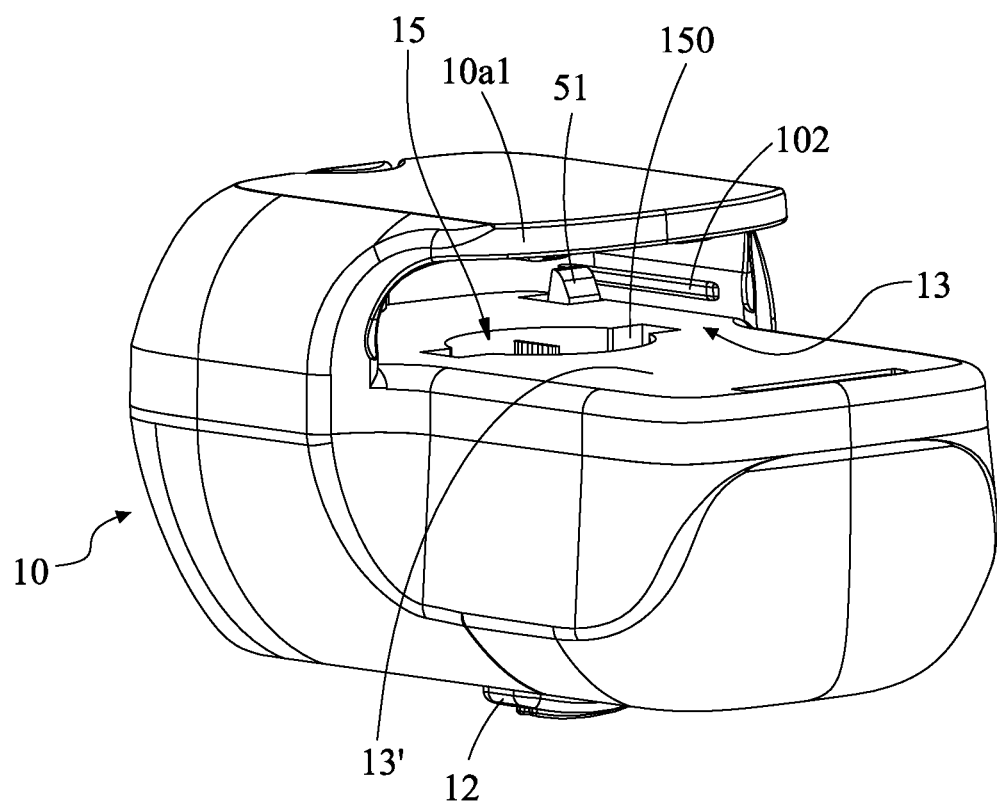
FIG. 1D shows the charging device of FIG. 1A from a further angle.

Please refer to FIGS. 1A-1G. FIGS. 1A-1D are presented at different angles to fully show the relative positions and connecting relationships among elements and structures. As shown in FIGS. 1A-1D, a charging device 1 has a main body 10, usually a shell-shaped object, for disposing and protecting the required elements and structures therein. The charging device 1 also has a placing portion 13 having a bearing surface 13' for placing the physiological signal transmitter 7 (hereinafter referred to as the transmitter 7). The placing portion 13 is similar to a slot or a pocket-like structure, and formed by a cover plate 10a1 with the bearing surface 13' for the transmitter 7 to be laterally inserted thereinto. In other embodiments, the placing portion 13 is also not limited to other configurations. In FIG. 1B, when the transmitter 7 is correctly placed in the placing portion 13, a baffle 61 protrudes from a baffle outlet 16 to position the transmitter 7 in the placing portion 13 to prevent the transmitter 7 from leaving the placing portion 13. At the same time, a plug 44 (or referred to as a third electrical connecting port) also protrudes out of the body 10. FIGS. 1A and 1D disclose that there is an opening 15 (or referred to as a lifting channel) in the placing portion 13 for a charging seat 30 of a second electrical connecting port 3' to lift therein; that is, a placing portion 13 is formed on the outside or top of the second electrical connecting port 3' or the charging pedestal 30 In addition, in order to avoid the abnormal movement of the charging seat 30, a guiding portion 150 is further disposed in the opening 15 (please see FIG. 5E) to prevent the charging seat 30 from shaking on all sides or rotating in the lifting process, and a sliding groove 150' is formed between the guiding portion 150. Moreover, a first conductive connector 31, usually in the form of a gold finger, is fixed on the charging seat 30 for being electrically connecting to the electrical connecting port 73 of the transmitter 7 of FIG. 3D. Furthermore, FIGS. 1C and 1D disclose that in the placing portion 13, upper restricting ribs 101 are disposed on the inner surface of the cover plate 10a1, and side restricting ribs 102 are disposed on the inner surfaces of the two side walls of the cover plate 10a1 to reduce the contact area between the charging device 1 and the transmitter 7 so as to reduce the frictional force when placing or removing the transmitter 7 in the charging device 1. Moreover, the restricting ribs 101, 102 also helps the transmitter 7 to be positioned on the charging seat 30, and prevents the transmitter 7 from shaking or being difficult to remove. Furthermore, when producing the upper housing 10a, the restricting ribs 101, 102 also help the upper housing 10a to be separated from the mold. The cover plate 10a1 is used to shield the opening 15, which is beneficial to the electrostatic protection, and can also prevent improper foreign objects from hitting the first conductive connector 31 and/or the charging seat 30. In another embodiment, the charging device 10 can also omit the cover plate 10a1, or can appropriately shield the front, the side, and the top of the transmitter 7 without the cover plate 10a1. In addition, the push-pull key 12 for controlling the operating module 4 (please refer to FIG. 2) protrudes out of the housing 10, and the user controls the action of the operating module 4 via the push-pull key 12.

Please refer to FIG. 1D, which discloses that when the transmitter 7 is not placed at a predetermined position, e.g. having not been placed or being not correctly placed in the placing portion 13, an actuating end 51 protrudes into the placing portion 13. The actuating end 51 belongs to a first locking module 5 (also referred to as a stopping module 5).

When the transmitter 7 is correctly placed in the placing portion 13, the actuating end 51 is pressed to move downward. The detailed operating principle will be described later (please refer to FIGS. 4C and 6C).

Figure 1E:
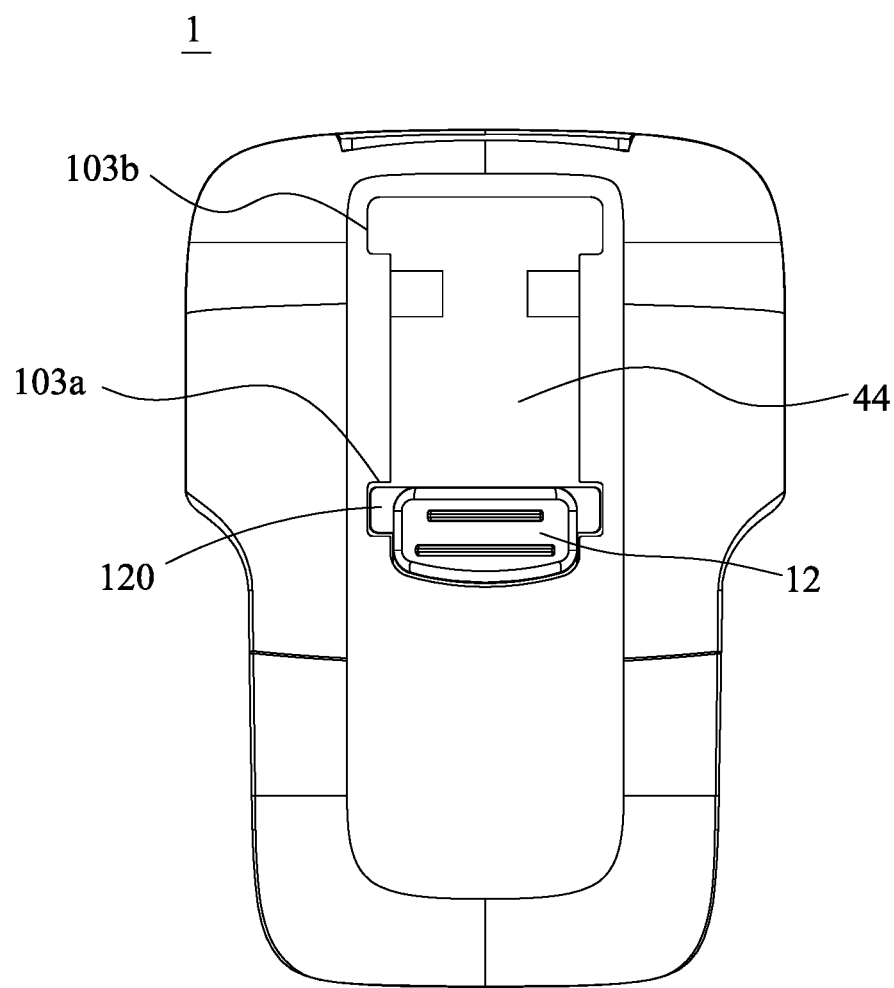
FIG. 1E is a bottom view of the charging device of FIG. 1A.

Please refer to FIG. 1E. The push-pull key 12 is disposed at the bottom of the housing 10, and further has a positioning block 120. A first positioning groove 103*a* and a second positioning groove 103*b* are correspondingly formed on the housing 10. The positioning block 120 of FIG. 1E is engaged with the first positioning groove 103*a* to maintain the push-pull key 12 in the first operating state. When the user presses the push-pull key 12 toward the inside of the housing 10, the positioning block 120 can be separated from the first positioning groove. Then, when the push-pull key 12 is pushed to the second positioning groove 103*b*, the positioning block 120 can be engaged with the second positioning groove 103*b* (please refer to FIG. 6G). Please refer to FIG. 1F, which discloses a rear (back part) view of the charging device 1. The restricting ribs 101 are disposed on the inner surfaces of the cover plate 10*a*1. Moreover, it also can be seen that a first matching portion 14 is protrudingly disposed at the deepest part of the placing portion 13. Please refer to FIG. 1G, which discloses that the width W2 of the placing portion 13 of the charging device 1 is less than or equal to the width W1 of the transmitter 7. When the user wants to take out the transmitter 7, he can conveniently hold and clamp the transmitter 7 from the left and right sides of the placing portion 13 without clamping the charging device 1 at the same time.

Figure 1F:
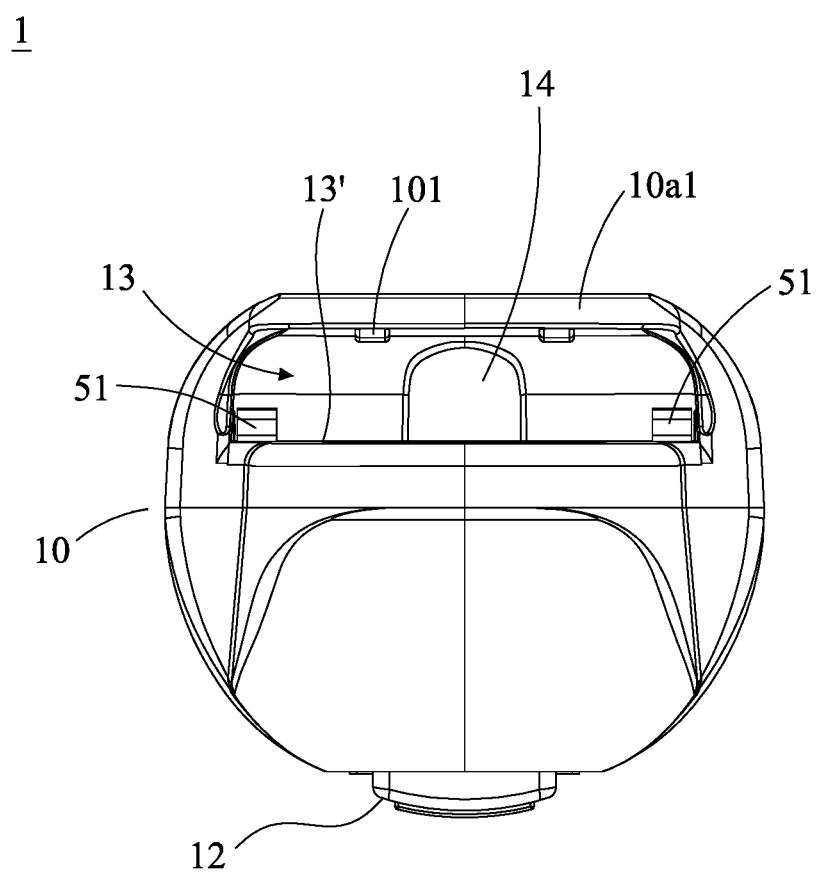
FIG. 1F is a rear view of the charging device of FIG. 1A.
Figure 1G:
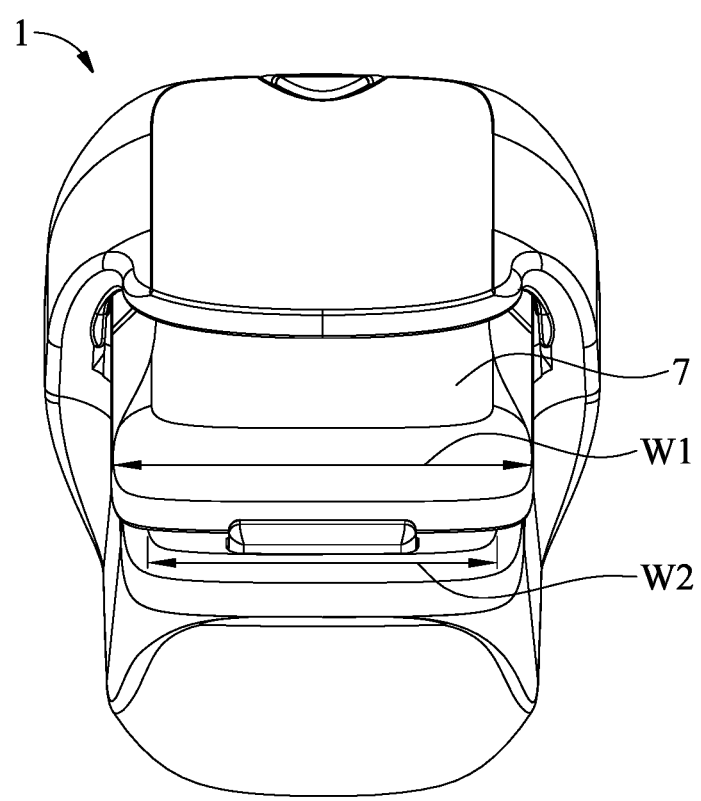
FIG. 1G is a rear top view of the charging device of FIG. 1B.
Figure 2:
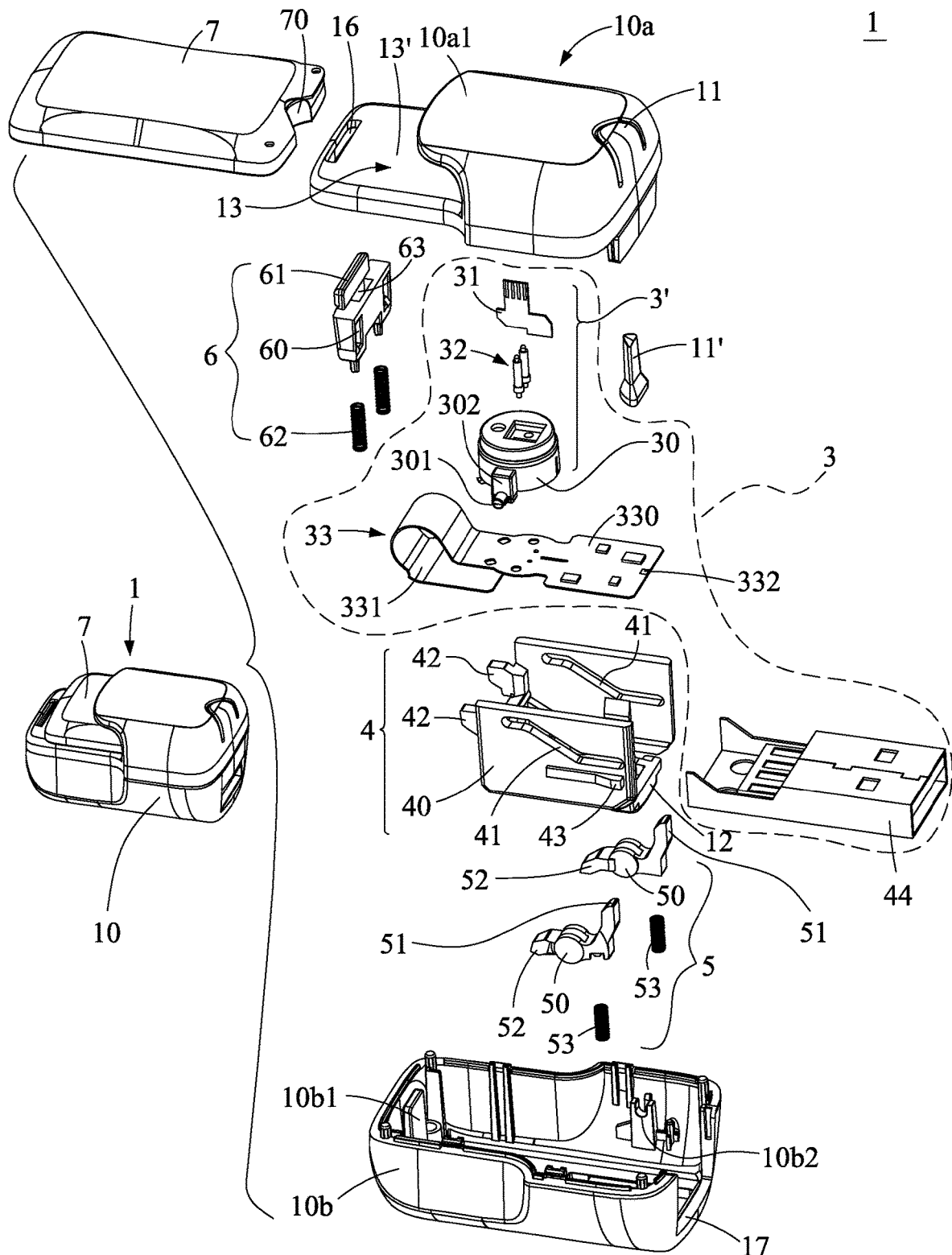
FIG. 2 is an exploded view of the charging device of FIG. 1B.

Please refer to FIG. 2, which is an exploded view according to a first embodiment of the present invention. It can be seen that the housing (body) 10 in FIGS. 1A-1G can be further divided into an upper housing 10*a* and a lower housing 10*b*. The upper housing 10*a* includes the aforementioned indicating area 11, the cover plate 10*a*1, and the placing portion 13 having a bearing surface 13' formed thereon, most of which have been described above, and will not be repeated here. A second matching portion 70 is formed on the transmitter 7. As described above, it can be seen in FIG. 2 that the shape of the indicating area 11 is similar to that of the second matching portion 70. This design can be used to visually remind the user of the direction to put the transmitter 7 into the charging device. The first matching portion 14 on the charging device is a convex shape (please refer to FIG. 1F), and the second matching portion 70 on the transmitter 7 is a concave shape. When the first matching portion and the second matching portion are combined with each other, a foolproof structure is formed, and the first connecting port 73 and the opening 15 are correctly aligned (not shown).

Please continue to refer to FIG. 2. The charging device 1 includes a charging module 3. The charging module includes a second electrical connecting port 3', a circuit assembly 33, and a third connecting port 44. The second connecting port 3' includes a charging seat 30, and a first conductive connector 31 and a second conductive connector 32 are disposed on the charging seat 30. The first conductive connector 31 is usually a golden finger type connector for transmitting the power and the signal. The second conductive connector 32 is usually a pogo pin for serving as the ground. On the lateral side of the charging seat 30, there is a second guiding structure 301 to serve as a sliding element, and the first sliding element 301 is disposed on the charging seat 30 via a sliding element pedestal 302. The circuit assembly 33 is used to perform the charging and the charging control or the signal transmitting control for the physiological signal transmitter. One end of the circuit assembly 33 is a circuit board 330. The circuit board 330 is equipped with a light-emitting element 332 and other related electronic elements, and electrically connected to the first conductive connector 31 and the second conductive connector 32. Above the light-emitting element 332, there is a light-guiding element 52' disposed in the upper housing 10*a*. The light-guiding element 52' is usually located in the first matching portion 14 (please see FIG. 1F), and its shape is usually just fit the indicating area 11. Therefore, the indicating area 11 is made of a transparent or translucent material, or itself serves as a part of the light-guiding element 52'; that is, the shape of the light-guiding element 52' is corresponding to the second matching portion 70, and the indicator area 11 also serves as a light signal area. The other end of the circuit assembly 33 is a flexible electrical connecting element 331, which is usually a flexible printed circuit for maintaining the electrical connection with the plug 44 serving as a third electrical connecting port to input power source. The flexible electrical connecting element 331 can also be replaced with a sliding pin conductive structure or a sliding rail conductive structure.

Please continue to refer to FIG. 2. The charging device 1 includes an operating module 4. The operating module 4 includes an operating portion 40 for driving the second electrical connecting port 30 to be electrically connected to the first electrical connecting port 73 of the transmitter 7. The operating portion 40 has a third electrical connecting port 44 assembled thereon, and has a first guiding structure 41. The first guiding structure 41 is usually a sliding rail or a sliding groove for coupling with the first sliding element 301. When the operating portion 40 is driven to move laterally, the first guiding structure 41 guides the first sliding element 301 to move longitudinally, thereby driving the charging seat 30 to move up and down. Hence, the first sliding element 301 also serves as a second guiding structure. In addition, the aforementioned push-pull key 12 is disposed below the operating portion 40; that is, the user drives the operating portion 40 to move laterally via the push-pull key 12 (for the detailed operations, please refer to FIGS. 7A and 7B). The push-pull key 12 and the operating portion 40 can be integrally formed, or they are respectively independent elements.

Please continue to refer to FIG. 2. The charging device 1 further includes a first locking module 5 (or referred to as a stopping module 5 and a first locking portion 5) for releasably restricting the movement of the second electrical connecting port 3'. One end of the stopping module 5 is an actuating end 51, and the other end thereof is a stopping end 52. The actuating end 51 extends into the placing portion 13, i.e. protruding from the bearing surface 13', and the stopping end 52 is coupled with a blocked portion 43 disposed on the operating portion 40; that is, the blocked portion 43 is blocked by the stopping end 52 so that it cannot move laterally. Therefore, the operating portion 40 cannot guide the first sliding element 301 to move longitudinally via the first guiding structure 41. Hence, the first locking module 5 achieves the effect of indirectly restricting the movement of the second electrical connecting port 3'. Moreover, the first locking module 5 further includes an elastic element 53 for keeping the actuating end 51 normally extending into the placing portion 13 when the transmitter 7 is not placed in the placing portion 13. At this time, the stopping end 52 also keeps normally stopping the blocked portion 43. There is a pivoting portion 50 between the actuating end 51 and the stopping end 52. The pivoting portion 50 is pivoted to the pivoting frame 10*b*2 of the lower housing 10*b*. When the actuating end 51 is pressed by the transmitter 7, the first locking module 5 can rotate with the pivoting portion 50 as the center of rotation, and rotate with the pivoting frame 10$b$2 as the fulcrum (for detailed front and rear operations, please refer to FIGS. 4B and 5A).

Please continue to refer to FIG. 2. The charging device 1 further includes a second locking module 6 (or referred to as a second locking portion 6, a positioning module 6, and a baffle 61). The positioning module 6 is disposed on the charging device 1 near the rear side, has a baffle 61 which can extend from the baffle exit 16 to reach the placing portion 13, and has an elastic element 62 for providing the baffle 61 with an elastic force to enable the baffle 61 to extend from the baffle outlet 16. The second locking module 6 also has a first connecting end 60 for connecting to the second connecting end 42. The second locking module 6 also has a guiding structure 63, which is a notch, coupled to a guiding element 10$b$1 of the lower housing 10$b$ so that the baffle 61 can only move in the up and down directions without shifting or rotating (for the detailed operations, please refer to FIGS. 4C and 6C). In other embodiments, a part of the charging module 3, the operating module 4, the first locking module 5, or the second locking module 6 can form a housing structure similar to the lower housing 10$b$ to form an internal space with the upper housing 10 to accommodate various elements (not shown). The operating module 4, the first locking module 5, and the second locking module 6 are collectively referred to as a controlling module. The controlling module is used to control the operating process between the transmitter 7 and the charging module 3 to maintain a safe state so that when the transmitter 7 and the second electrical connecting ports 3' are separated or connected, the transmitter 7 can both be protected. This prevents the parts from being damaged due to the improper operation by the user (for the detailed operations, please refer to FIGS. 4A to 6C). In other embodiments, the first locking module 5 or the second locking module 6 respectively collocates with the operating module 4, and the first locking module 5, the second locking module 6, and the operating module 4 are collectively referred to as a control module.

Please refer to FIGS. 3A to 3D, wherein 3A shows that the transmitter 7 is detachably disposed on a sensor module 8 and connected to the sensor assembly 81, and the sensor module 8 includes a sensor pedestal 80 and the sensor assembly 81. The sensor pedestal 80 can be adhered to the skin S through an adhesive sheet ST, at this time the transmitter 7 is configured to transmit the signal from the sensor 810 to the outside.

Figure 3A:
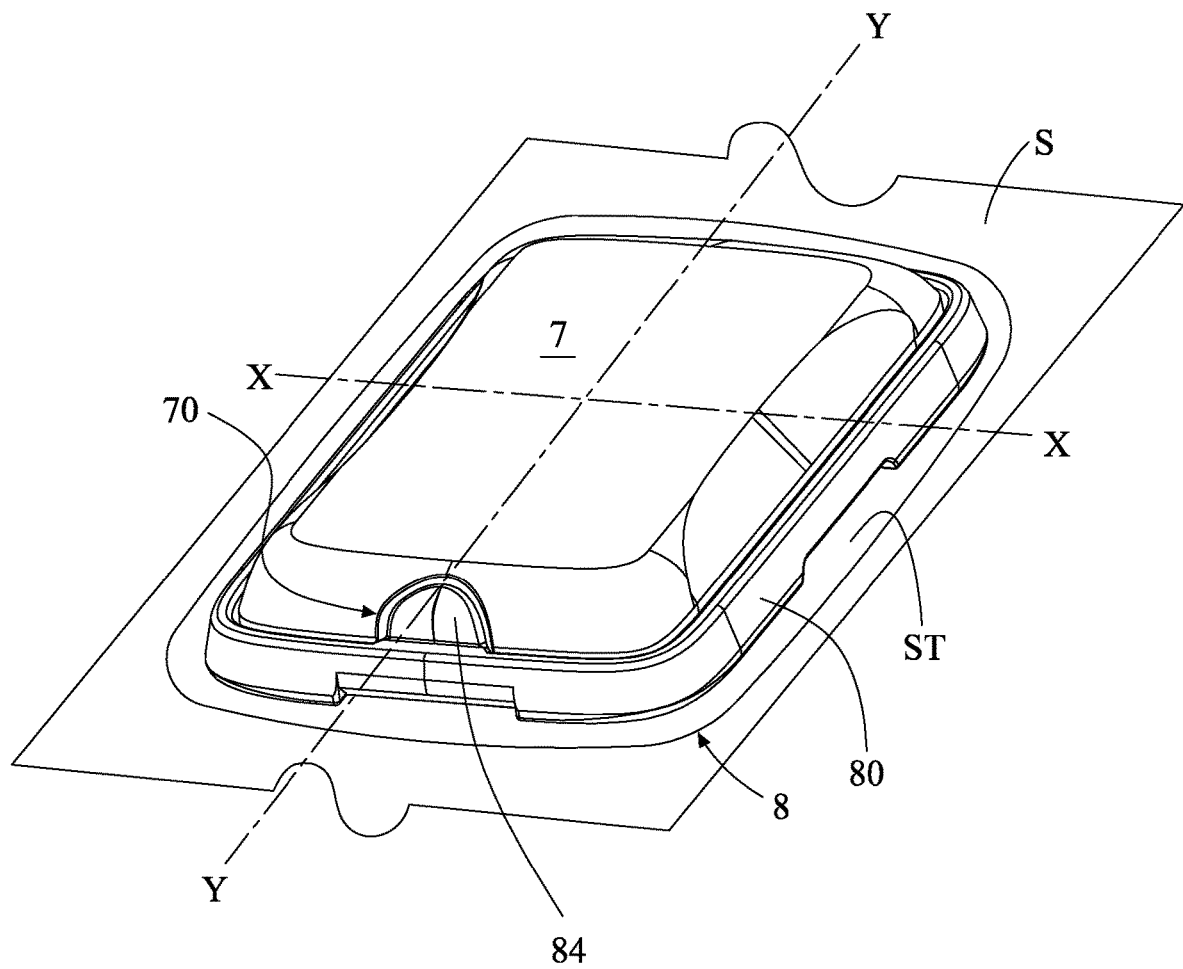
FIG. 3A is a three-dimensional schematic diagram of the appearance of the transmitter of the present invention during detection.
Figure 3B:
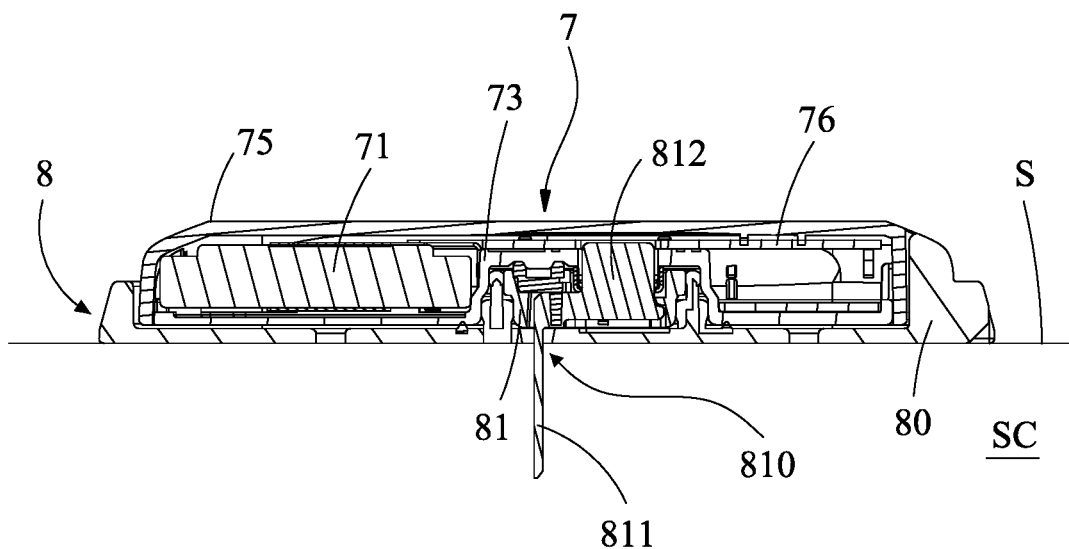
FIG. 3B is a cross-sectional view of the transmitter of the present invention along the Y-Y direction during detection.
Figure 3C:
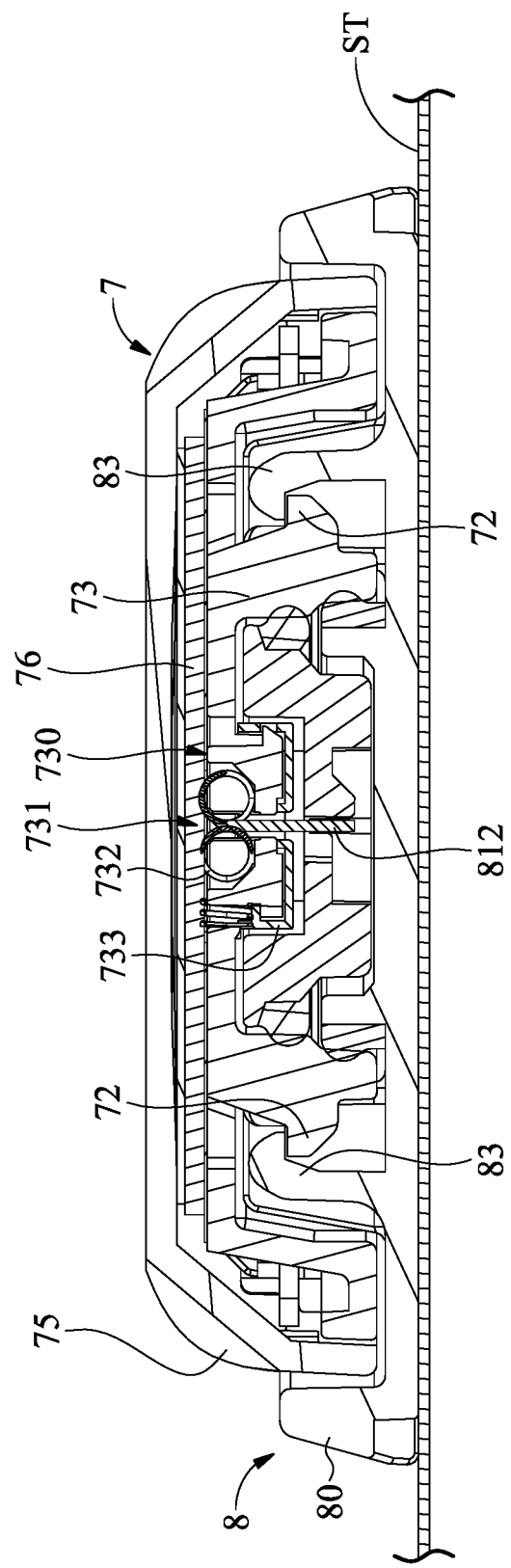
FIG. 3C is a cross-sectional view of the transmitter of the present invention along the X-X direction during detection.
Figure 3D:
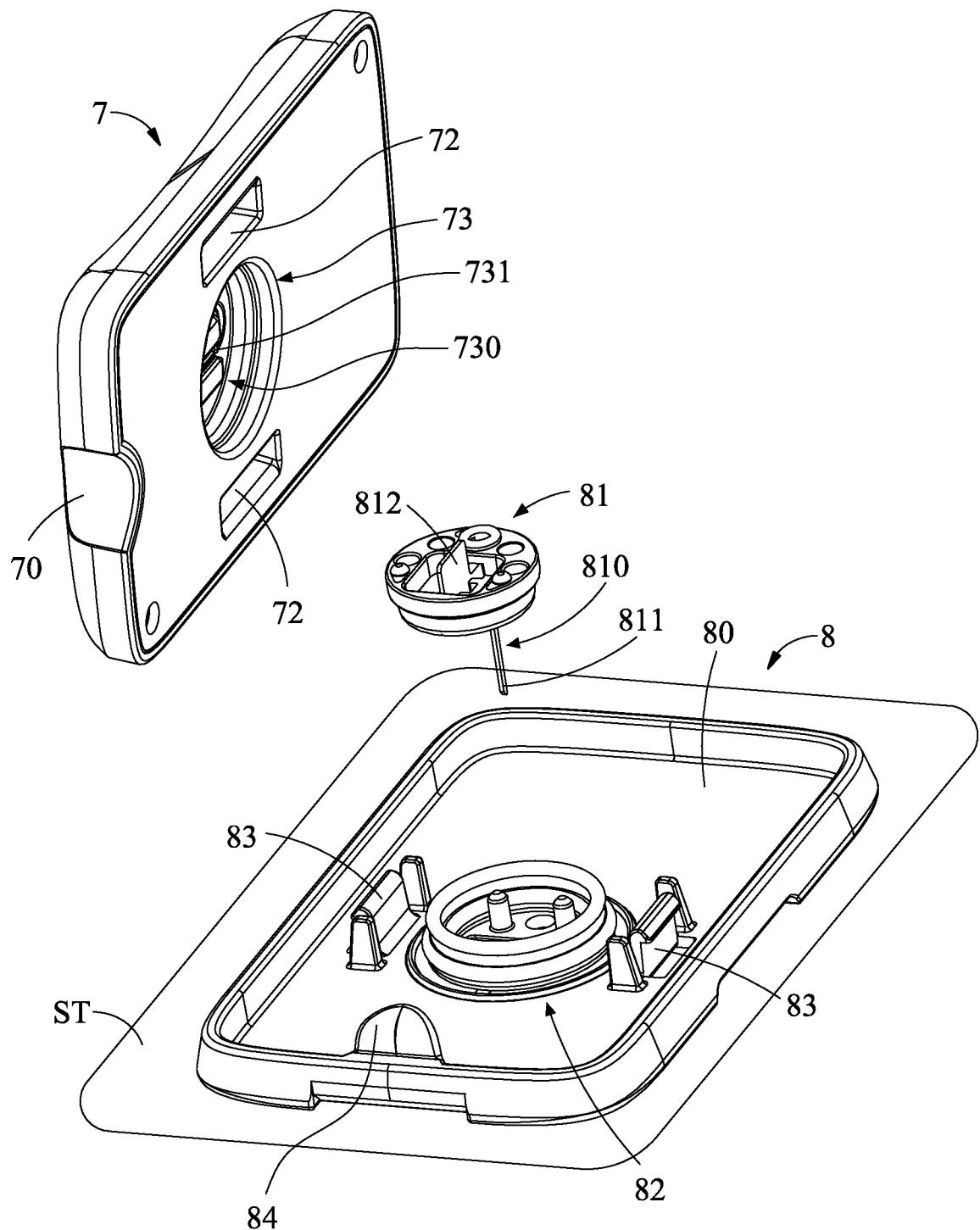
FIG. 3D is a schematic diagram of the separation of the transmitter and the sensor module of the present invention.

Please refer to FIGS. 3B to 3D. The transmitter 7 includes a battery 71 and a first electrical-connecting port 73 having an input portion 730 which has a groove structure used to match the structure of either the sensor assembly 81 or a second electrical-connecting port 30 and an insert hole 731 equipped with an input terminal 732 and a secondary input terminal 733. The battery 71 provides electric power for the operation such as signal output of the transmitter 7. The input terminal 732 is used for electrically connecting the output terminal 812 or the first conductive connector 31. In addition, the transmitter 7 also includes a first buckling structure 72 for buckling and fixing with the second buckling structure 83 of the sensor pedestal 80. The sensor assembly 81 is fixed in the sensor assembly fixing structure 82 of the sensor base 80. The piercing end 811 of the sensor 810 penetrates the subcutaneous tissue SC, while the output terminal 812 of the sensor 810 enters the input portion 73 and is electrically connected to the input terminal 730 in the transmitter 7, so the signal measured by the sensor 810 can be transmitted to the outside through the transmitter 7. In order to prevent the transmitter 7 from being installed on the sensor base 80 in a wrong direction, the sensor pedestal 80 further includes a matching positioning portion 84 for matching with the second matching portion 70, so that when a user tends to cover the transmitter 7 on the sensor base 80, the installation direction can be identified through the appearance of the structure to achieve the effect of being foolproof. The transmitter 7 of the present invention is only one embodiment thereof, and the charging device 1 of the present invention can also be applied to other types of transmitters. The physiological signal transmitter 7 used in the present invention usually includes a sensor transmitter 75. The body 75 also includes a circuit board 76, a battery 71 electrically connected to the circuit board 76, and a first electrical connecting port 73 exposed to the outside.

Figure 4A:
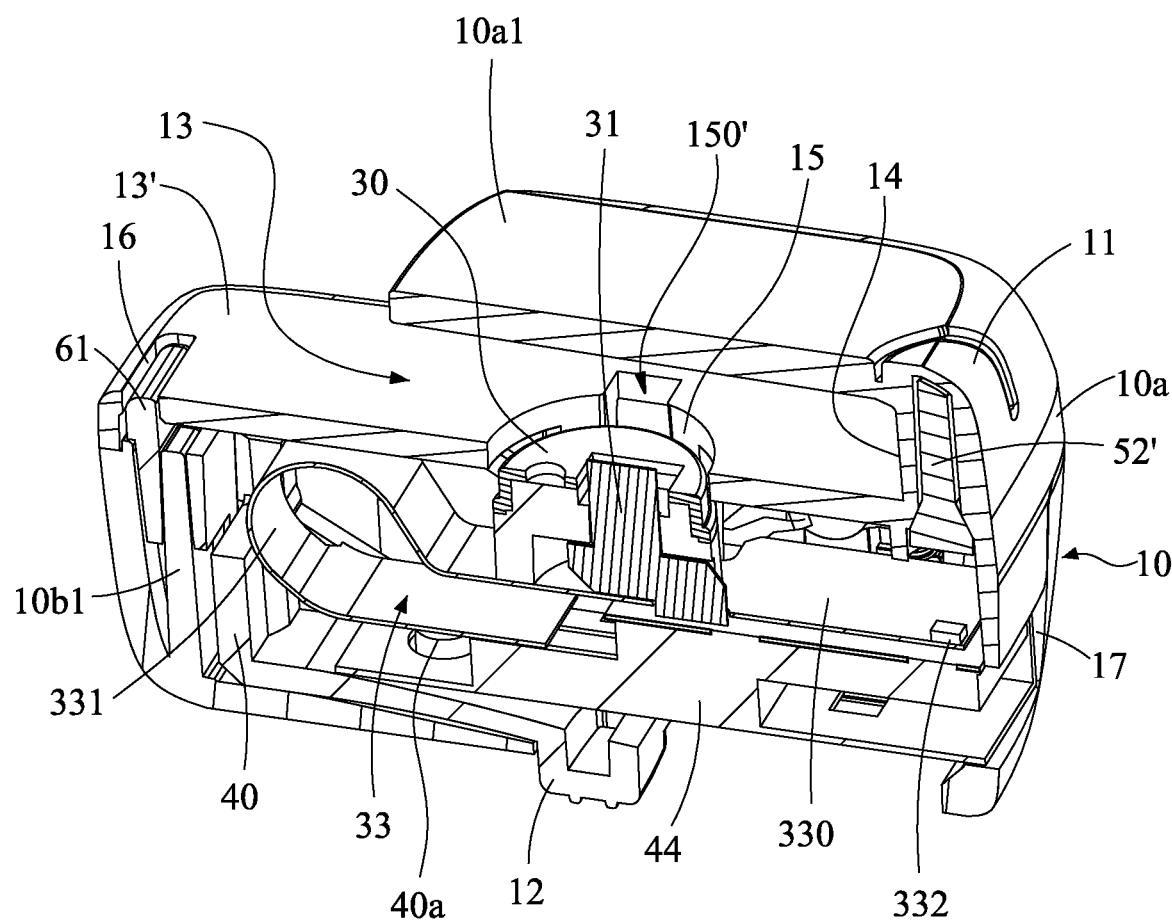
FIGS. 4A-4C are side-sectional perspective views of different cutting lines deviating from the center line of the charging device of the present invention, showing the state that the transmitter has not been placed on the charger.
Figure 4B:
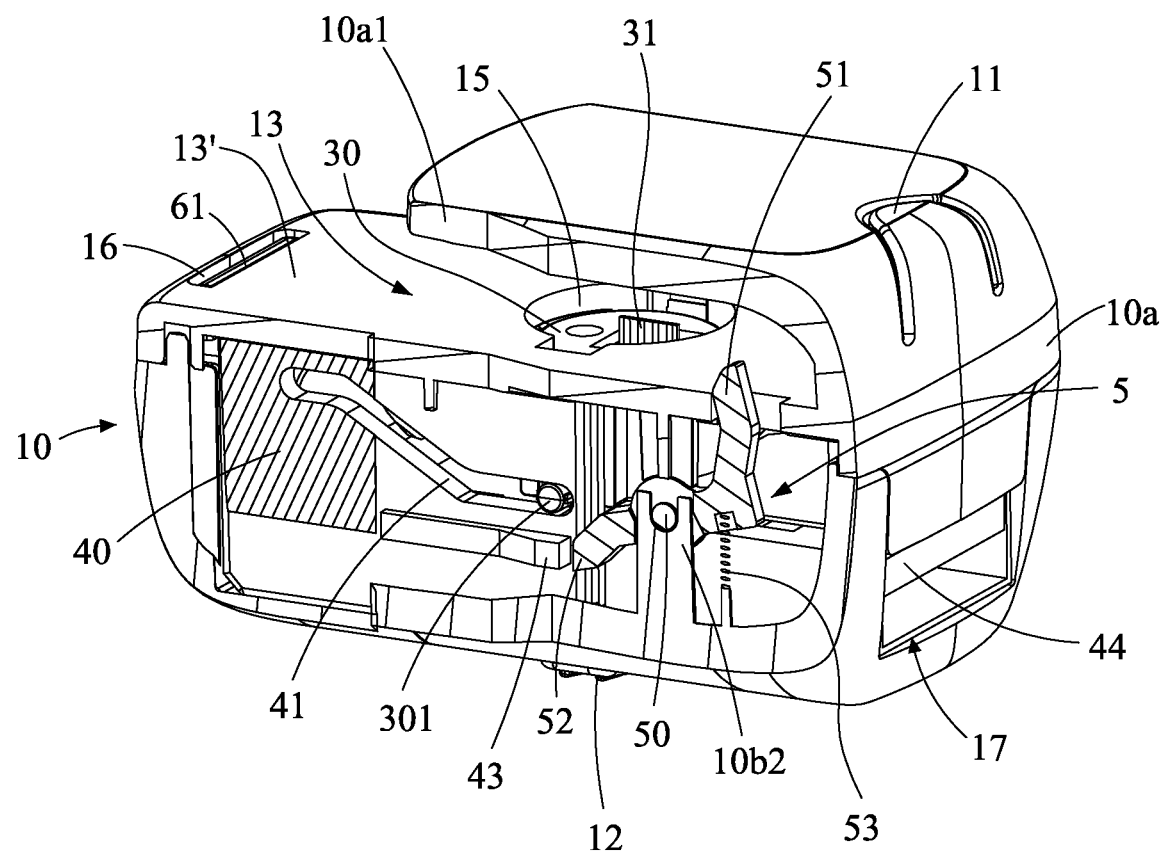

Please refer to FIGS. 4A to 4D, which illustrate the state when the charging device 1 is not furnished with the transmitter 7. Please refer to FIG. 2 for the reference numeral of each component. In FIGS. 4A and 4B, the charging module 3 is in the first operating state, the second electrical connecting port 30 is not actuated to be placed at the first position (corresponding to the bearing surface 13' in the retracted state) inside the opening 15, i.e., a non-charging position, the opening 15 includes a sliding groove 150', the circuit assembly 33 is disposed in the housing 10 and including a circuit board 330 and an electrical connecting element 331. The circuit board 330 is equipped with a light-emitting element 332, and is electrically connected to the first conductive connector 31 in the charging seat 30. The electrical connector 331 is a flexible material that is electrically connected to the electrical connection plug 44, usually by welding on the output end of the plug 44. The upper housing 10$a$ has a light-guiding element 52' disposed in the indicating area 11 at the front and a baffle exit 16 at the rear, wherein a baffle 61 sheathed in the guiding element 10$b$1 is disposed in the baffle exit 16. The operating portion 40 is also disposed in the housing 10. A push-pull key 12 is disposed at the bottom of the operating portion 40$a$, and the electrical connecting plug 44 is also locked with the fixing block 40$a$ on the operating portion 40. In another embodiment, the push-pull key can be designed as to be actuated by the other methods.

Figure 4C:
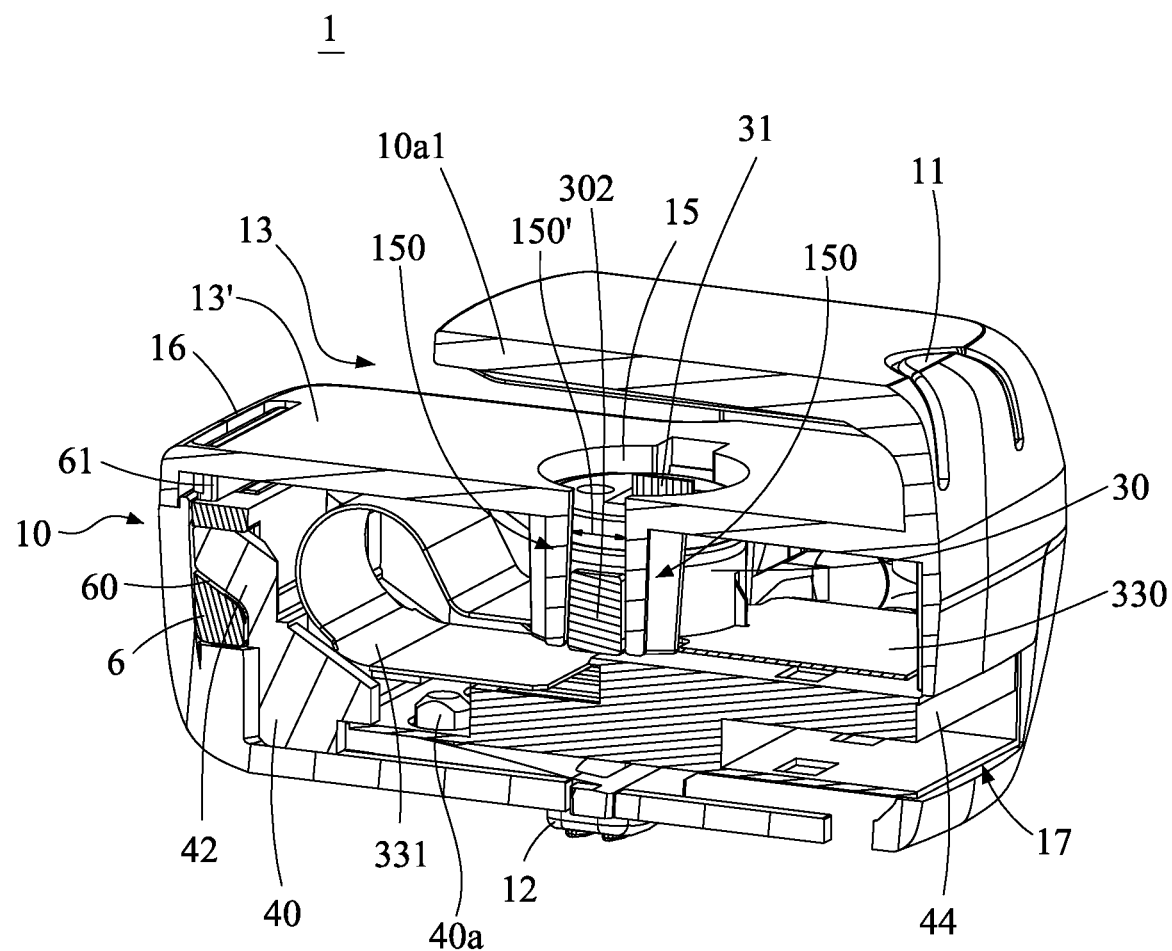
Figure 4D:
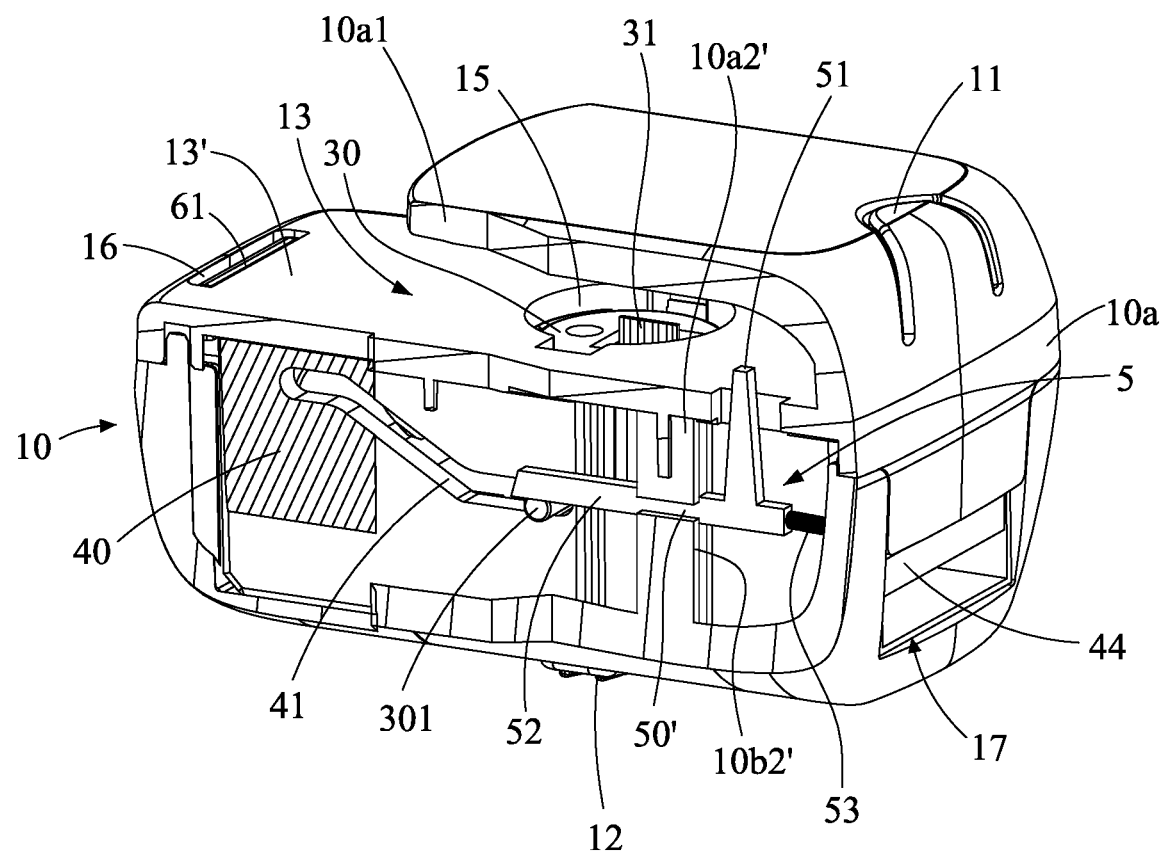
FIG. 4D is a schematic diagram of another embodiment of the stopping module of the charging device of the present invention.

Please refer to FIGS. 4A and 4B. A first matching portion 14 for matching with the second matching portion 70 of the transmitter 7 is disposed in the placing portion 13 corresponding to the front of the housing 10, rendering the transmitter 7 to be placed at a pre-determined position. The operating module 4 is in the first operating state, wherein the first guiding structure 41 of the operating portion 40 is coupled to the second guiding structure 301 of the charging seat 30, and the second guiding structure 301 is not yet sliding in the first guiding structure 41 at this moment. In FIGS. 4C and 4D, the first guiding structure 41 is an oblique groove with an inclined surface guiding the movement of the second guide structure 301. The operating portion 40 has a blocked portion 43 that is locked or stopped by the stopping end 52 of the first locking module 5. Therefore, when the push-pull key 12 tends to drive the operating portion 40 due to an external force or shaking of the operating portion 40 itself, the first guiding structure 41 will not drive the second guiding structure 301, thereby preventing the second electrical connecting port 30 from being accidentally driven toward the second position (corresponding to the bearing surface 13' in an extended state). Furthermore, because the first conductive connector 31 is lighter and more compact, the potential issue of damage to the first conductive connector 31 if a user wants to force the transmitter 7 in or out can also be avoided. FIG. 4B further discloses the position of the actuating end 51 of the first locking module 5 extending into the placing portion 13. A pivot portion 50 pivoted on the pivot frame 10b2 of the lower housing 10b between the actuating end 51 and the stopping end 52 of the first locking module (stop part) 5, so the first locking module 5 has a structure similar to a rocker. When the actuating end 51 is pressed down, the stopping end 52 rises (see FIG. 5A). In addition, an elastic element 53 connects the first locking module 5 with the lower housing 10b, to provide elastic force to maintain the moving end 51 protruding from the bearing surface 13' when under a condition the transmitter 7 is not placed in the charging device 1 (that is, when the actuating end 51 is not depressed).

Please refer to FIG. 4C, showing when the second guiding structure 301 is not driven by the first guiding structure 41, and the sliding element pedestal 302 does not follow the second guiding structure 301 to move, in order to avoid a moving of the charging seat 30 in an unexpected direction. The present invention is further provided with at least one guiding portion 150 on the outside of the opening 15 to form a sliding groove 150', so that the sliding groove 150' and the opening 15 are connected with each other and the sliding element pedestal 302 is guiding the second electrical connecting port 30 in the sliding groove 150' to expand and contract from the opening 15 in a fixed direction. The second locking module 6 further includes a first connecting end 60. When under the first operating state, the operating portion 40 is at the first position, and the second connecting end 42 is connected with the first connecting end 60 to prevent the baffle 61 from being pushed by the elastic element 62. At this moment, the second electrical connecting port 30 is located at a first position (contracted state relative to the bearing surface 13'), so that the second locking module 6 is pressed down to keep the baffle 61 inside the baffle exit 16, that is, not extending out of the baffle exit 16, and the second locking module 6 releases the positioning of the transmitter 7 to allow the transmitter 7 to be inserted in or taken out of the placing portion 13.

Please refer to FIG. 4D, which discloses another embodiment of the first locking module of the charging device in the present invention, wherein the first locking module is replaced with a locking block. 5, which has a sliding body 50, one end of which is an actuating end 51 and the other end is a stopping end. 52, and the second guiding structure 301 of the charging module protrudes outside the first guiding structure 41 and is blocked by the stopping end 52 on the top. When the transmitter 7 is not placed in the placement portion 13, the locking block 5 is normally moved toward the baffle 61 due to the spring 53 (that is, the pushing force in the opening direction of the placing portion 13). Thus, when the second guiding structure 301 is pushed upward by the first guiding structure 41, it will be blocked by the stopping end 52 and cannot move upwardly. On the other hand, when the transmitter 7 is inserted into the placement portion 13 in the correct direction, that is, the second matching portion 70 is facing inward, the transmitter 7 can push the actuating end 51 to move deeper into the placement portion 13, and then drive the locking block 5 moves in the same direction. At this time, the stopping end 52 is moved away from the upper side of the second guiding structure 301. Therefore, when the user drives the first guiding structure 41 through the push-pull key 12, the second guide structure 301 is driven upward, and the stop end 52 no longer blocks the second guiding structure 301. According to the abovementioned embodiment, the first blocking module can restrict the movement of the second electrical connecting port 3' by the releasable coupling of the stopping module with the charging module or the operating module. The restriction of the movement that the first locking module to the second electrical connecting port may be a complete prohibition or merely a partial displacement but unable to render an effective contact with the first electrical connecting port 73 (FIG. 3D).

Figure 5A:
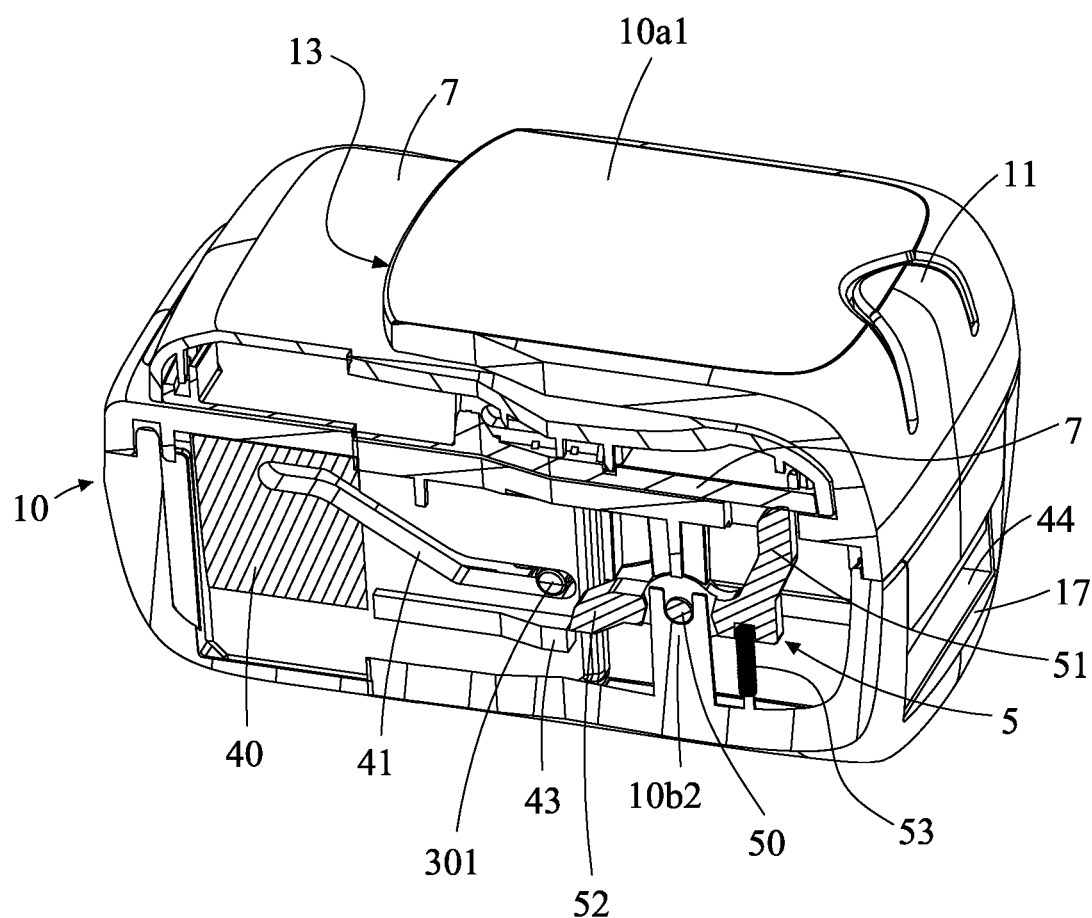
FIG. 5A is a lateral sectional perspective view of the charging device of the present invention, showing the state that the transmitter is placed on the charger.
Figure 5B:
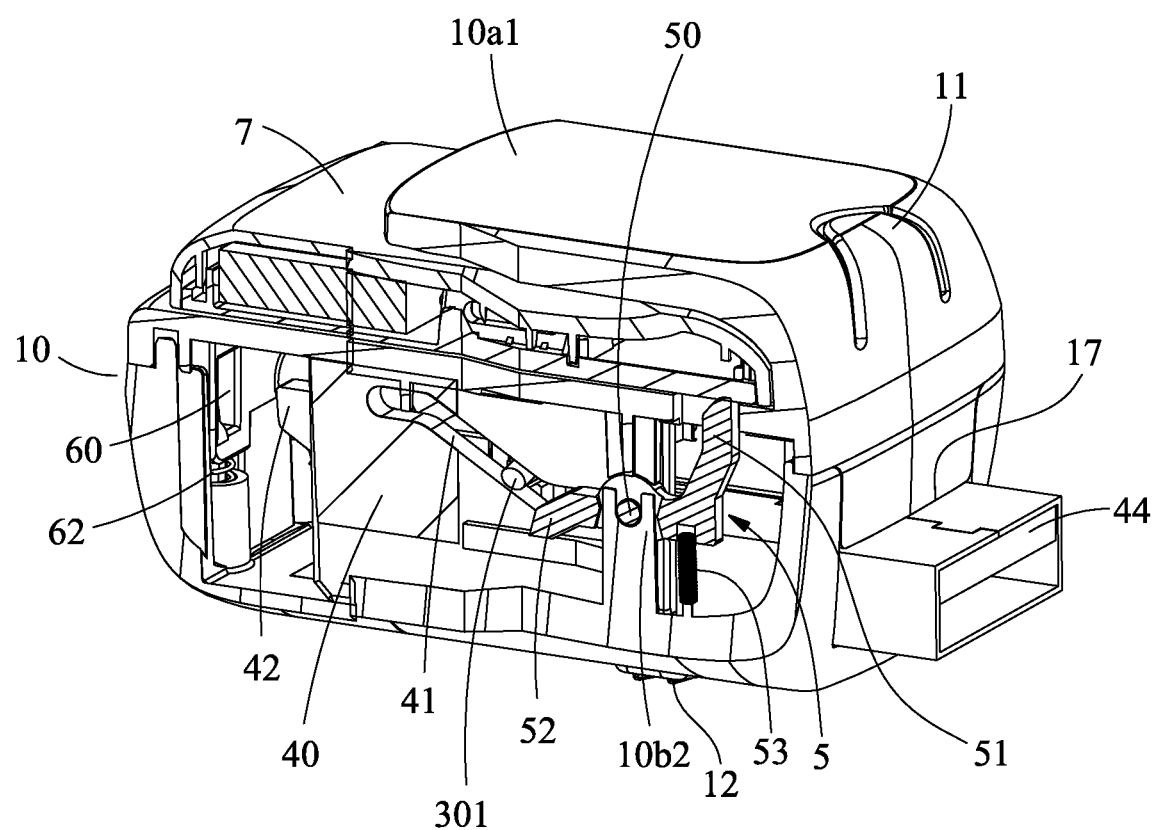
FIG. 5B is another lateral sectional perspective view of the charging device of the present invention, showing the state that the second electrical connection port moves from the first position to the second position.
Figure 5C:
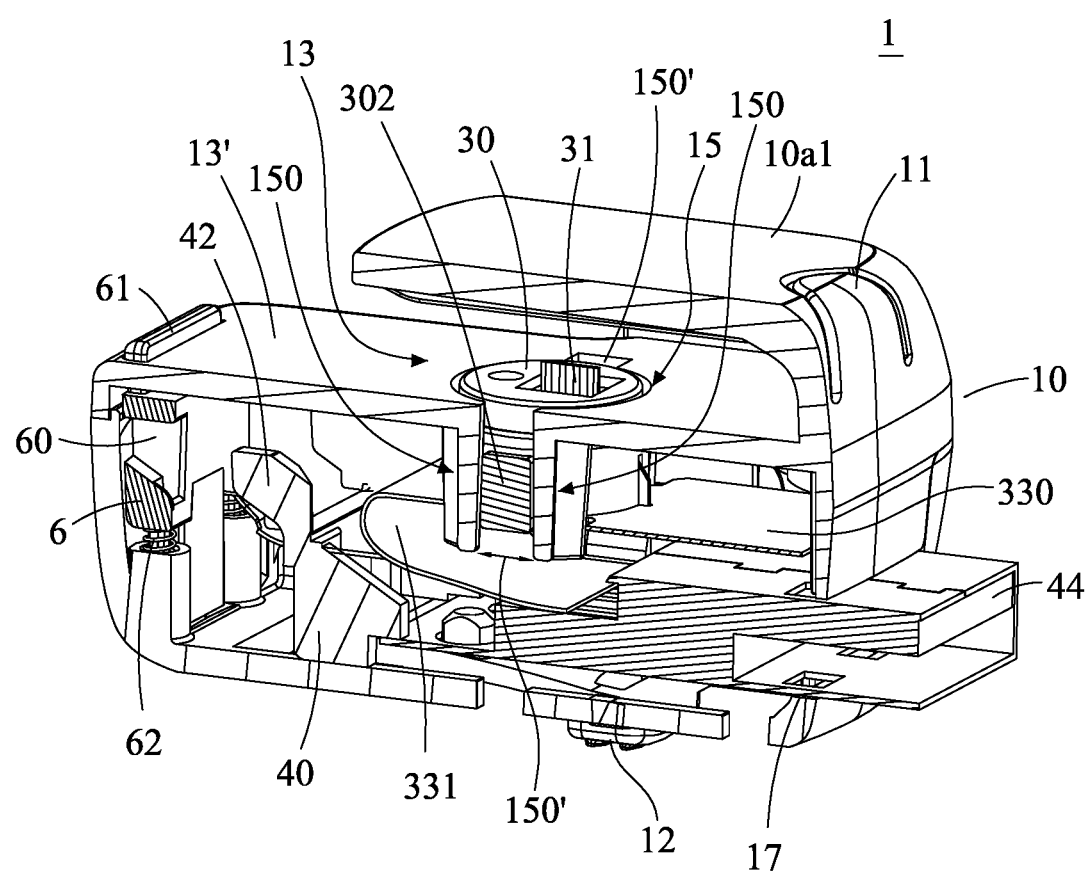
FIG. 5C is another lateral sectional perspective view of the charging device of the present invention, showing the state that the transmitter is placed on the charger and second electrical connection port moves from the first position to the second position but the transmitter is hidden.

Please refer to FIGS. 5A to 5C, which respectively show the state when the transmitter 7 is placed at the pre-determined location in the charging device 1 and the operating portion 40 is controlled to drive the second electrical connecting port 3' to protrude the bearing surface 13'. Please also refer to the reference numeral of each component in FIGS. 2 and 3A to 3D, which will not be repeated hereinafter. FIG. 5A shows the state when the transmitter 7 is placed at a pre-determined location of the bearing surface 13' of the charging device 1. Even when the transmitter 7 is in a relatively correct position, the actuating end 51 is actuated by the transmitter 7 to detect whether the transmitter 7 is at a predetermined position. When the transmitter 7 is at the predetermined position, the stop end 52 releases the locking to the operating portion 40 to allow the operating portion 40 to drive the second electrical connecting port 3' to move between the first position and the second position, and to form a connection or separation with the first electrical connecting port 73. In FIG. 5A, being at the predetermined location, the transmitter 7 presses the actuating end 51 to rotate the first locking module 5, and at the same moment, the stopping end 52 is lifted and releases the blocked portion 43 so as to release the movement restriction of the second electrical connecting port. At this moment, the elastic element 53 is compressed, and after the transmitter 7 is taken out, the elastic restoring force of the elastic element 53 will drive the actuating end 51 to extend upward to the placing portion 13 (the same as the state in FIG. 4B).

Figure 6A:
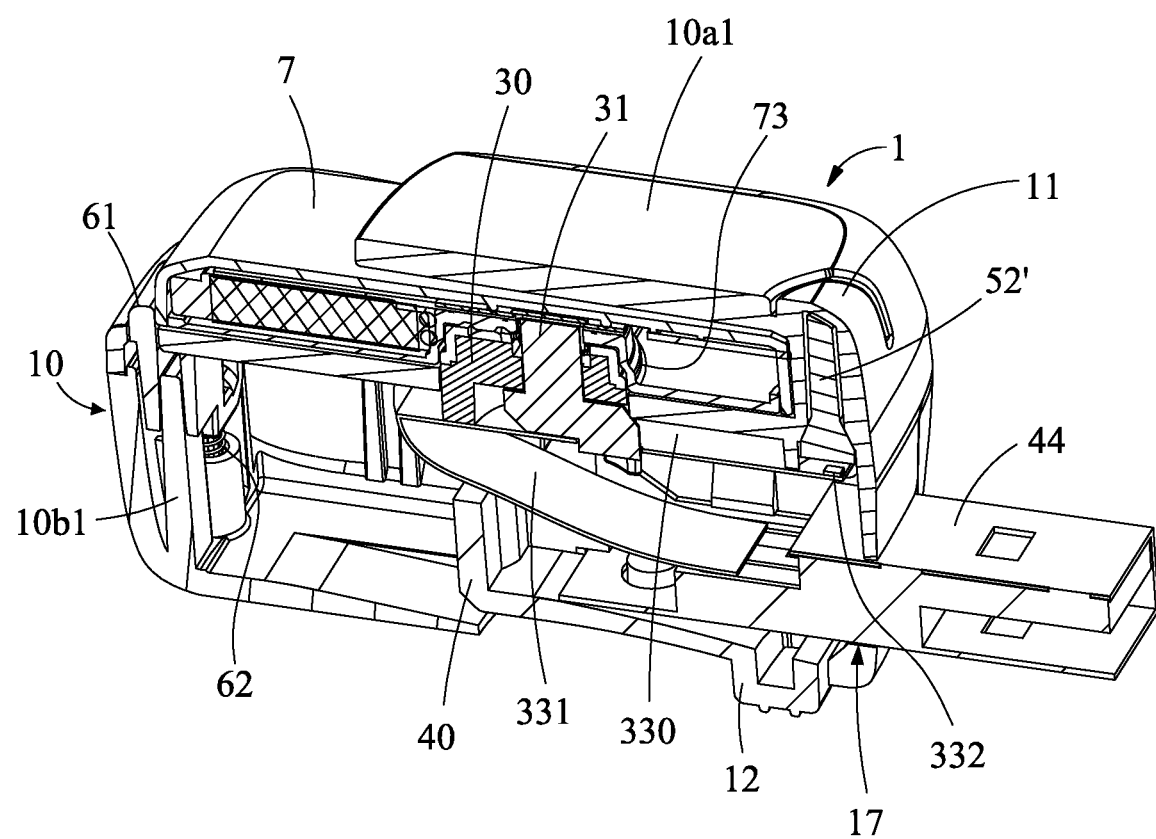
FIGS. 6A-6C are side-sectional perspective views of different cutting lines deviating from the center line of the charging device of the present invention, showing the state that the transmitter is placed on the charger and operating.
Figure 6B:
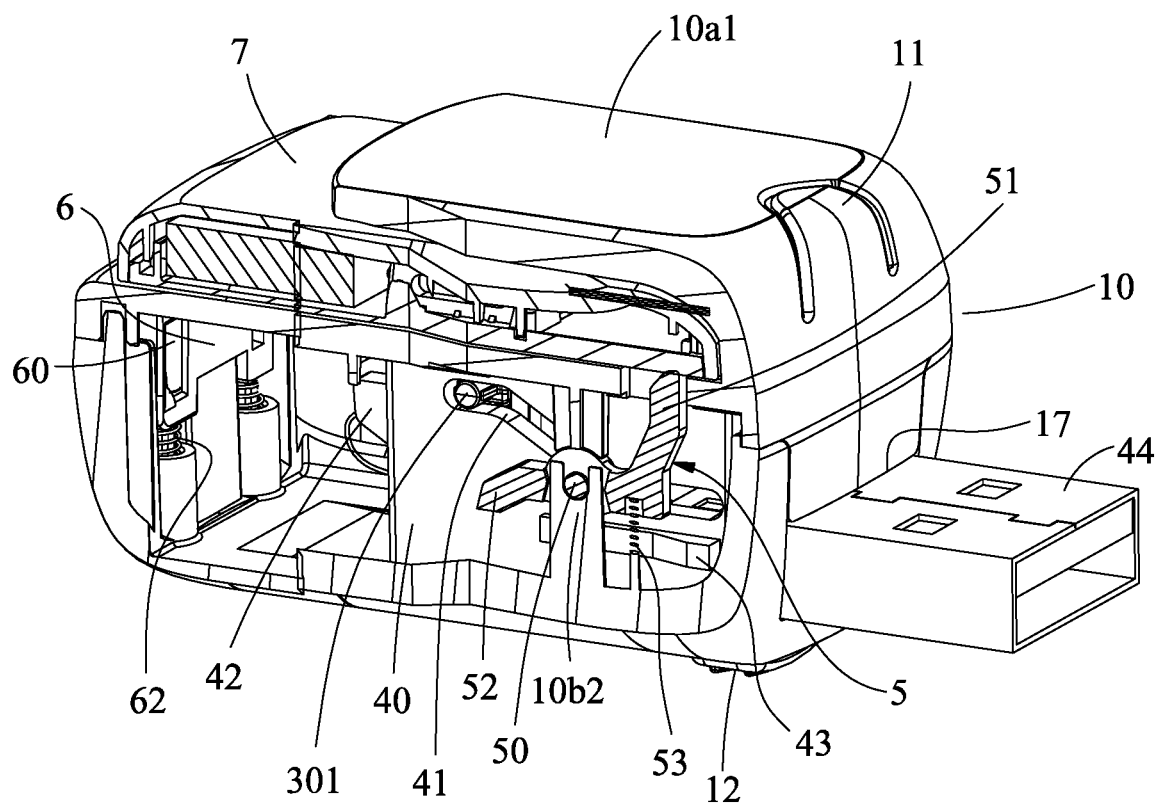

Please refer to FIGS. 5B to 5C, showing the state when the operating portion 40 is controlled to drive the second electrical connecting port 3' from the first positing moving toward the second position, after the transmitter 7 is placed on the placing portion 13 and the push-pull key 12 is operated to push out a part of the electrical connecting plug 44. In FIGS. 5B-5D, when the pushing is in the direction to the right, the stopping end 52 of the first locking module (the first locking portion) 5 has been lifted and can no longer stop the blocked part 43, the second electrical connecting port 3' releases the movement restriction, and the push-pull button 12 drives the operating portion 40 to move in the same direction. Meanwhile, the first guiding structure 41 pushes the second guiding structure 301 to move upward, and then drives the charging seat 30 to move upward from the opening 15 and toward the first electrical connecting port 73 of the sensor 7 (in conjunction with FIGS. 3D and 6A) while having the first conductive connector 31 move toward the insert hole 731 (see FIG. 3C). At the same time, the electrical connecting plug 44 partially extends out of the opening 17. In addition, when the operating portion 40 moves to the right, the second connecting end 42 is separated from the first connecting end 60 of the second locking portion 6 (as shown in FIG. 5C), so the elasticity potential of the elastic element 62 due to the pressing can be released to push the baffle 61 out of the baffle exit 16 and stop the rear end of the transmitter 7 to achieve the effect of positioning the transmitter 7 on the placing portion 13. Please refer to FIG. 5C, which shows the state where the transmitter 7 is hidden to illustrate the placing portion 13 alone after the transmitter 7 is placed, the push-pull key 12 is operated to push out a part of the electrical connecting plug 44, and the charging seat 30 and the first conductive connector 31 thereof is at the location during escalating in the opening 15. Please refer to FIGS. 6A to 6D, showing the state in which the operating portion 40 is controlled to drive the second electrical connecting port 3' at the second position, and the electrical connecting plug 44 is fully pushed out after the transmitter 7 is inserted. Please also refer to the reference numeral of each component in FIGS. 2 and 3A to 3D, which will not be repeated hereinafter. In FIGS. 6A and 6B, when the movement restriction of the first locking module 5 over the second electrical connecting port 30 is released, the operating portion 40 drives the second electrical connecting port 3' moves from the first position to the second position (relative to the bearing surface 13' in an extended state) in the opening 15 and is electrically connected to the first electrical connecting port 73, i.e. a charging position, wherein the charging seat 30 extends from the opening 15 to achieve the connection with the first electrical connection port 73, making the first conductive connector 31 enters the insert hole 731 and is electrically connected to the input terminal 732 of the transmitter 7 (the position shown in FIG. 3C). The push-pull key 12 is pushed to the front of the housing 10, which is the right most portion in the drawing, and the electrical connecting plug 44 also completely extends out of the opening 17. At this situation, the circuit board 330 is also lifted to the highest position, and the light-emitting element 332 is the closest to the light-guiding element 52'. At this moment, the illumination of the light-emitting element 332 can be transmitted to the indicating area 11 through the light-guiding element 52' and makes overall operating process have both foolproof and light-guiding effects, and the internal space of the charging device 1 is effectively used to make the charging device 1 miniaturized.

At this time, the light-emitting element 332 is ready to illuminate. When the electrical connecting plug 44 is plugged into an external power source such as an AC power adapter, a computer USB socket, a car charging adapter or a device equipped with a USB socket (please refer to the charger 1 in FIG. 6H which can be plugged into a USB socket on a personal computer 91, the charger 1 in FIG. 6I which can be plugged into a mobile phone charger 92 or a car cigarette light USB adapter 93 in FIG. 6J), etc., so that the light-emitting element 332 can illuminate and provide indication and instructions, and indicate the usage status of the charger 1 by different light-emitting colors and patterns.

Figure 6C:
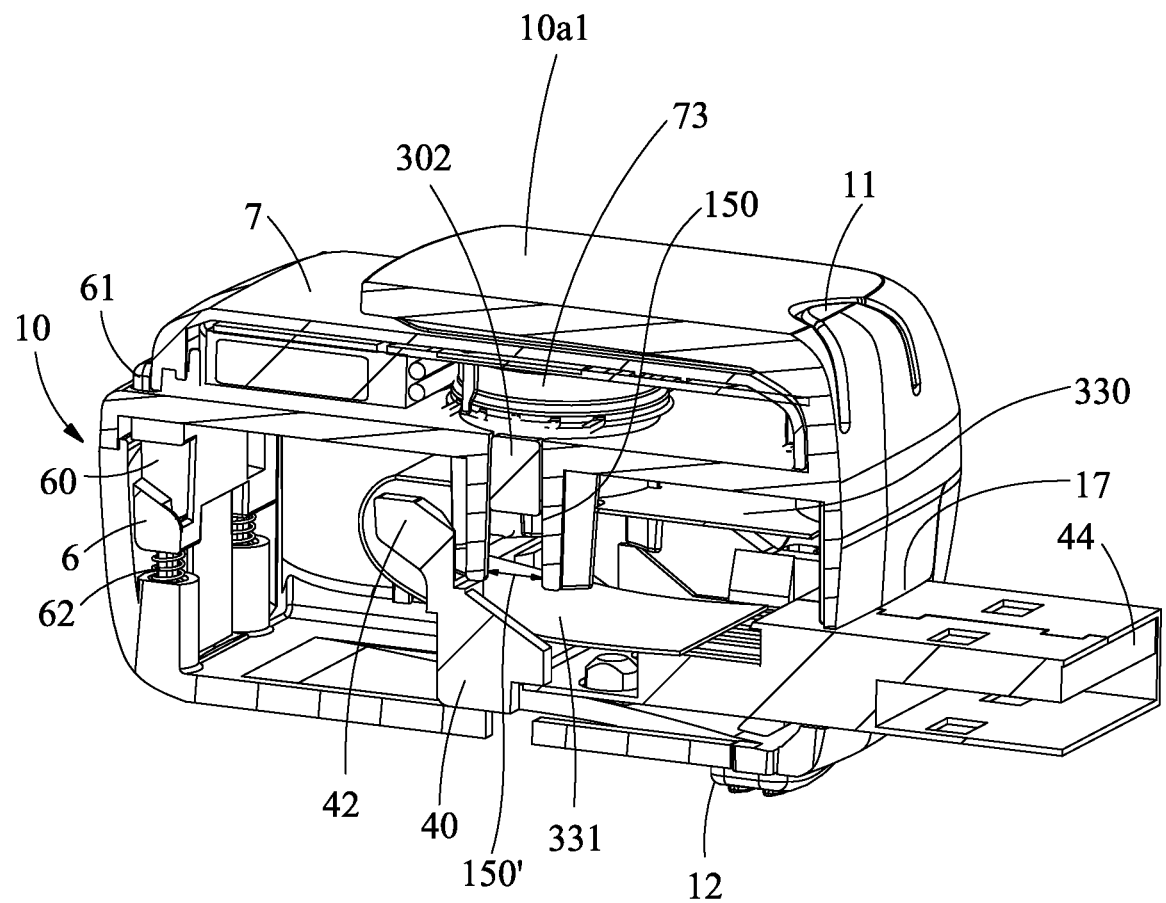
Figure 6D:
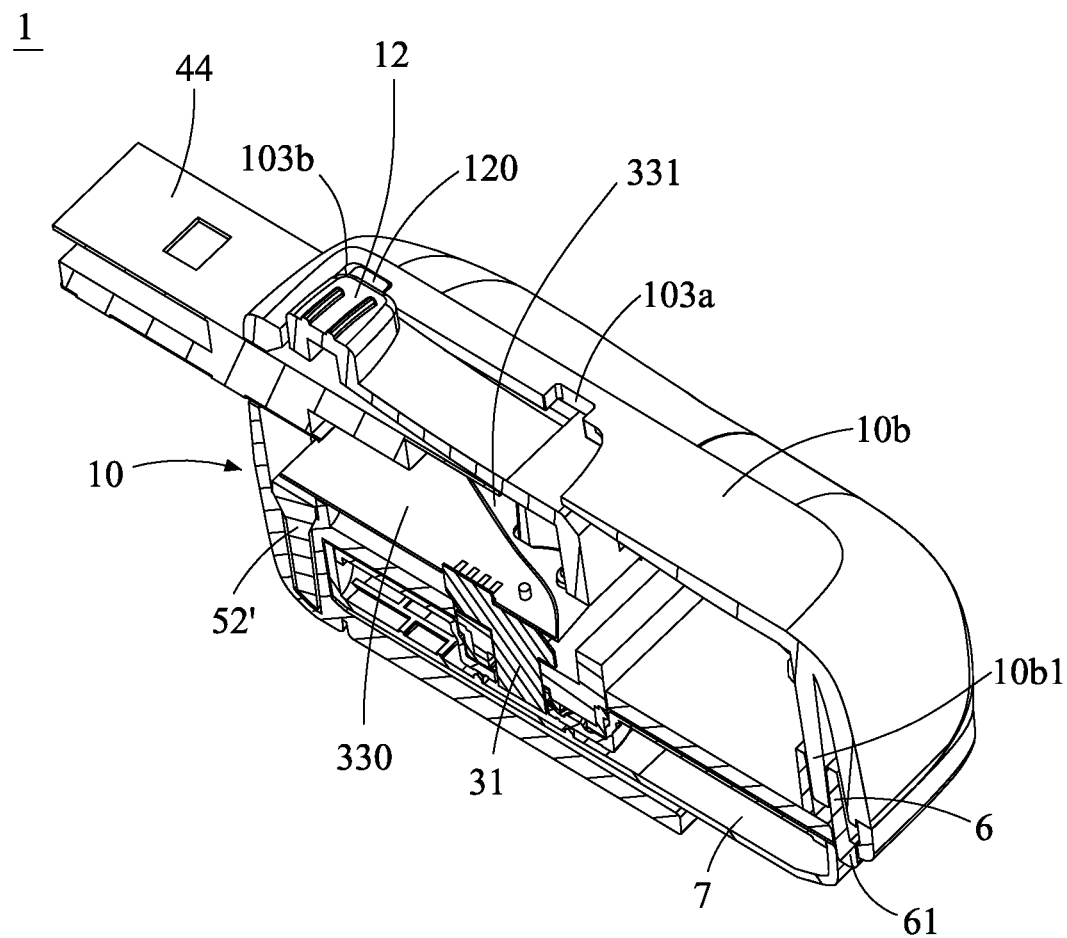
FIG. 6D is a side-sectional perspective view of the rear bottom longitudinal side section of the charging device of the present invention, showing the state that the transmitter is placed on the charger and the operation is completed.
Figure 6E:
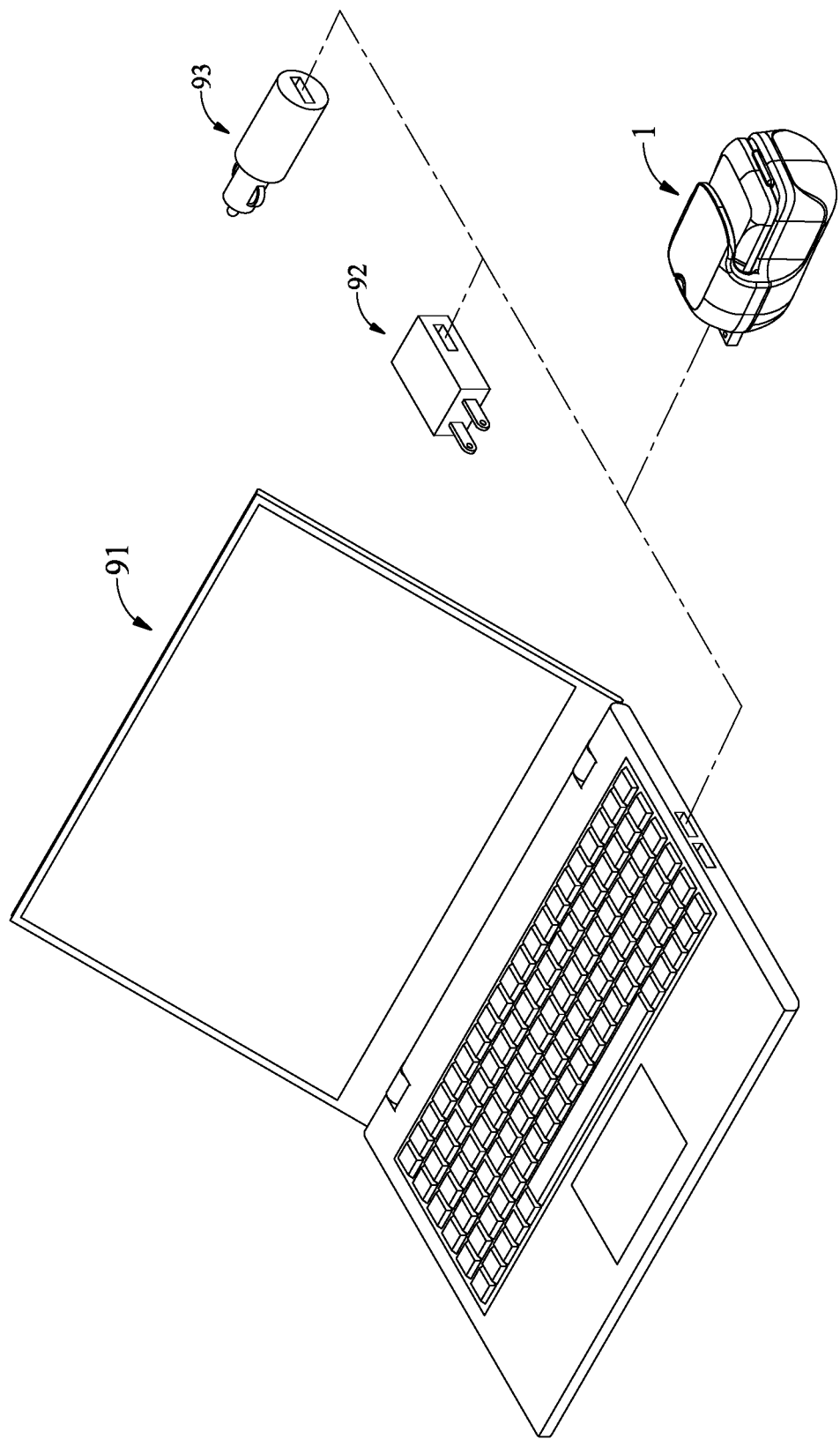
FIG. 6E is a schematic diagram showing the connection between the charging device of the present invention and various external power sources.

Please refer to FIG. 6C, the operating module 3 is in the second operating state. It can be seen that when the push-pull key 12 is pushed to the end of front direction of the housing 10, the operating portion 40 has also reached the position closest to the front end of the housing 10, and at this time the second guiding structure 301 is also pushed up to the highest position by the first guiding structure 41. Relatively, the state of the electrical connecting plug 44 in FIG. 6C is pushed out, while in FIG. 4C is withdrawn back. FIG. 6C discloses that the sliding element pedestal 302 has also lifted to a high position of the sliding groove 150', and the second connecting end 42 of the second locking portion (baffle 61) 6 is separated from the first connecting end 60, so the elasticity potential of the elastic element 62 that was originally pressed can be released to push the baffle 61 out of the baffle exit 16 and stop the rear end of the transmitter 7 so as to hold the transmitter 7 on the placing portion 13, positioning and locking the transmitter 7, so as to prevent the first electrical connecting port 73 and the second connecting port 3' in electrical connection from accidentally picking and placing the transmitter 7 and damaging the second connecting port 3. Furthermore, at the same moment, the second electrical connection port 3' is in a second position (relative to the bearing surface 13' in an protruding state), the baffle 61 extends out of the baffle outlet 61, so that the second locking portion 6 positions the transmitter 7 on the hearing surface 13' and prevents the transmitter 7 from being put in or taken out from the placing portion 13 to protect the first conductive connector 31 of the second electrical connecting port 3' from being damaged by improper operation of the transmitter 7. When the charging module 3 is in the third operating state, that is, when the operating portion 40 drives the second electrical connection port 3' to move from the second position back to the first position to separate from the first electrical connecting port 73, and the operating portion 40, after through the second connecting end 42 pressing the first connecting end 60 and lowering the baffle 61 (referring to the operating state as shown in FIG. 4C), which drives the second locking portion 6 to retract to the hearing surface 13' to release the positioning lock of the transmitter 7, so that the first connecting port 73 and the second connection port 3' is in a separated state then the sensor 7 can be taken out. Referring to FIG. 6D, which shows an embodiment that the push-pull key 12 is located closest to the front end of the housing 10, and the positioning block 120 can be snapped into the second positioning groove 103b at the same time. After the charging is completed, the first electrical connecting plug 44 is first disconnected from the external power source, and when the push-pull key 12 is pressed into the housing 10 (please refer to FIG. 1E), the positioning block 120 is separated from the second positioning groove 103b, and the push-pull key 12 can be pushed toward the first positioning groove 103a, and finally the positioning block 120 returns into the first positioning groove 103a. At this time, the charging seat 30 is completely lowered, and the baffle 61 also returns to the baffle exit 16 without blocking the transmitter 7, so the transmitter 7 can be removed from the placing portion 13 at this time in order to prevent the first electrical connection port 73 and the second connection port 3' in electrical connection from damaging the second connection port 3' due to accidentally taking or placing the transmitter 7. Furthermore, at this moment, the second electrical connection port 3' is at a second position (relative to the hearing surface 13' in an extended state), the baffle 61 extends out of the baffle outlet 61, so that the second locking portion 6 restricts the transmitter 7 at the position of the bearing surface 13' and the transmitter 7 cannot be put in or taken out from the placing portion 13 to protect the first conductive connector 31 of the second electrical connection port 3' from being damaged by mis-operation to the transmitter 7. When the charging module 3 is in the third operating state, that is, when the operating portion 40 drives the second electrical connection port 3' to move from the second position back to the first position to separate from the first electrical connection port 73, and the operating portion 40, after through the second connecting end 42 pressing the first connecting end 60 and lowering the baffle 61 (referring to the operating state as shown in FIG. 4C), which drives the second locking portion 6 to retract to the bearing surface 13' to release the positioning lock of the transmitter 7, so that the first connecting port 73 and the second connection port 3' is in a separated state then the sensor 7 can be taken out. See FIG. 6D, it can be seen that the operation of the push-pull key 12 is in conjunction with the positioning method among the positioning block 120, the first positioning groove 103a and the second positioning groove 103b, which can reduce friction loss of the opening 17 caused by improper operation and improves the durability of the operating structure of the USB connector 44. In another embodiment, the sliding design of the push-pull key 12 does not need to press the button into the housing 10.

Figure 7A:
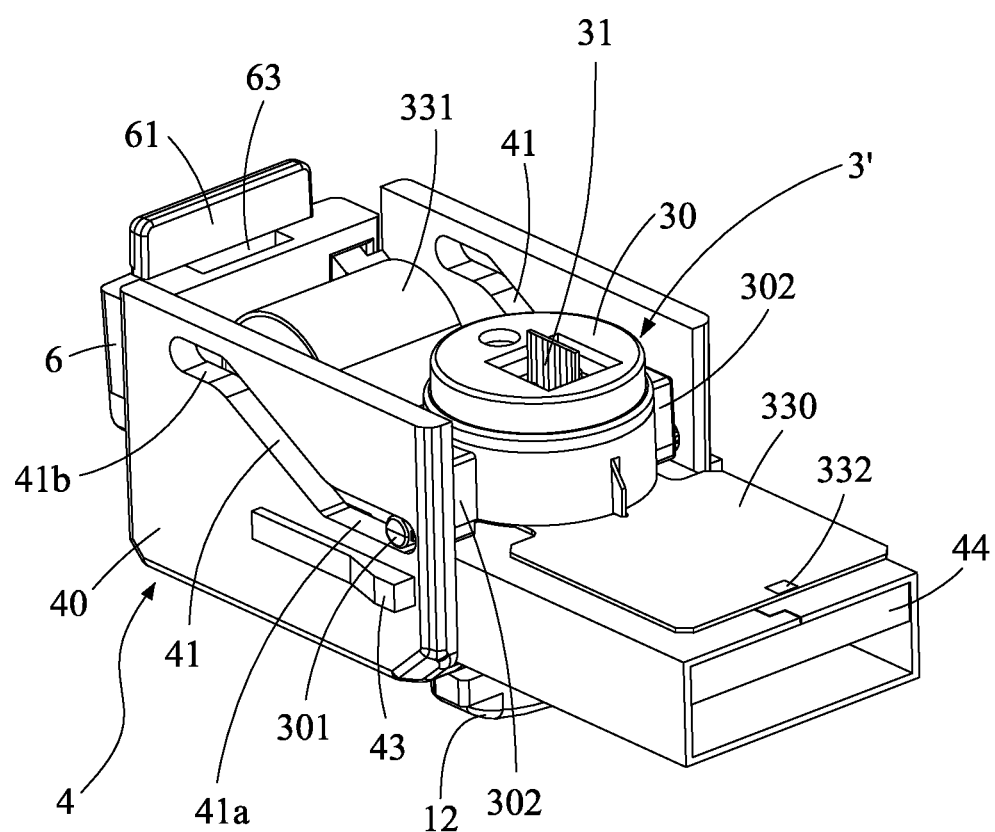
FIGS. 7A-7B each shows a schematic perspective drawing of the interior of the charging device with the body hidden according to the present invention.
Figure 7B:
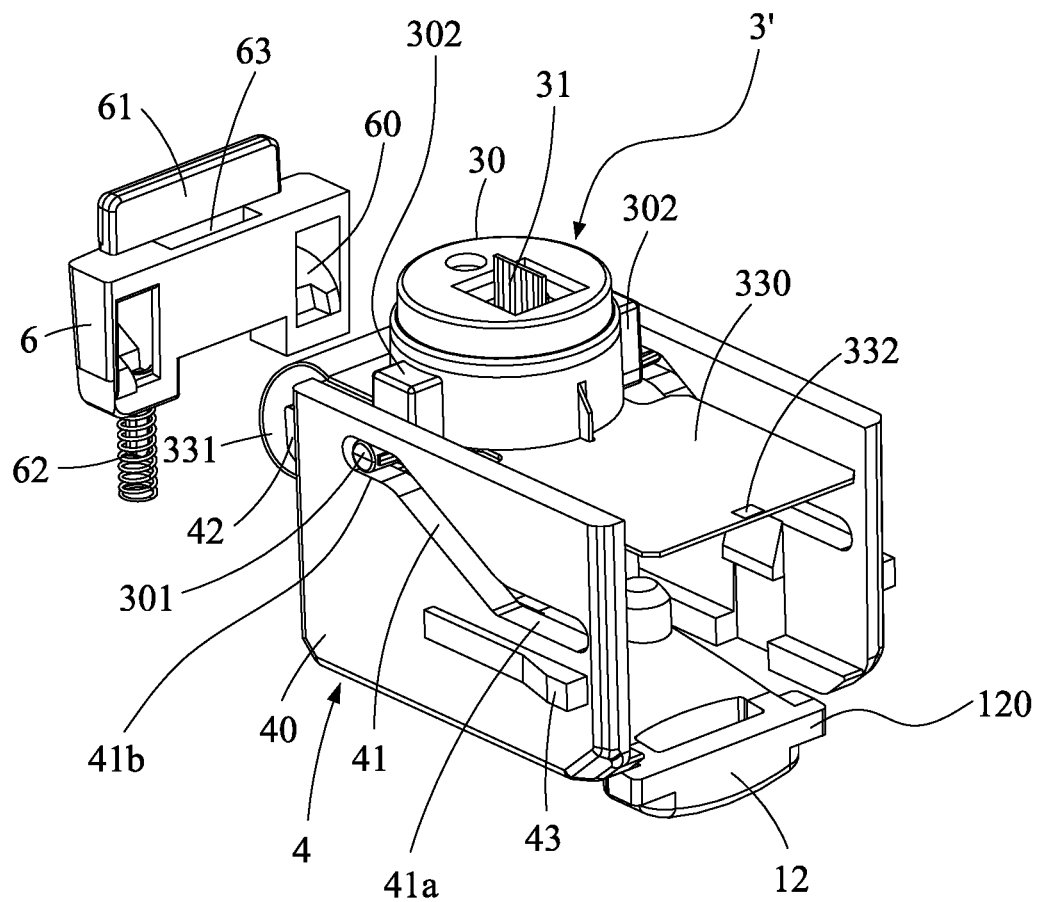

Please refer to FIGS. 7A and 7B both. The numerals of the devices are referred to those in FIG. 2 and the other drawings. As shown in FIGS. 7A and 7B, the housing 10 is removed to fully disclose the relative positions of and the connection relationship between the controlling module 4 and the charging module 3. FIG. 7A shows the first operating state of the present invention, wherein the second guiding structure 301 is located at the first position in the first guiding structure 41, where it is usually at a low position, so that the charging seat 30 of the second electrical connection port 3' is maintained in a retracted position relative to the bearing surface 13'. It can be seen from the previous drawings and descriptions that the charging seat 30 can only move up and down. Therefore, in order to prevent the charging seat 30 from an accidental up-and-down movement resulting from a vertical shaking, where the movement drives a movement of the controlling module 4 consequently, the first guiding structure 41 of the present invention is designed to be a guiding groove structure, and a first transverse groove 41a extends to form at the first position, wherein the extending direction is perpendicular to the moving direction of the second guiding structure 301. Therefore, when the charging module 1 is shaken in a direction parallel to the moving direction of the charging seat 30, because the extending direction of the first horizontal groove 41a is perpendicular to the moving direction of the second guiding structure 301, the movement of the charging seal 30 resulting from the shaking can be prevented. FIG. 73 shows the second operating state according to the present invention, where the operating portion 40 is pushed forward, so that the second guiding structure 301 is located at the second position of the first guiding structure 41, usually at a high place, so that the charging seat 30 is kept at an extended position opposite to the bearing surface. The first guiding structure 41 of the present invention further extends at the second position to form a second groove 41b, where the direction it further extends is perpendicular to the moving direction of the second guiding structure 301, so as to prevent the charging seat 30 from moving resulting from the shaking in a direction parallel to its moving direction. Please further refer to FIGS. 7A and 73 in conjunction with FIG. 2, where the first conductive connector 31 and the second conductive connector 32 are inserted on the circuit board 330, and the charging module 3 (as shown in FIG. 2) of FIG. 7B is in a state ready to charge.

Figure 7C:
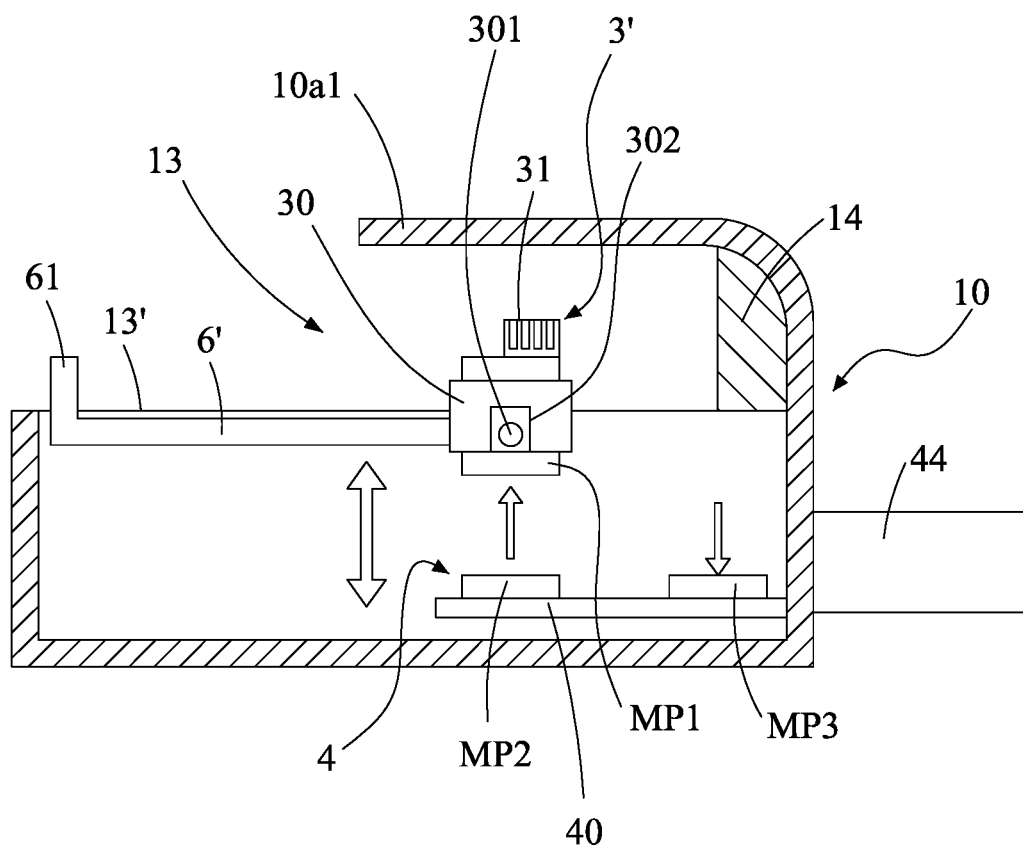
FIG. 7C shows a side cross-sectional view of the charging device according to another embodiment of the present invention.

Please refer to FIG. 7C. FIG. 7C shows a vertical cross-sectional view of the charging module and the controlling module according to another embodiment of the present invention. It is shown that the baffle 61 is directly connected to the charging seat 30 through a connecting element 6', so that the lifting and lowering of both are completely synchronized. The charging seat 30 can also be integrally formed with the baffle 61 and the connecting element 6'. In other words, the charging module 3 can be integrally formed with the baffle 61 which serves as the second locking module. The controlling module 4 and the charging module 3 are coupled and moved interactively by a magnetic force. There is a first magnetic element MP1 disposed under the charging module 3, and there are a second magnetic element MP2 and a third magnetic element MP2 on the controlling module 4. The first magnetic element MP1 magnetically repulses the second magnetic element MP2, and attracts the third magnetic element MP3. Accordingly, when the controlling module 4 is in the second operating state (i.e. it is pushed to the right till the end), the second magnetic element MP2 is located below the first magnetic element MP1, the charging module 3 is pushed upward through a repulsive force, and the baffle 61 is simultaneously driven to extend upward and to be out of the baffle exit 16. Nevertheless, when the controlling module 4 is in the first operating state (i.e. it is pushed to the left till the end), the third magnetic element MP3 is located under the first magnetic element MP1, the charging module 3 is pulled downward by the attraction, and the baffle 61 is simultaneously driven to retract downward and to be in the baffle exit 16.

Figure 8A:
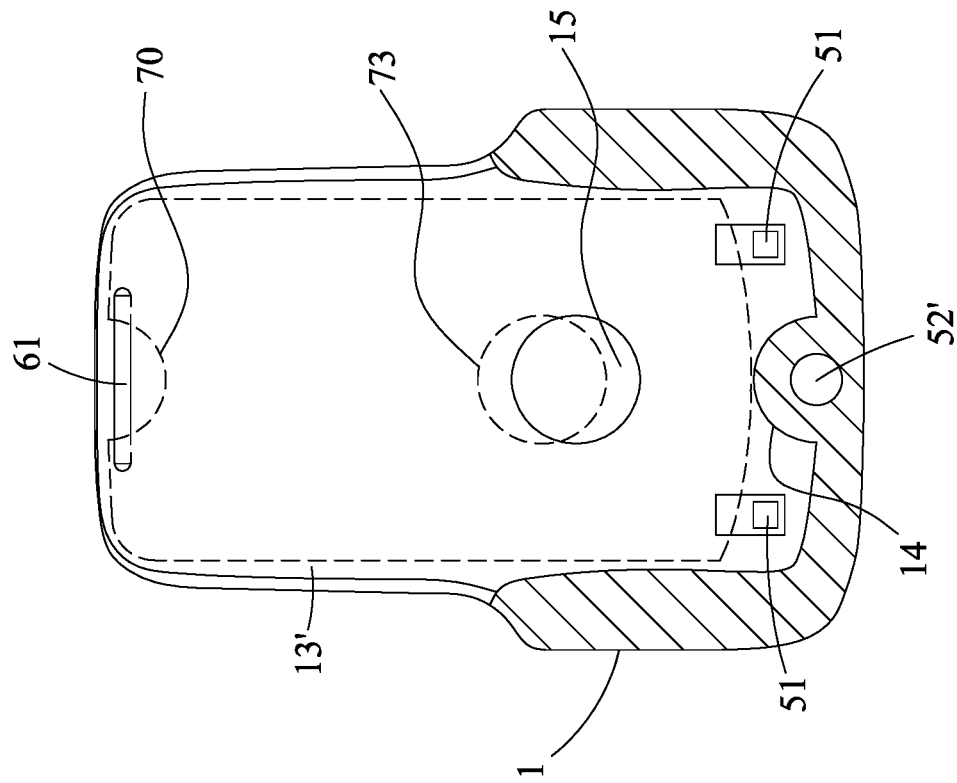
FIGS. 8A-8B each shows the top cross-sectional view of the charging device in use and installed thereon with the transmitter according to the present invention.
Figure 8B:
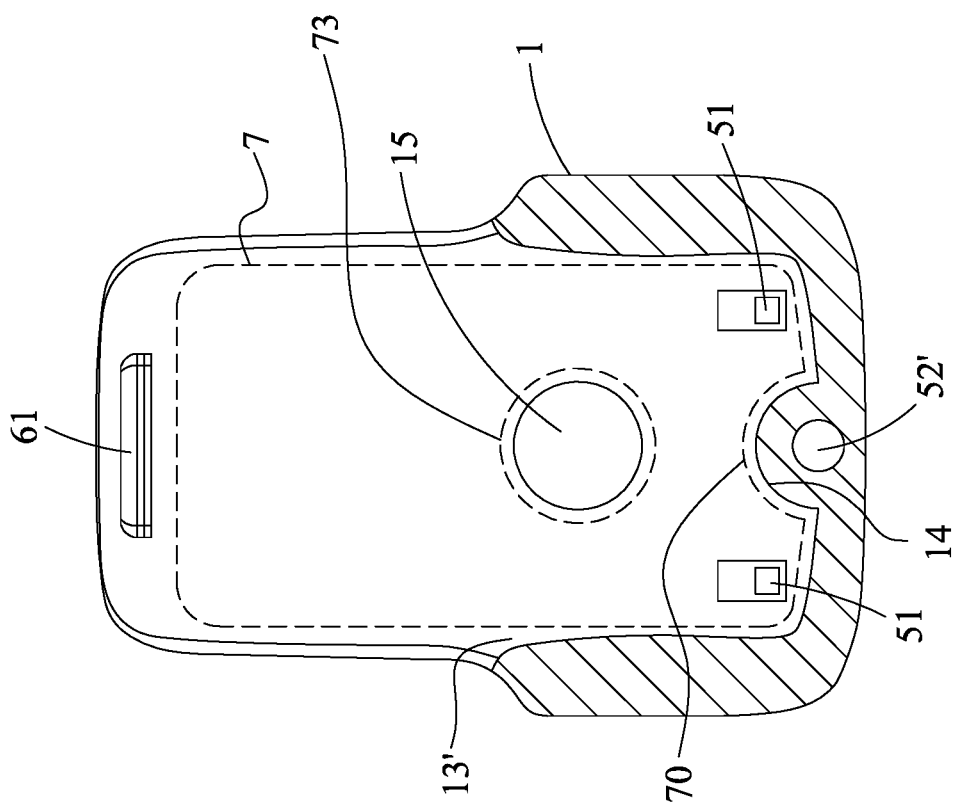

Please refer to FIG. 8A to FIG. 9B. The numerals of the components shown therein comply with those shown in FIG. 2 and other drawings. The same components as shown in the drawings and their movements are not repeatedly described here. Please refer to FIG. 8A and FIG. 9A, both of which show the top cross-sectional views of the charging module of the present invention with a transmitter 7 placed on the placing portion 13, and the second matching portion 70 is matched with the first matching portion 14, so that the transmitter 7 is in a correct relative position or a predetermined position, and the first electrical connection port 73 is now aligned to the opening 15. When the charging seat 30 (referring to FIG. 6A) is lifted up, it can be correctly electrically connected to the first electrical connection port 73. Referring to FIGS. 8A and 8B, the position of the actuating end 51 in the transverse direction is roughly equal to the position of the first matching portion 14. Therefore, only when the transmitter 7 reaches the end of the stroke, the actuating end 51 can be pressed down to make the first locking module 5 rotate without stopping the blocked portion 43 (referring to FIG. 5A), and the actuation end 51 is arranged at the end of the bearing surface 13' to reduce the friction with the bottom of the transmitter 7. In another embodiment, the actuating end 51 is not limited to be located at any other position. Furthermore, because the first matching portion 14 is a protruding structure that extends inward the placing portion 13 (as shown in FIG. 1F), therefore, two groove areas are naturally formed on both sides of the first matching portion 14, and the actuating end 51 is arranged in the groove area. Relatively, the second matching portion 70 of the transmitter 7 is an inwardly formed groove structure, and therefore two protruding structures are formed on both sides of the second matching portion 70. Accordingly, when the second matching portion 70 is matched with the first matching portion 14, the two protruding structures on both sides of the second matching portion 70 will go into the respective groove areas, and thereby the protruding structures will trigger the actuating end 51 so that the stopping end 52 is tilted up and no longer blocks the blocked portion 43. At this moment, the baffle 61 can extend from the baffle exit 16 to block the bottom surface of the tail end of the transmitter 7 to achieve the effect of locking transmitter 7. In FIG. 8B, when the transmitter is inserted into the charger 1 in an incorrect direction, e.g. when the tail end of the transmitter 7 goes into the placing portion 13, because it is blocked by the first matching portion 14, the front end of the transmitter 7 is pressed down above the baffle 61 so that the baffle 61 cannot extend from the baffle exit 16, and the first electrical connection port 73 is not aligned with the opening 15. Meanwhile, because the tail end of the transmitter 7 cannot reach the end of the insertion stroke so that the transmitter 7 cannot press down the actuating end 51, the stopping end 52 keeps on blocking the blocked portion 43. Therefore, the operating portion 40 cannot move, and the charging seat 30 cannot be exposed from the top surface of the opening 15, which prevents the first conductive connector 31 from abnormally colliding with the transmitter 7 and any possible damage, and thereby to prolong the lifetime of the charging device 1. That is to say, a safe state that prevents the first conductive connector 31 on the second electrical connection port 3' from colliding with the transmitter 7 can be maintained. At this moment, the second connecting end 42 still restricts the first connecting end 60 so that the baffle 61 cannot extend. When this phenomenon occurs, it can also serve as a reminder to the user that the transmitter 7 is placed in a wrong direction.

Figure 9A:
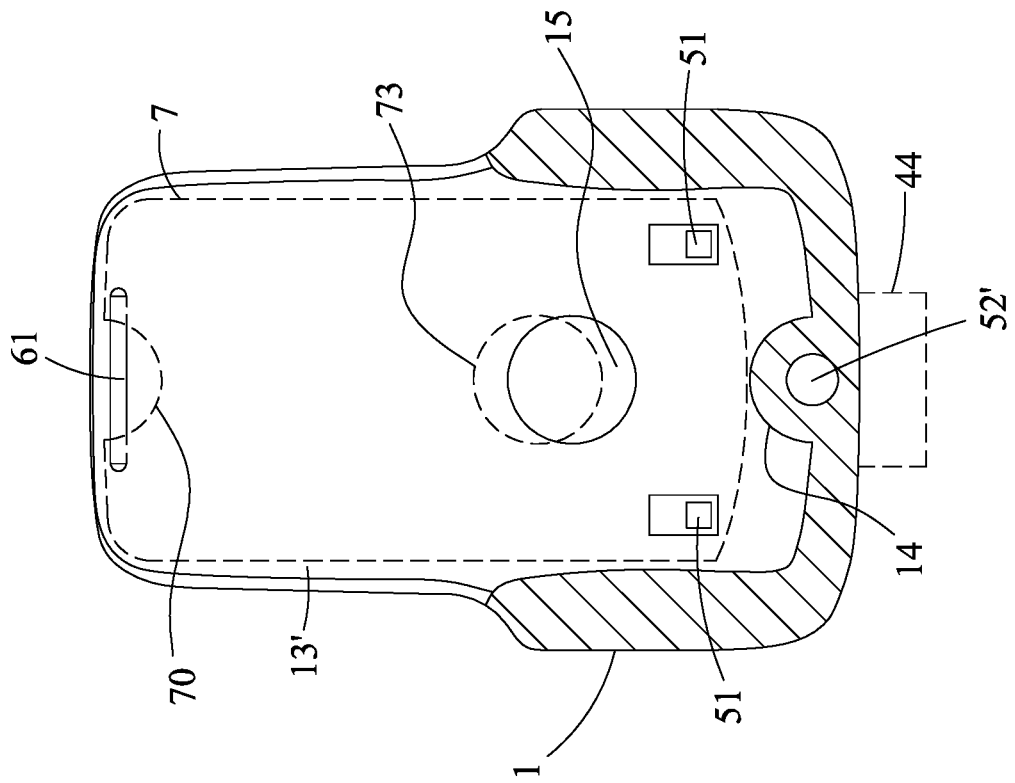
FIGS. 9A-9B each shows a top cross-sectional view of the charging device in use, having an actuating end, and installed thereon with a transmitter according to another embodiment of the present invention.
Figure 9B:
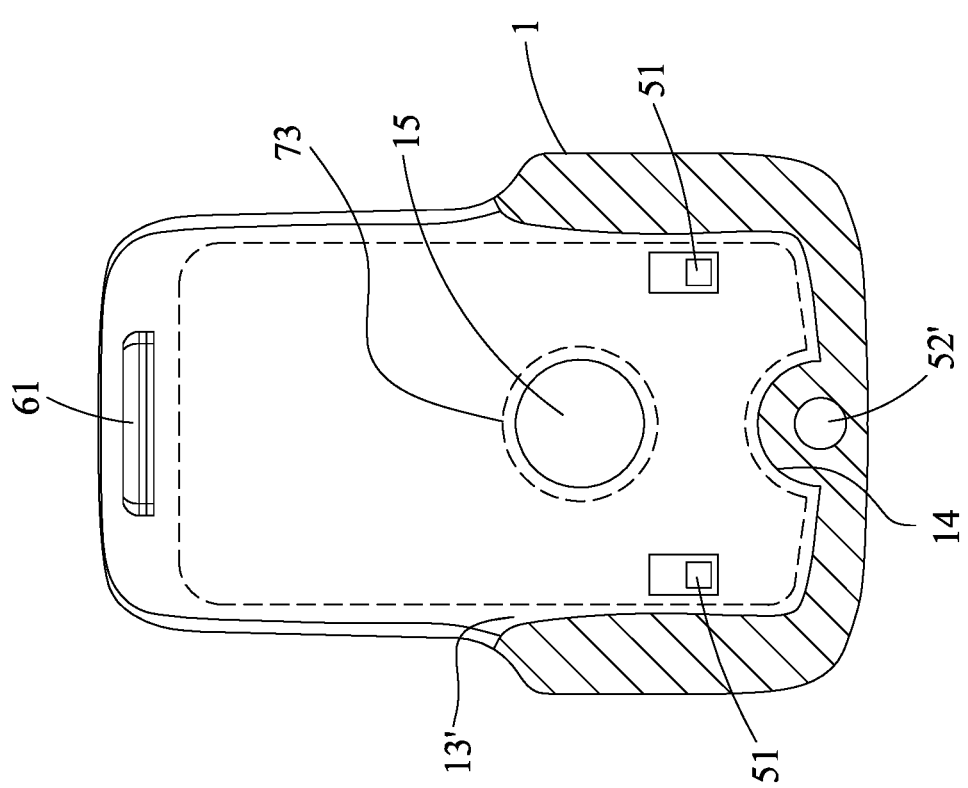

Please refer to FIGS. 9A and 9B. In comparison with FIGS. 8A and 8B, the actuating end 51 is arranged away from the groove area. During the placing procedure of the transmitter 7, the two protruding structures firstly press down the actuating end 51 so that the stopping end 52 is lifted up and no longer blocks the blocked portion 43, then the two protruding structures 2 go into the groove areas to be engaged with the first matching portion 14, and the baffle 61 can extend from the baffle exit 16 to block the tail end of the transmitter 7. In FIG. 9B, when the transmitter is inserted into the charger 1 in the incorrect direction, because the tail end of the transmitter 7 goes into the placing portion 13, the bottom of the front end of the transmitter 7 is pressed down above the baffle 61 so that the baffle 61 cannot extend from the baffle exit 16, and the first electrical connection port 73 is not aligned with the opening 15. Meanwhile, although the transmitter 7 can trigger the actuating end 51 and cause the stopping end 52 to tilt up and no longer block the blocked portion 43, however, the movable distance of the operating portion 40 is controlled so that at least the first conductive connector 31 cannot be exposed from the top surface of the opening 15, which thereby prevents the bottom of the transmitter 7 and the first conductive connector 31 from being damaged due to abnormal operation. At this moment, only a portion of the plug 44 can be pushed outwards. It can still serve as a reminder of an occurrence of a mistake to the user that the transmitter 7 is placed in an incorrect direction. That is to say, a safe state that prevents the first conductive connector 31 on the second electrical connection port 3' from colliding with the transmitter 7 can be maintained.

Figure 10:
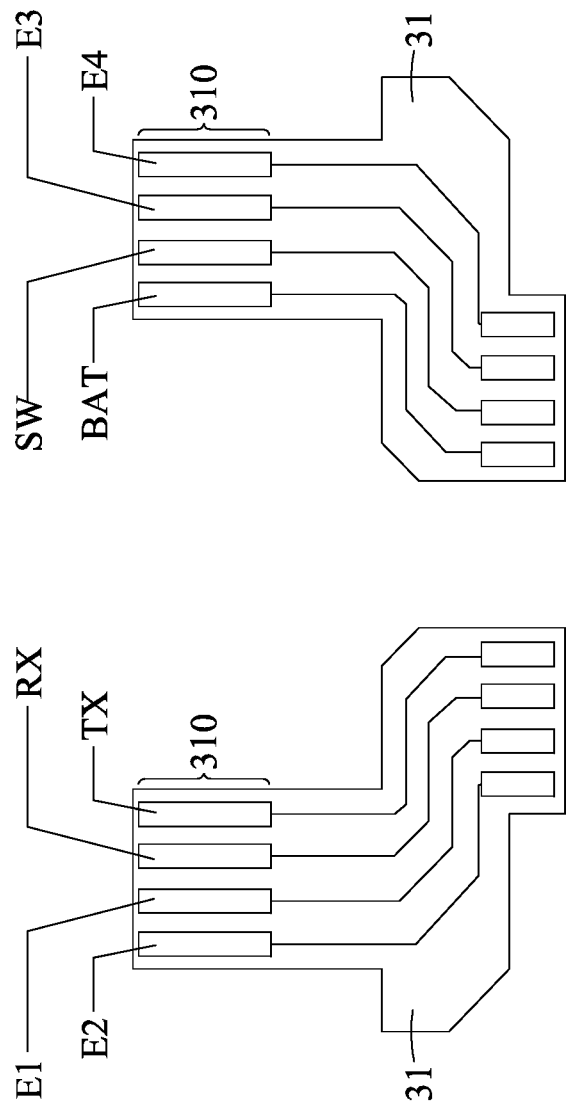
FIG. 10 shows a schematic drawing of the contacts of the first conductive connector of the present invention.
Figure 11:
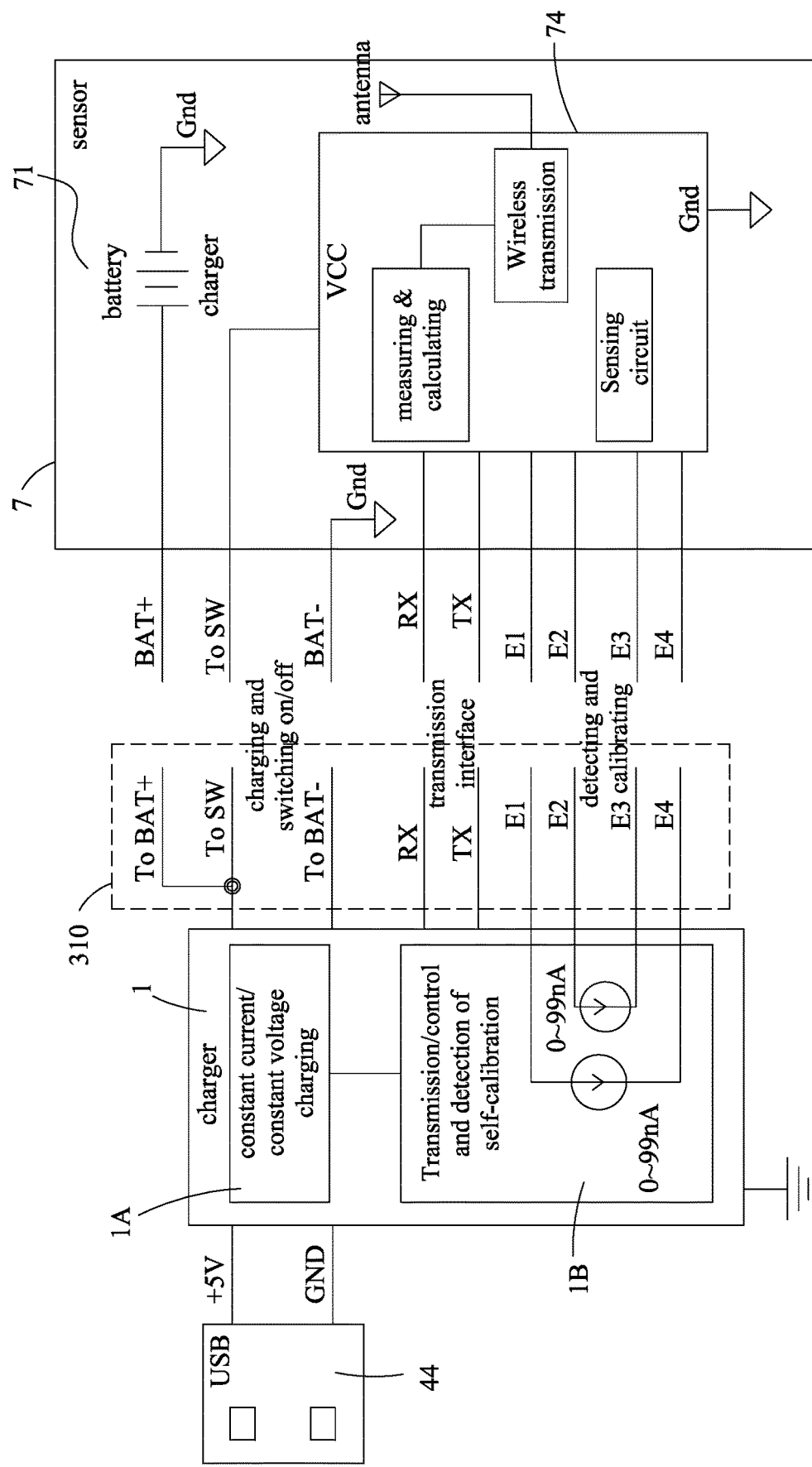
FIG. 11 shows a schematic drawing of the circuit of the charging device and the transmitter of the present invention.

Please further refer to FIG. 10. FIG. 10 shows a schematic drawing of the contact of the first conductive connector of the present invention. The first conductive connector 31 is presented as, but not limited to, a golden finger-shaped contact, and the contact terminal 310 of the first conductive connector 31 has a similar configuration as that of the output terminal 812 of the sensor (as shown in FIGS. 3B-3D). Therefore, both the contact terminal 310 and the output terminal 812 are adapted to be inserted into the insert hole 731 of the first electrical connection port 73 of the transmitter 7, so that the first conductive connector 31 can share the first electrical connecting port 73 with the output terminal 812 to save the internal space of the transmitter 7. Please further refer to FIG. 10 as well as FIG. 11. FIG. 11 shows a schematic circuit diagram of the charging device and the transmitter of the present invention, which discloses that the circuit assembly 33 in the charger 1 has a charging circuit group 1A and a calibrating circuit group 1B. The contact terminal 310 of the first conductive connector 31 is presented as, but is not limited to, 8 contacts: BAT, SW, RX, TX, E1, E2, E3 and E4, which number can be adjusted according to the number of contacts of the sensor output terminal 812. The charging circuit group 1A is electrically connected to the third electrical connection port 44 to input power. The charging circuit group 1A is used to provide and control a charging voltage, and the charging circuit group 1A then charges the transmitter 7 through the contact BAT, with the contact SW serving as a charging switch, by outputting the charging voltage to the transmitter 7. The remaining contacts are used to connect the calibration circuit group 1B of the charging device 1 and the transmitting module 74 of the transmitter 7 to facilitate the detection to the transmitter functions including data transmission, control and detection of self-calibration, leakage current measurement and/or resistance measurement. In another embodiment, the charging device 1 may only provide a charging function.

Figure 12A:
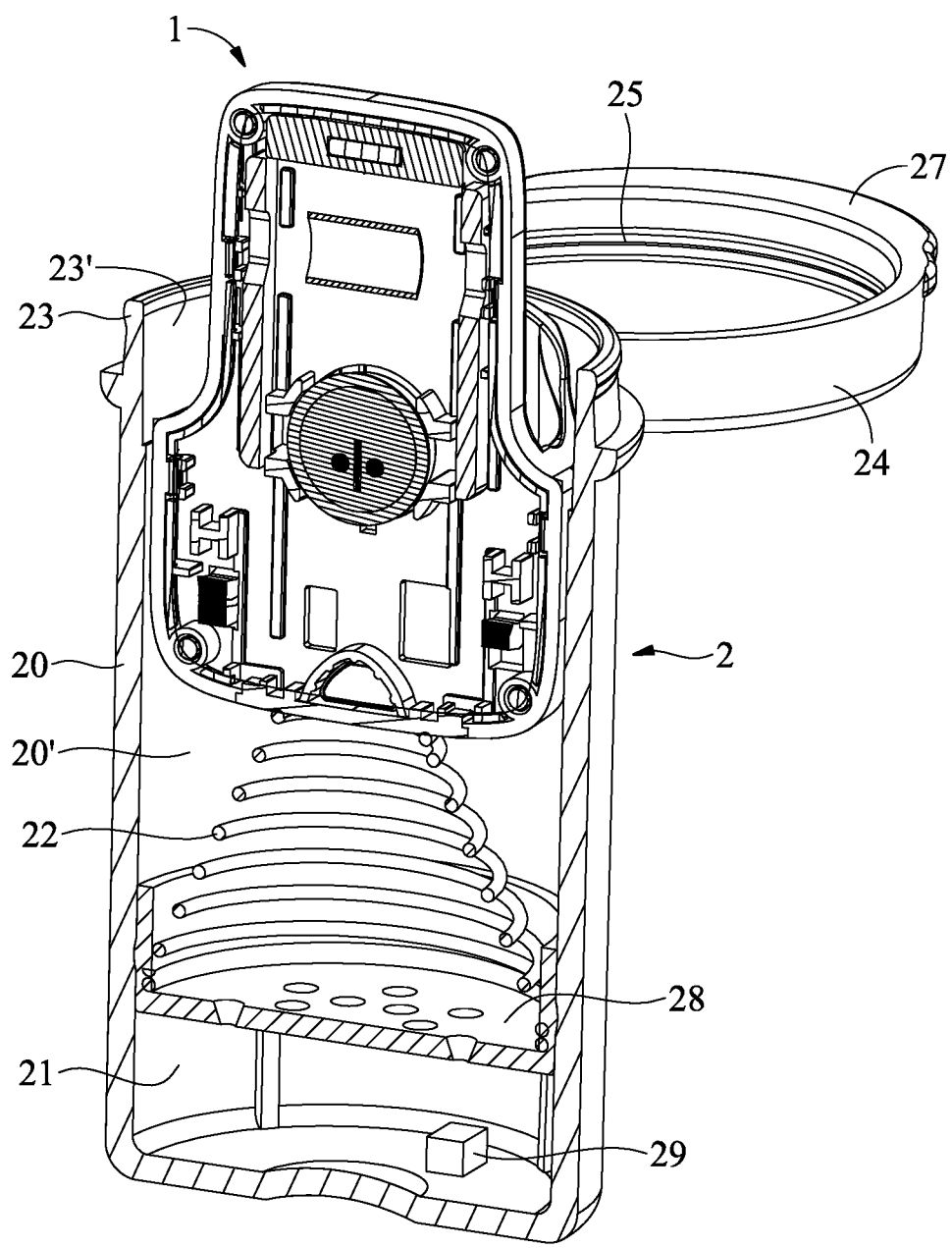
FIG. 12A shows a perspective cross-sectional view of the moisture-proof assembly of the charging device in use of the present invention.
Figure 12B:
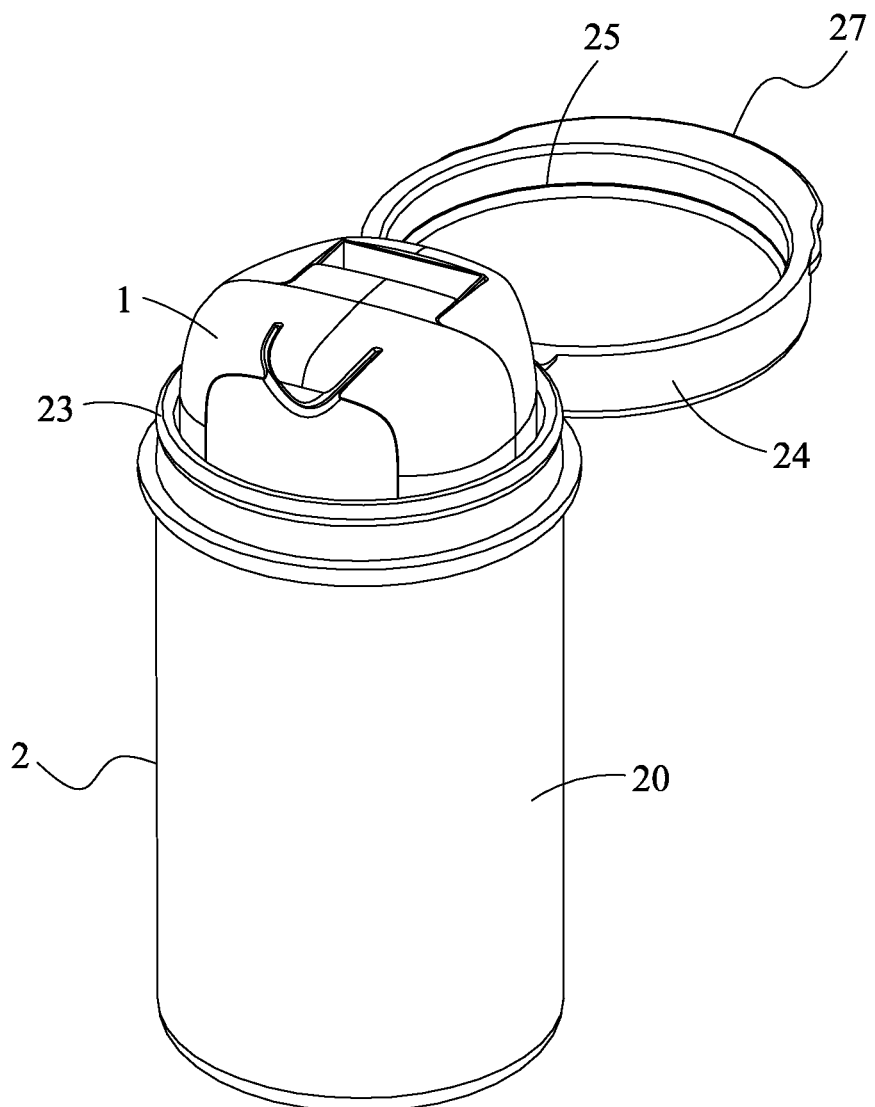
FIG. 12B shows a schematic drawing of the appearance of the moisture-proof assembly of the charging device in use of the present invention.
Figure 12C:
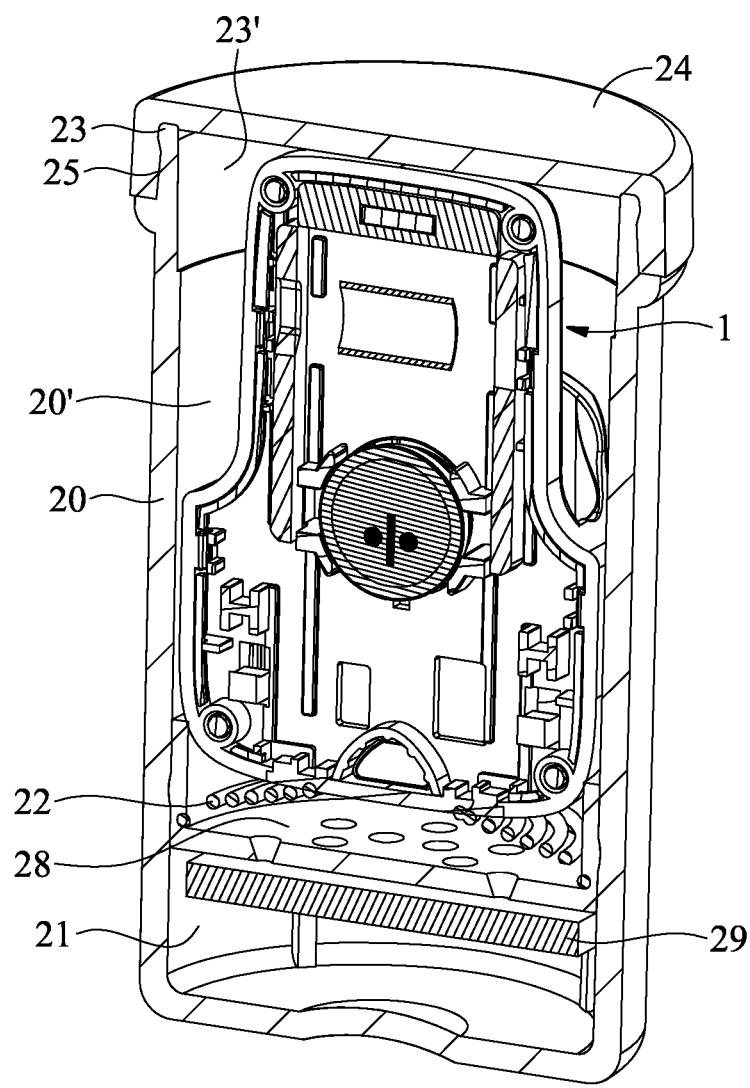
FIG. 12C shows a perspective cross-sectional view of the moisture-proof assembly of the charging device in use covered by a cover of the present invention.

Please refer to FIGS. 12A to 12F. FIG. 12A shows a moisture-proof assembly 2 having a housing 20 generally in the form of a can body, at least such as one of a cylindrical, elliptical cylindrical or oblate cylindrical cans, for accommodating the charging device 1 or the transmitter 7 or the charging device containing the transmitter 7 to form a moisture-proof assembly 2. The moisture-proof assembly 2 has an opening 23' and a first buckling edge 23 formed next to the opening 23'. The opening 23' has an opening direction perpendicular to the opening 23', and the protruding direction of the first buckling edge 23 is perpendicular to the opening direction. A cover 24 is movably arranged on the housing 20 and used to seal the opening 23'. A second buckling edge 25 is also formed inside the cover 24, and its protruding direction is opposite to that of the first buckling edge 23 to buckle the first buckling edge 25 and the second buckling edge 25 mutually. Furthermore, the housing 20 has an elastic element 22. When the charging device 1 is placed in the housing 20 and the cover 24 seals the opening 23', the charging device 1 is pressed down by the cover 24 and retracted into the housing 20, thereby the elastic element 22 is elastically deformed (please referring to FIG. 12C). When the cover 24 is opened, the elastic element 22 releases its elastic potential to push the charging device 1 outwards, so that at least a part of the charging device 1 is protruded from the housing for a user to take the charging device 1 out (as shown in FIG. 12B). When the transmitter 7 needs to be charged, the charging device 1 is taken out of the housing 20, so that an external power source can be used to connect and charge the transmitter 7. The elastic element 22 can be a compression spring, such as a conical spring, a coil spring, a spiral spring, etc., so that the elastic element 22 interferes with the charging device 1, and thus can also fix the position of the accessory (e.g. the charging device 1 or the transmitter 7) placed in the housing 2 to prevent from shaking. As shown in FIG. 12C, a conical spring is used. Because the diameters of the coils from the top to the bottom of the conical spring are significantly increased, when the cover 24 seals the opening 23' as shown in FIG. 12C, the charging device 1 is pressed down into the housing 20, and the charging device 1 further compresses the elastic element 22, the upper coils can be pressed down inside the lower coils. Accordingly, this kind of spring can be compressed to a shorter length than the cylindrical coil spring, and has the advantage of a reduced volume of the moisture-proof assembly. When the charging device is in the inserted state, the spring compression height $H_{compress}$ plus the length H1 of the charging device is less than the housing height H2. When the charging device is not in the inserted state, the spring extension height $H_{extend}$ plus the length H1 of the charging device is larger than the housing height H2. Please continue to refer to FIGS. 12A and 12C, wherein the housing 20 is further divided into a first accommodating space 20' and a second accommodating space 21. The first accommodating space 20' is used to store the charging device 1, the second accommodating space 21 is used to contain the desiccant 29, and there is a hole structure 28 between them, so that the moisture in the first accommodating space 20' can pass through the hole structure 28 to the second accommodating space 21, and the moisture can be absorbed by the desiccant 29, to prevent the transmitter 7 from getting wet. The transmitter 7 disclosed according to the first embodiment is approximately 32.8 mm*19.8 mm*4.15 mm (+/−0.5 mm), the size of the charging device 1 is approximately 40*26*23 mm (+/−0.5 mm), and the transmitter is installed on the charging device. The volume of the moisture-proof assembly 2 is no more than 200 cubic centimeters, or between 12 and 138 cubic centimeters, or between 30 and 70 cubic centimeters, or multiply the length by the width to control from 3 to 28 centimeters. The diameter range of the moisture-proof assembly 2 is designed to be 2 to 5 cm, and its height is designed to be 4 to 7 cm, so that the volume of the moisture-proof component is miniaturized and convenient for users to carry.

Figure 12D:
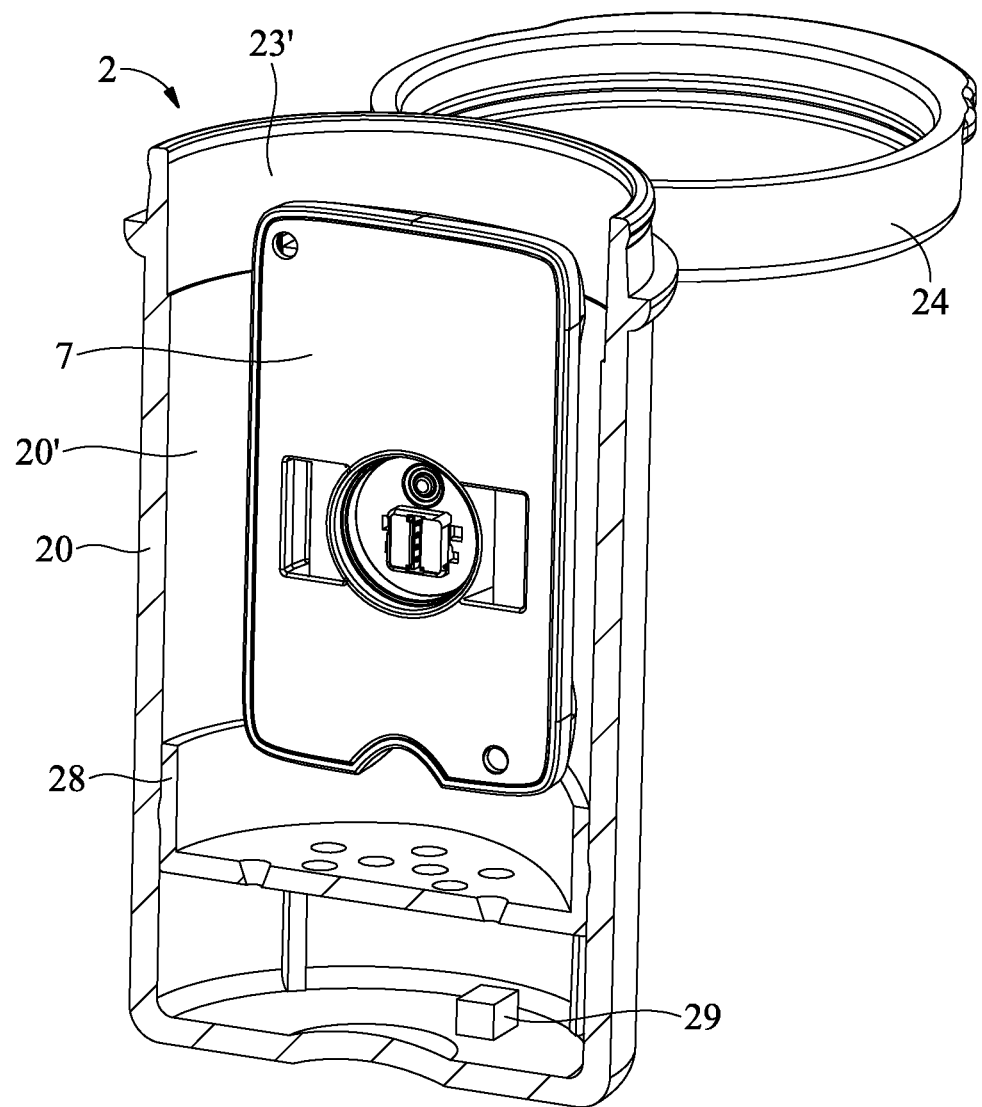
FIG. 12D shows a perspective cross-sectional view of the moisture-proof assembly of the charging device in use according to another embodiment of the present invention.
Figure 12E:
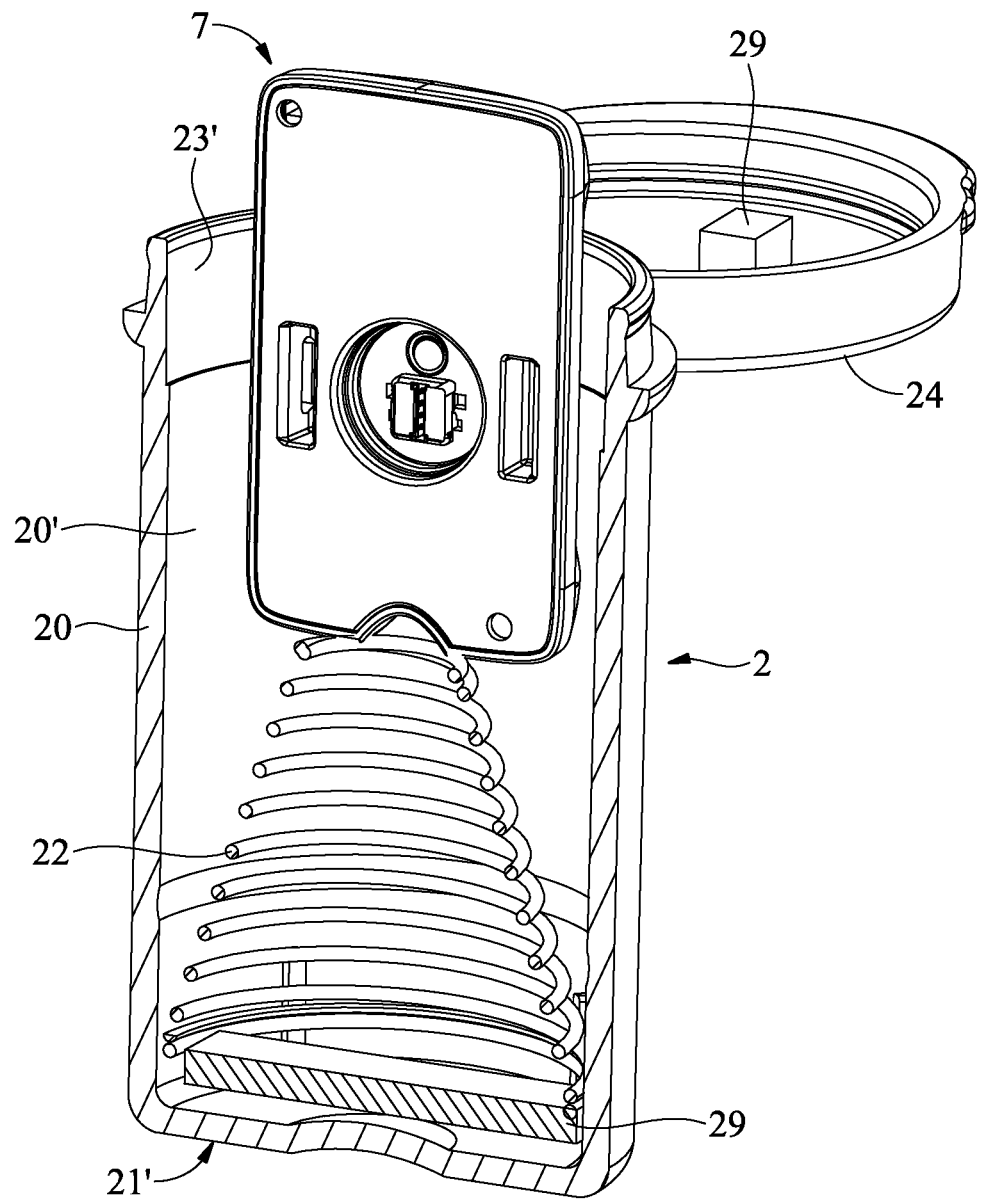
FIG. 12E shows a perspective cross-sectional view of the moisture-proof assembly of the charging device in use according to another embodiment the present invention.
Figure 12F:
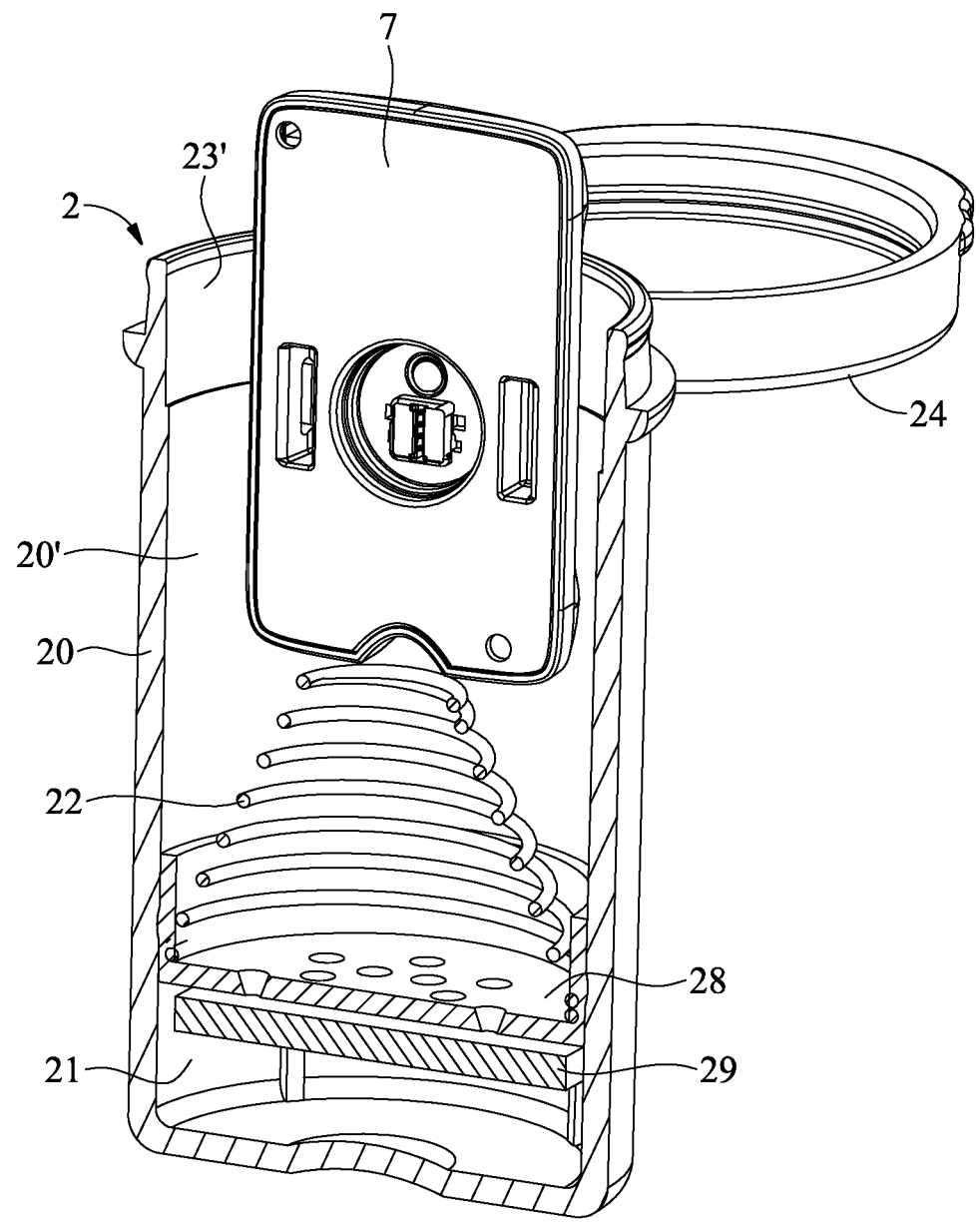
FIG. 12F shows a perspective cross-sectional view of the moisture-proof assembly of the charging device in use according to another embodiment the present invention.

Please referring to FIGS. 12D to 12F, which disclose that the transmitter 7 is placed in the moisture-proof assembly 2 according other embodiments of the present disclosure. FIG. 12D discloses a state in which only the transmitter 7 is placed in the moisture-proof assembly 2 having the hole structure 28. The desiccant 29 is also disposed in the housing 20, such as the bottom. In FIG. 12E, it is revealed that the elastic element 22 is directly disposed on the bottom of the housing 20, and the desiccant 29 is also disposed in the housing 20. In addition, the desiccant 29 can also be selectively disposed on the inner surface of the cover 24. When the housing 20 is opened, the desiccant 29 will face outwards for easy replacement. As for FIG. 12F, it reveals the state where only the transmitter 7 is placed in the moisture-proof assembly 2 having the hole structure 28. In another embodiment, the desiccant 29 may be integrally formed in the housing or the inner wall, so that the housing 20 does not need to distinguish different accommodation spaces (not shown in the figure). In addition, the pushed portion 27 facilitates the user to open the cover 24. The moisture-proof assembly 2 can be used to properly protect the charging device 1 when it is not in use and isolate it from outside moisture, and further use the internal desiccant to dehumidify the transmitter 7 and/or the charging device 1 to extend the service life, which can prevent moisture from damaging electronic parts. The housing 20 can also be provided with a structure similar to the observation area 21'. The observation area is a part of the housing 20, and is made by injection molded from transparent or translucent materials. If a desiccant that can absorbs moisture to change color or an additional desiccant indicator is used, it is easy to check the moisture status of the transmitter 7 and/or the charging device 1.

The method of using the moisture-proof assembly 2 is to provide the user with a first transmitter and a second transmitter at the same time, wherein the first moisture-proof assembly includes a first transmitter and a moisture-proof assembly 2, the second moisture-proof assembly includes a second transmitter combined with a charging device, and the second moisture-proof assembly is disposed in the moisture-proof assembly 2. The user will firstly use the first transmitter for measurement. When the power of the first transmitter is low enough to a lower limit, it is removed from the sensor pedestal, and the second transmitter and the charging device 1 are taken out from the moisture-proof assembly 2. The second transmitter is used to install to the sensor pedestal, and the first transmitter is put into the placing portion 13 of the charging device 2 to be charged. After said charging is completed, the first transmitter and the charging device are assembled to return to the moisture-proof assembly 2 for storage, so that the first transmitter and the second transmitter can be charged and used alternately. The moisture-proof assembly 2 used for the first transmitter is in any form of container.

Figure 13A:
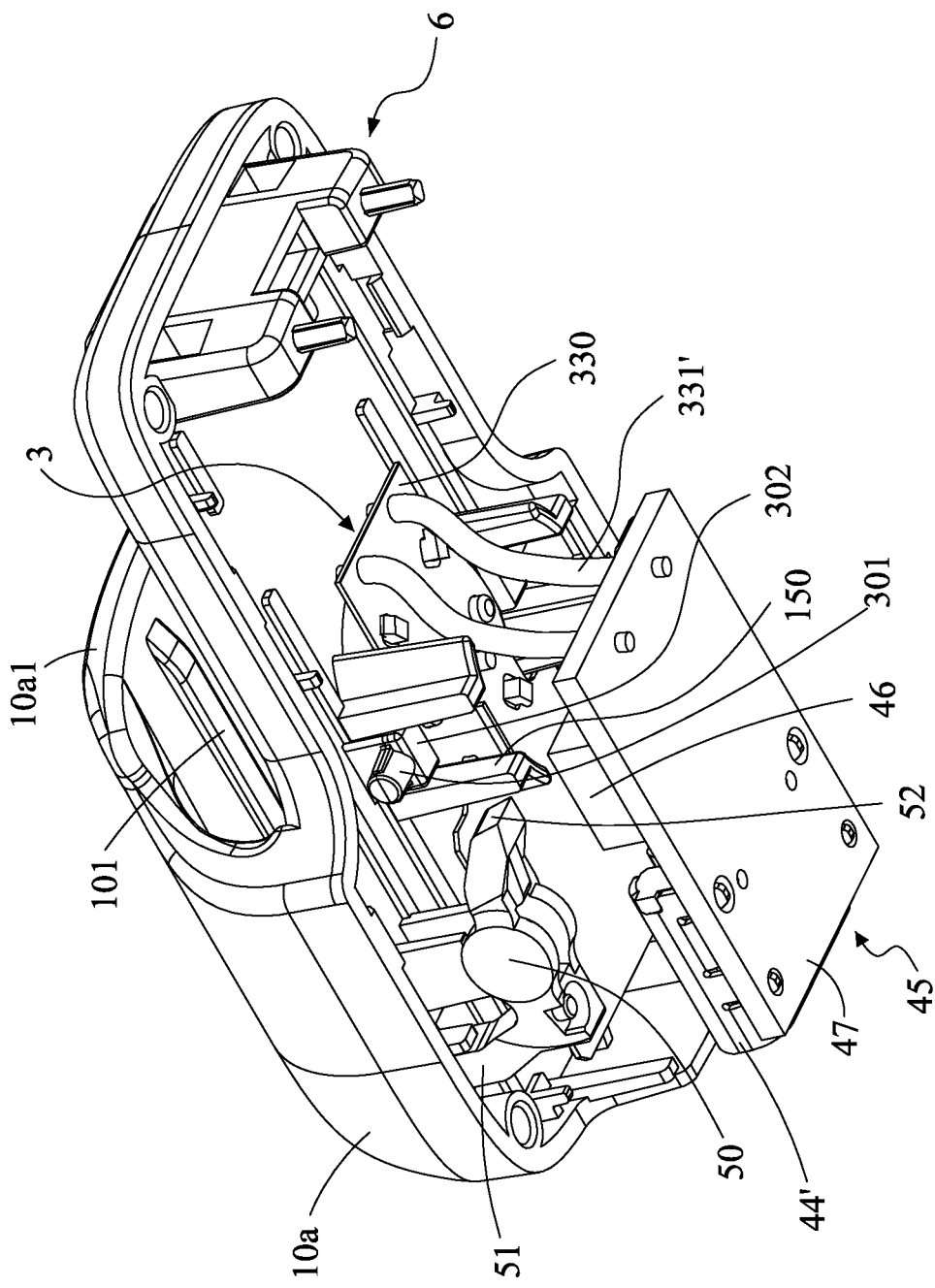
FIGS. 13A-13B shows a hollow perspective view of different embodiments of the third electrical connecting port of the charging device of the present invention.
Figure 13B:
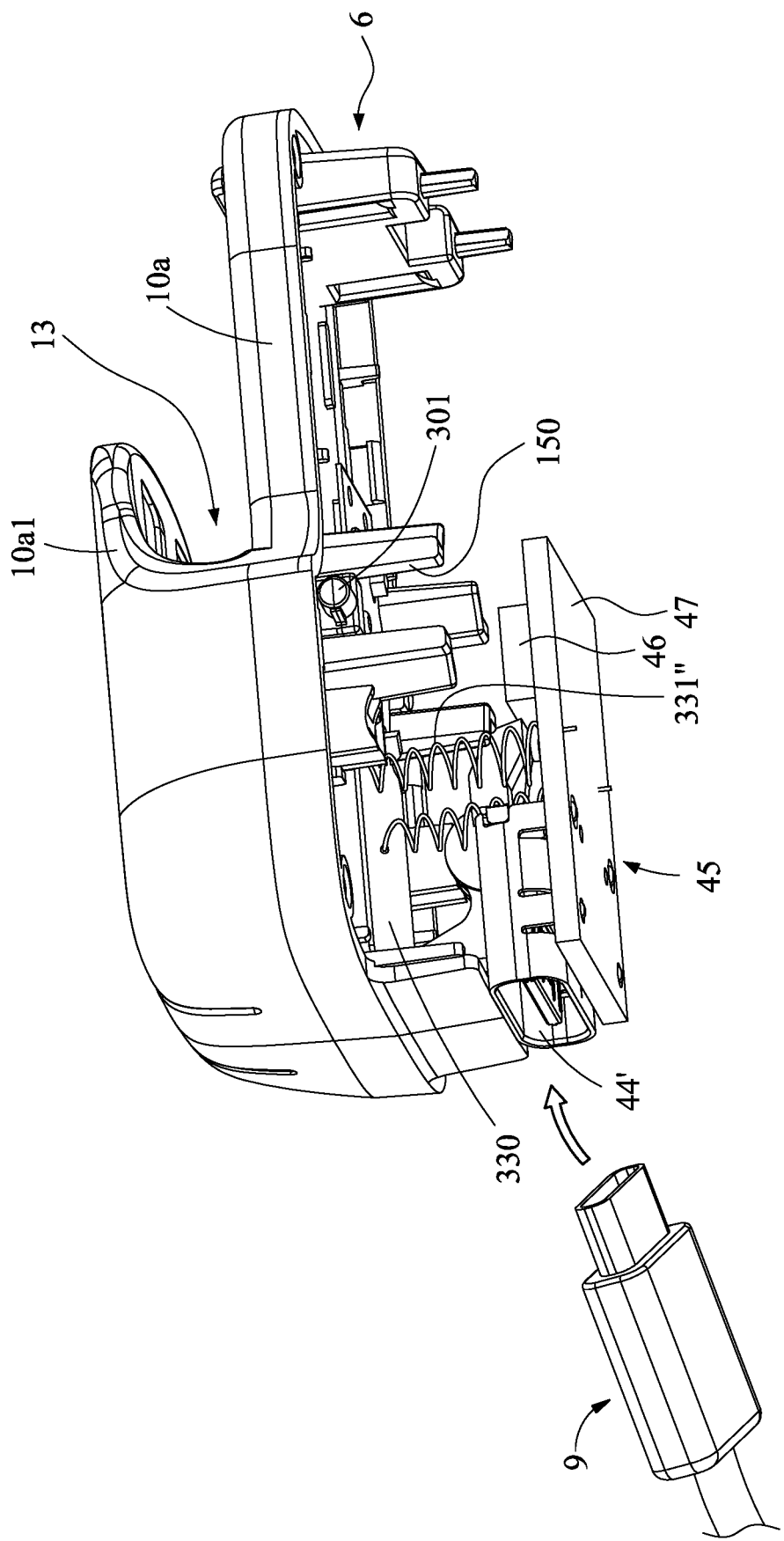

Please refer to FIG. 13A, which is another embodiment of the charging device of the present invention, and please also refer to FIG. 2. The difference from the previous embodiments is that the charging device 1 electrically connects the third electrical connecting port (USB socket 44') and the circuit board 330 of the second connecting port 3' to each other through a wire 331'. The wire 331' also has a certain flexibility to adapt to the lifting of the charging module 3 for bending. In addition, FIG. 13A differs from the previous embodiment in that: the third electrical connecting port uses a USB socket 44' instead of the electrical connecting plug 44 (USB plug), and it also forms a power storage unit 45 by combining a rechargeable battery 46 and a power circuit board 47. The power storage unit 45 is electrically connected to the charging module 3 to input power to charge the transmitter 7. In addition, the user can also connect the USB socket 44' to an external power source to recharge the rechargeable battery 46 to increase the ease of use. In another embodiment, the power storage unit 45 can omit the USB socket and be equipped with disposable batteries, such as dry batteries and button batteries commonly available in the market. In another embodiment, the rechargeable battery 46 can also be omitted, and the USB socket 44' is connected to an external power source 9 (FIG. 13B, and symbols 91, 92, 93 in FIG. 6E) to supply power for charging the transmitter 7. As for the operating portion 40 of the operating module 4 shown in FIG. 2, although it is not disclosed in FIG. 13A, it is still used in this embodiment. However, it is not shown in this figure because it is covered by the power storage unit 45, and the connection relationship and driven linkage between the operating portion 40 and the second electrical connecting port 3' of the charging module 3 are mainly through the coupling between the first guiding structure 41 and the second guiding structure 301, and the action relationship between the two is the same as before. However, the difference from the previous embodiment is that the operating portion 40 in FIGS. 13A and 13B is not fixed to the USB socket 44' (third electrical connecting port). On the contrary, the USB socket 44' is only fixed in the charging device 1. The jack of the socket 44' is exposed, therefore when the push-pull key 12 is operated, only the second guiding structure 301 is driven by the first guiding structure 41, and the USB socket 44' does not move. Please refer to the previous drawings and descriptions for the efficacies of other components in FIG. 13A, and will not be repeated here.

Please refer to FIG. 13B, which is another embodiment of the charging device of the present invention. Please also refer to FIG. 2. The biggest difference between the embodiment in FIGS. 13B and 13A is that the power storage unit 45 is electrically connected to the power circuit board 47 to the circuit board 330 for the charging seat 30 through a coiled wire 331". Basically, the displacement of the charging device 1 with the push-pull button 12 (not shown in FIG. 13B) drives the lifting of the charging seat 30 and the circuit board 330 of the second electrical connecting port 3', thereby indirectly drives the expansion and contraction of the coiled wire 331. In another embodiment, the coiled wire 331" can also be replaced by a spring connector (POGO pin). As for the efficacies of other components, please refer to the previous drawings and descriptions, it is not repeated here. In FIGS. 13A and 13B, the USB socket 44' being as the third electrical connecting port is designed without moving back and forth.

Figure 14A:
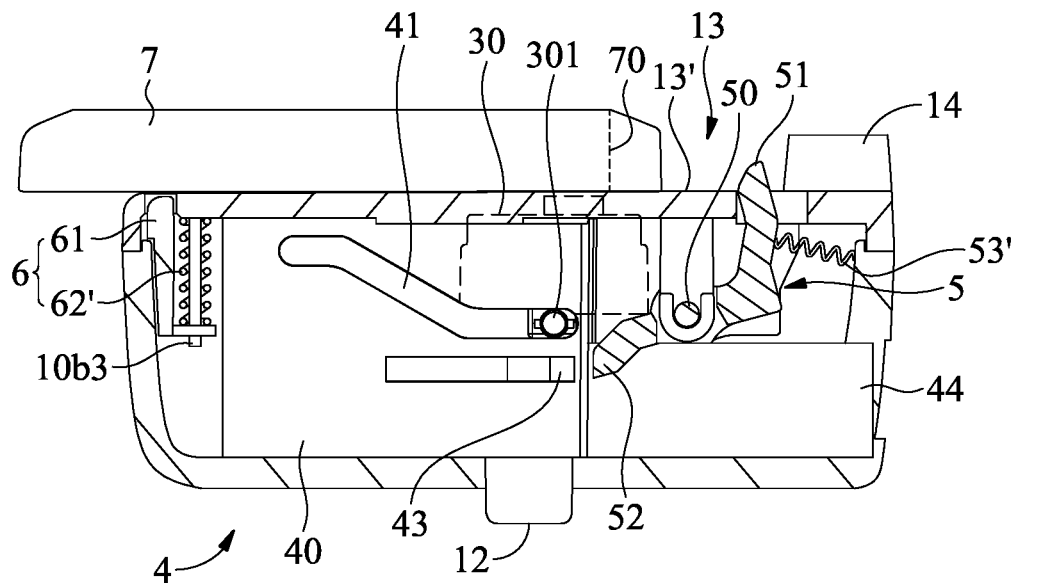
FIGS. 14A-14B shows a side view of a hollowed-out view of another embodiment of the charging device of the present invention.
Figure 14B:
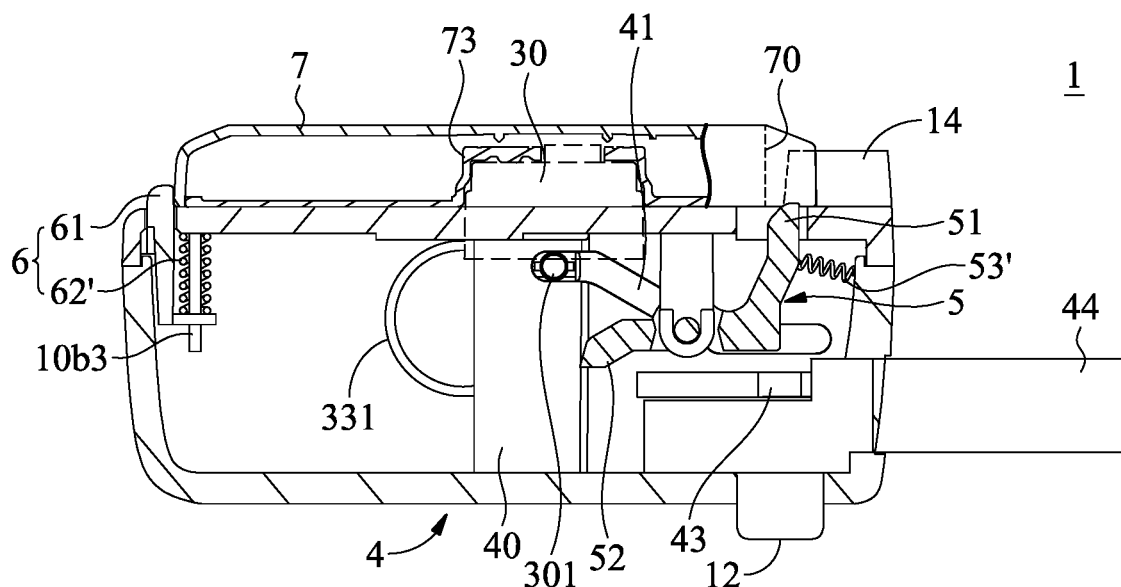

Please refer to FIGS. 14A and 14B, another embodiment of the charging device is disclosed. The charging device 1 includes a placing portion 13 for placing the transmitter 7, the placing portion 13 also includes a bearing surface 13' for placing the transmitter 7, and the bearing surface 13' includes an opening 15 (FIG. 4A). A charging module 3 is provided on the opposite side of the bearing surface 13', and includes a second electrical connecting port 3', a circuit assembly 33, and a third electrical connecting port 44. The second electrical connecting port 3' is arranged at an opening 15 (see FIG. 4A) for electrical connecting with the first electrical connecting port 73 (see FIG. 3D), and the third electrical connecting port 44 is used for connecting an external or internal power source (see the symbols 91, 92, 93 in FIG. 6E or the symbol 46 in FIG. 13B). The circuit assembly 33 (please refer to FIG. 2) is connected between the second electrical connecting port 3' and the third electrical connecting port 44 to perform charging and charging control for the physiological signal transmitter 7. The opposite side of the bearing surface 13' is also provided with a control module to control the safe operation between the transmitter 7 and the charging module 3. The control module includes an operating portion 40 for driving the second electrical connecting port 3' to connect to the first electrical connecting port 73. A first locking module 5 is also provided on the opposite side of the bearing surface 13', can releasably restrict the electrical connection between the second electrical connecting port 3' and the first electrical connecting port 73, or is used to further restrict the displacement of the second electrical connecting port 3'. For the detailed operation of the first locking module 5, please refer to FIGS. 4B, 5A, and 6B, which will not be repeated here. Please refer to FIGS. 14A and 14B, the bearing surface 13' is provided with a second locking module 61 at the other end relative to the indicating area 11, and the second locking module 61 can be extended and contracted on the bearing surface 13' to fix the position of the transmitter 7. Further, the second locking module 6 includes a baffle 61, which is sleeved on a guide rod 10b3 to be able to move up and down, connected to the bottom of the bearing surface 13' by a spring 62', and the elasticity provided by a spring 62 keeps the baffle 61 normally protruding from the bearing surface 13'. Please also refer to FIGS. 14A to 14B. When the transmitter 7 is deposited on the bearing surface 13', the transmitter 7 will first press and retract the baffle 61 into the bearing surface 13' during the depositing process. After the first and second matching portions 14, 70 are matched, the transmitter 7 just leaves the top of the baffle 61 without blocking it. At this time, the baffle 61 is forced by the elastic restoring force of the spring 62' and protrudes on the bearing surface 13' again. When the transmitter 7 is to be taken out, the push-pull button 12 is firstly pushed to the left to lower the charging seat 30 to release the electrical connection, and then the baffle 61 is pressed below the bearing surface 13', so that it no longer blocks the transmitter 7 at the tail portion, and the transmitter 7 can be translated to the left away from the bearing surface 13'. The features of the second locking module 6 shown in FIGS. 14A and 14B can also be applied to other embodiments of the charging device of the present invention. As shown in FIG. 1A, the baffle 61 retracted below the bearing surface 13' can be regarded as being pressed by the user to facilitate the insertion of the transmitter 7 into the placing portion 13. The user can also directly press the baffle 61 through the transmitter 7 as shown in FIG. 14A. During the depositing process, if the second matching portion 70 is correctly inserted into the placing portion 13 inward so that it fits with the first matching portion 11 to achieve the result that the transmitter 7 is in the correct relative position, the baffle 61 will be no longer blocked by the transmitter 7 but can be pushed by the restoring force of the elastic element 62 (FIGS. 2 and 5B) to protrude from the bearing surface 13' again because the transmitter 7 has reached the correct position that is not so deep. It can be seen that if the baffle 61 shown in FIGS. 14A and 14B is used, the first engagement end 60 of the second locking module 6 and the second engagement end 42 of the operating portion 40 can be eliminated and not provided.

Figure 15:
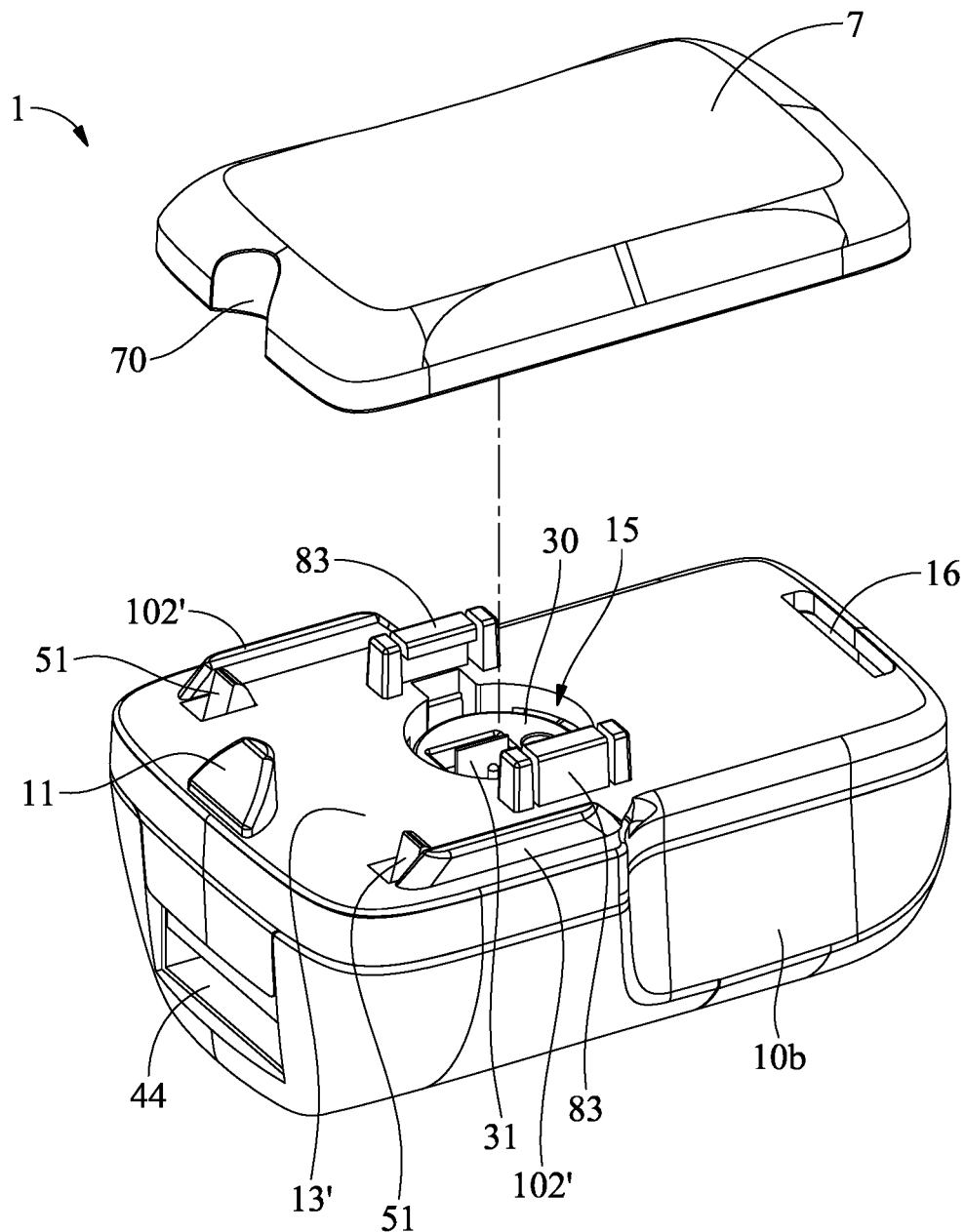
FIG. 15 shows a perspective schematic view of another embodiment of the charging device of the present invention.

Please refer to FIG. 15, which discloses an embodiment without a cover plate 10a1. Therefore, the bearing surface 13' itself serves as a placing portion, and an indicator area 11 is provided at one end of the bearing surface 13' as a first fitting portion that can provide a visual cue effect so that the user can connect, fit, and join the second matching portion 70 with the placing portion. The actuating end 51 (FIGS. 1D, 1F, 2, and 4B) of the first locking module 5 (FIGS. 2 and 4B) also protrudes on the bearing surface 13'. In addition, a baffle exit 16 is provided at the other end of the bearing surface 13', in which the baffle 61 (FIGS. 2, 4C and 5C) is located. Since there is no cover plate 10a1 in this embodiment, in order to prevent the transmitter 7 from detaching upward (that is, the axial direction of the bearing surface 13'), the bearing surface 13' is further provided with the second buckle structure 83 on the pedestal 80 as shown in FIG. 3D. The second buckle structure 83 is used to generate a buckling effect with the first buckle structure 72 of the transmitter 7, and enables the transmitter 7 to be fixed on the bearing surface 13'. In addition, in order to make the transmitter 7 more stable on the bearing surface 13' without falling off due to accidental impact, side walls 102' are formed on the bearing surface 13', which are usually arranged in pairs. That is, on both sides of the bearing surface 13 ', when the transmitter 7 is fixed on the bearing surface 13', the side walls 102' are attached to the two sides of the transmitter 7, so as to assist in fixing the transmitter 7 in the lateral direction. As for the efficacies of other components, please refer to the previous drawings and descriptions, which will not be repeated here.

Figure 16A:
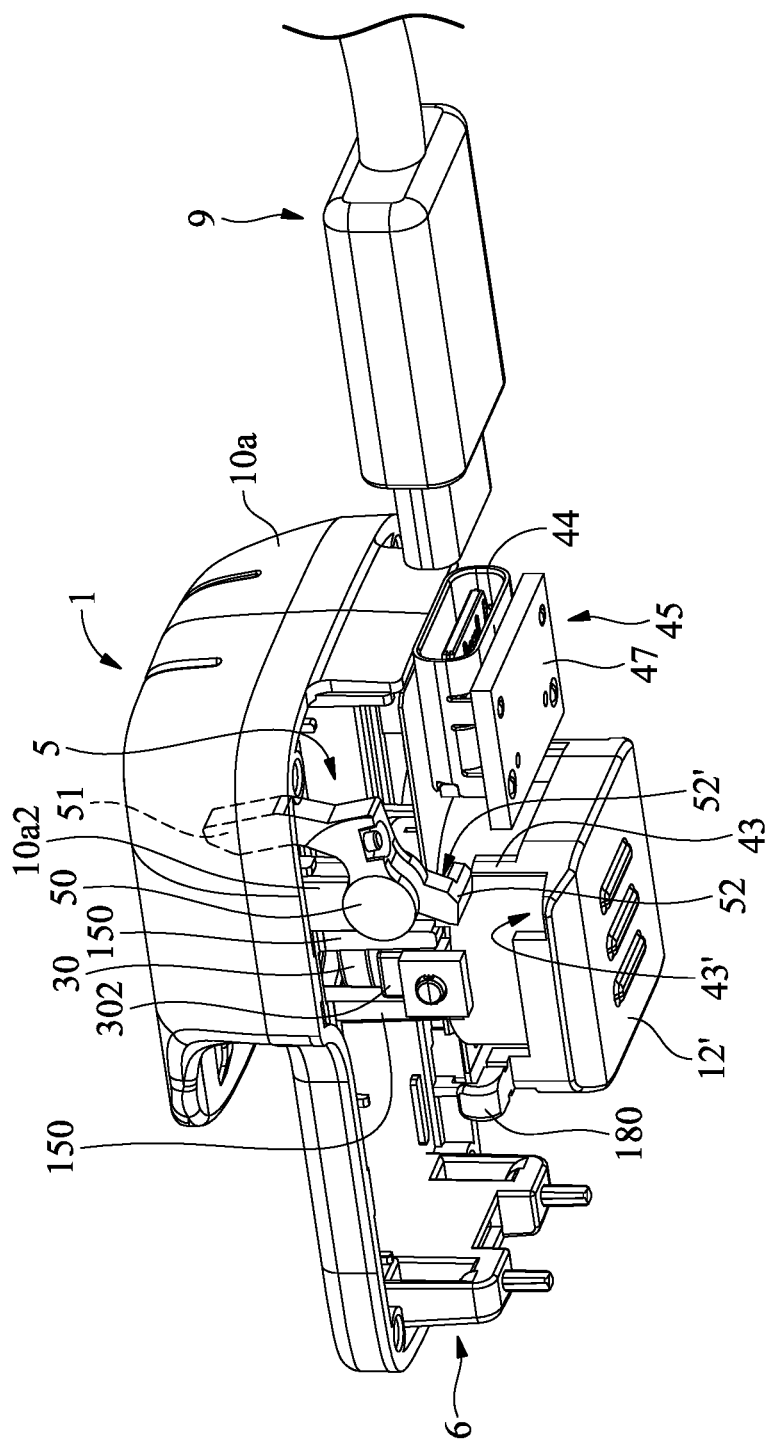
FIGS. 16A-16B shows a perspective view of another embodiment of the charging device of the present invention with a hollowed-out front and lower side.
Figure 16B:
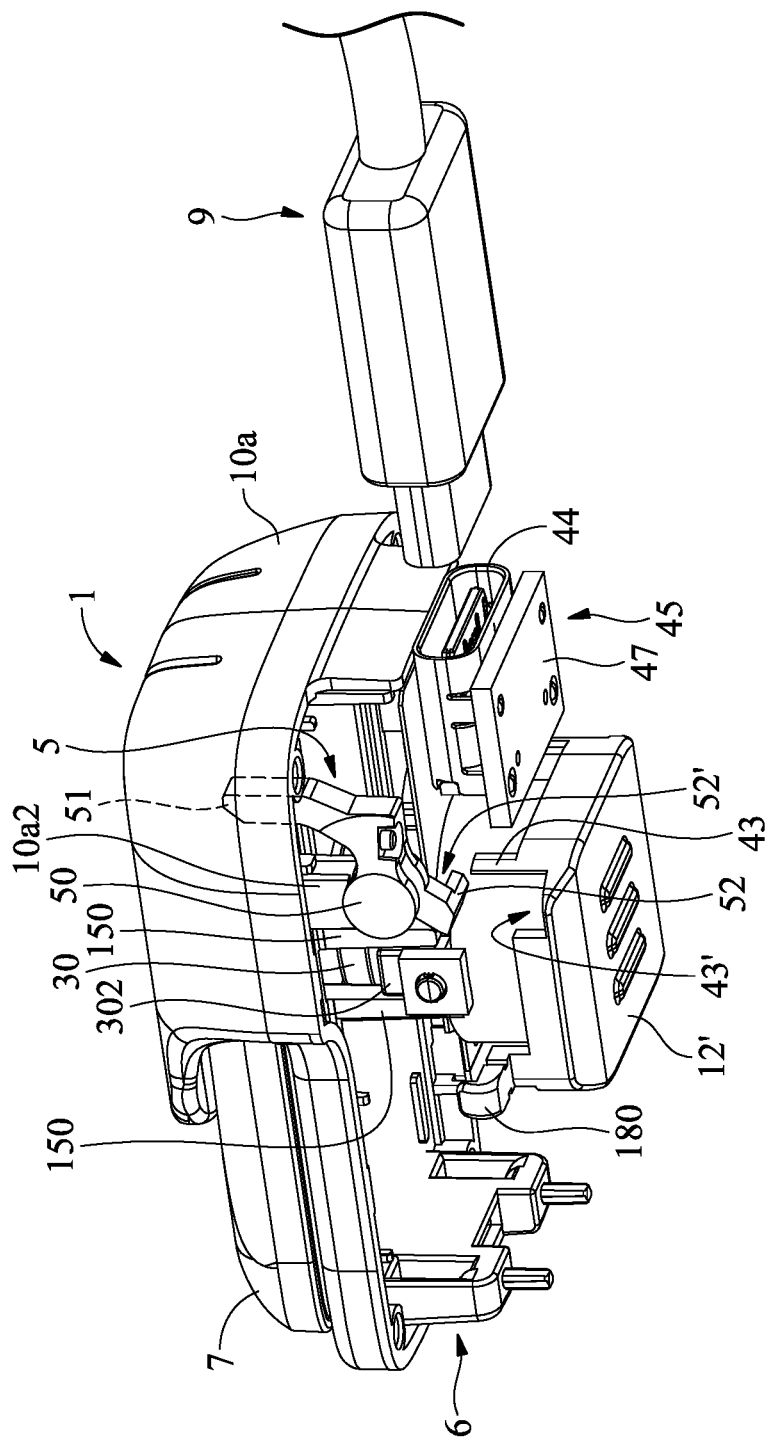
Figure 16C:
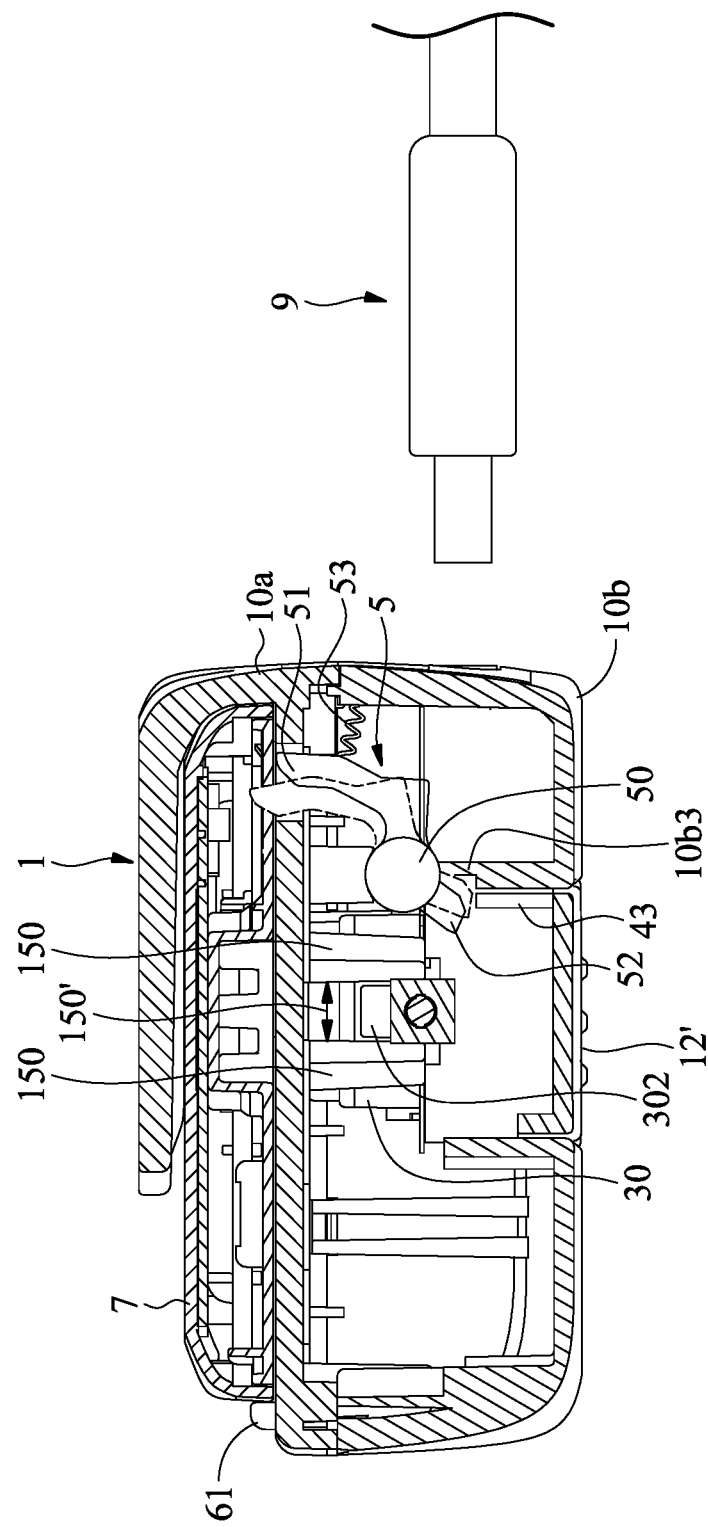
FIG. 16C shows a schematic diagram of the side cross-sectional action of the embodiment of FIGS. 16A-16B.
Figure 16D:
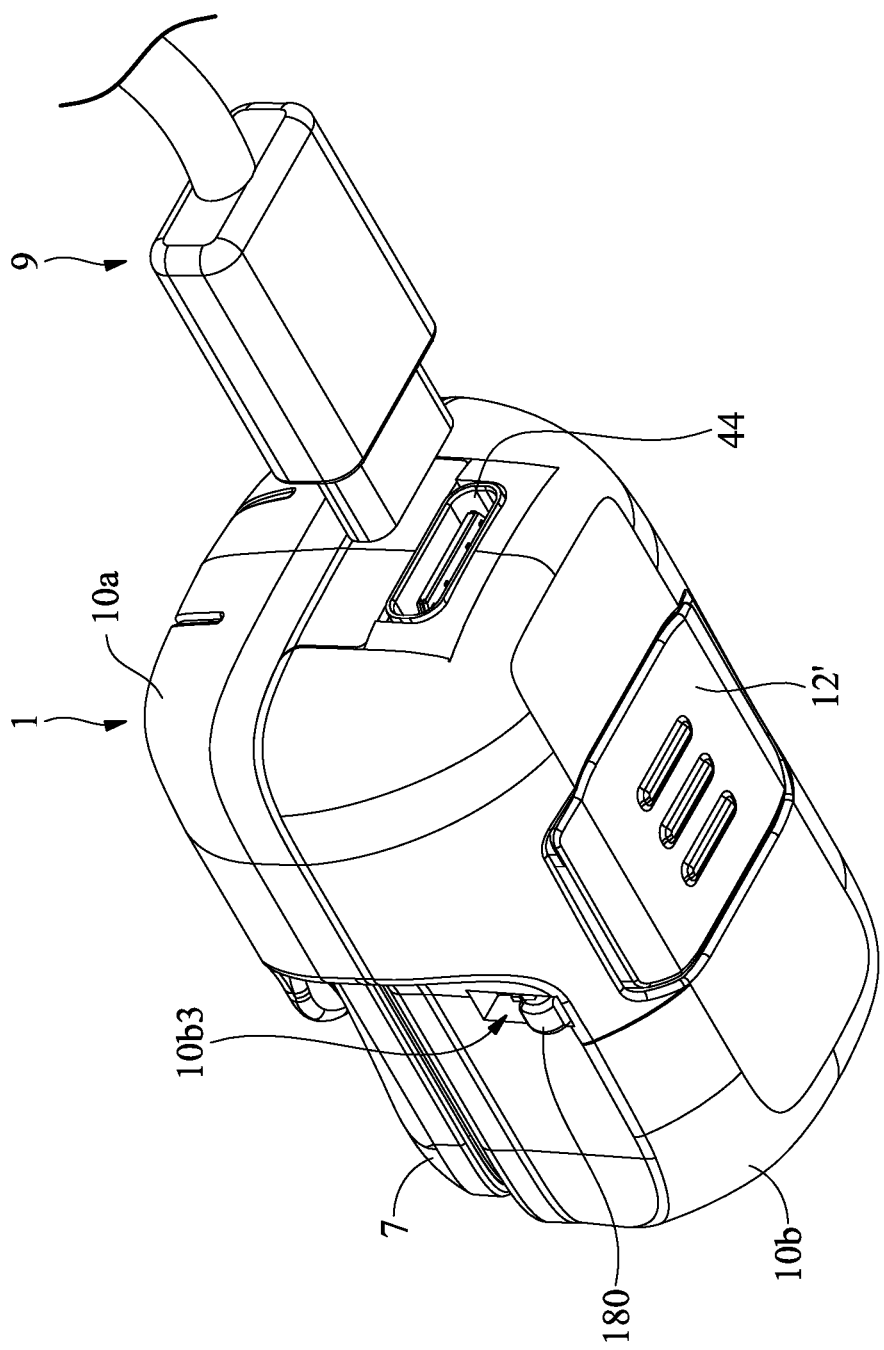
FIG. 16D shows a perspective view of the oblique front and bottom of the embodiment of FIGS. 16A-16B.

Please refer to FIGS. 16A to 16B, which are another embodiment of the charging device. Except the components and structures for the pressing button 12', the stopping end 52 of the first locking module 5 and the avoidance notch 52' are different from the previous figures, the rest of the components and structures are the same as those of the previous figures. The second connecting port 3'(or the charging seat 30) is in a way of moving up and down, and therefore the second connecting port 3' of this embodiment is connected to the pressing key 12' to drive the lifting or descending of the charging seat 30, which is usually a latch button structure, and the pressing member 12' can also be used as a part of the charging module 1, or can be a component that is operated independently. When the pressing key 12' is pressed once, the charging seat 30 will rise and stay stuck. When the pressing key 12' is pressed again, it will release the lock and return to the original position, i.e., the position when the pressing key 12' is not pressed. When the pressing key 12' is pressed, the second sliding element 302 of the charging seat 30 also slides up and down between the two guiding portions 150. Alternatively, the pressing key 12' can be positioned by the positioning button 180, which will be described in detail later. Please refer to FIG. 16A, which discloses that the transmitter 7 has not been inserted into the placing portion 13, so the actuating end 51 of the stopping module 5 also extends into the placing portion 13 (please refer to FIG. 1D) at this time. At this time, if the pressing key 12' is pressed into the body, the stopping end 52 will have a blocking effect on the blocked portion 43, thereby blocking the charging seat 30 from entering the placing portion 13. In another embodiment, the blocked portion 43 may also be formed on the charging seat 30 (not shown), or the locking slider 5 may be used in another embodiment as shown in FIG. 4D, Please refer to FIG. 16B, it discloses that the transmitter 7 has been inserted into the placing portion 13, so the actuating end 51 has been pressed down by the transmitter 7 at this time, and the first locking module 5 is rotated so that the avoidance notch 52' is aligned with the blocked portion 43. In other words, causing the stopping end 52 to move away from the upper part of the receiving part 43. At this time, if the pressing key 12' is pressed into the body, the blocked portion 43 can continue to rise by avoiding the notch 52', so that the charging seat 30 enters the placing part 13. When the pressing key 12' moves inward, the stopping end 52 enters the avoidance space 43' correspondingly to avoid interference with the pressing key 12'. In addition, as shown in FIGS. 16C and 16D, the pivotal frame 10a2 of the upper housing 10a and the pivotal frame 10b2 of the lower housing 10b clamp the pivotal portion 50 of the first locking module 5 in a rotatable manner. The lower housing 10b also has a push-resisting structure 10b3 to prevent the movement of the stopping end 52 so as to prevent the actuating end 51 from overextending into the placing portion 13. The charging device 1 further includes a second locking module 6, which is provided with a positioning portion 61 connected to an elastic unit 62 (as shown in FIGS. 5C, 6A), so that the positioning portion 61 can be extended out of the bearing surface 13' upwardly and downwardly to lock an installation position of the physiological signal transmitter 7.

Figure 16E:
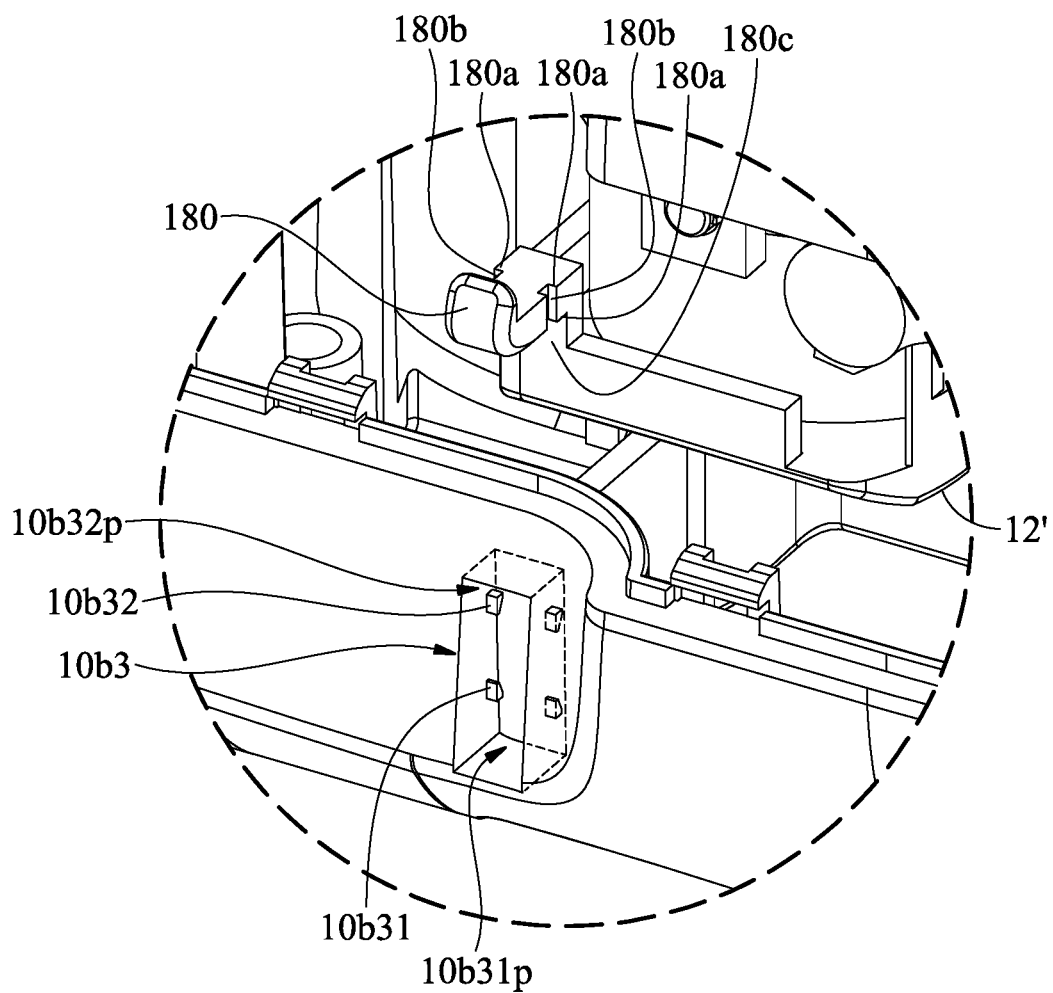
FIG. 16E shows a partial exploded perspective view of the embodiment of FIGS. 16A-16B.

Please refer to FIG. 16E, in order to fully observe the relationship between the positioning button 180 and the positioning groove 10b3, the positioning button 180 has been moved from the positioning groove 10b3 to the upper side. The positioning groove 10b3 has a first positioning block 10b31 and a second positioning block 10b32 arranged in pairs. Below the first positioning block 10b31 is the first state position 10b31p, i.e., the position when the pressing key 12' is at the lowest bottom. The positioning shoulder 180a can be blocked by the first positioning block 10b31, thereby preventing the positioning button 180 from moving upwards, i.e., blocking the pressing key 12' from moving upward. Above the second positioning block 10b32 is the second state position 10b32p, i.e., the position when the key 12' is at the top. The positioning shoulder 180a can be blocked by the second positioning block 10b32, thereby preventing the positioning button 180 from moving downward, i.e., blocking the pressing key 12' from moving downward. Furthermore, to move the pressing key 12' in the first state position 10b31p to the second state position 10b32p, it is only necessary to press the positioning button 180 inward to bend the elastic structure 180c and align the channel 180b to the first positioning block 10b31 and the second positioning block 10b32, i.e., operating the pressing key 12' or pushing the positioning button 180 upward. At this time, the positioning blocks (10b31, 10b32) pass through the passage 180b correspondingly without being blocked by the positioning shoulder 180a. In the same way, if you want to return the pressing key 12' to the lowest position, i.e., the position in the first state, then press the positioning button 180 inward to bend the elastic structure 180c, and align the channel 180b with the second positioning block 10b32 and the first positioning block, i.e., the positioning button 180 can be pushed down to drive the pressing key 12' back to the position of the first state. In addition, a reset element (not shown in the figure, it can be an elastic element or a magnetic element) can also be provided between the pressing button 12' or the second electrical connection port 3' and the upper housing 10a or the lower housing 10b, i.e., when the pressing key 12' is pressed so that the second electrical connecting port 3' is electrically connected to the first electrical connecting port 73, giving the reset element a bit of energy. The pressing key 12' relies on the positioning shoulder 180a to abut the second positioning block 10b32 to resist this position energy. Furthermore, when the positioning button 180 is pressed inward and the channel 180b is aligned with the second positioning block 10b32, the positioning shoulder 180a is no longer blocked by the second positioning block 10b32, and the position energy can be released. Thus, the pressing key 12' returns to the initial position.

Those skilled in the art can understand from the aforementioned FIG. 2 and various embodiments of the present invention that the charging module disclosed in the charging device 1 can independently cooperate with the transmitter 7, the charging modules can be used by combining with the operating module (such as the operating portion of FIG. 4A), the first locking module (such as the first locking portion 5 or the locking slider 5 in FIGS. 4B, 4D), or the second locking portion (such as the baffle 61 of FIG. 4C or 14A, which is driven by the second electrical connecting port 3' through the connecting 61' element (FIG. 7C)). Alternatively, the charging module 3 is used in conjunction with the operating module 4 and the first locking module 5 at the same time (such as the operating portion 40 and the first locking part 5 in FIG. 4B); or the charging module 3 is used with the operating module 4 and the second locking portion 6 at the same time (the operating portion 40 and the second locking portion 6 in FIG. 4C), or the charging module 3 is used in conjunction with the operating module 4, the first locking module 5, and the second locking portion 6 at the same time.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A charging device for a physiological signal transmitter, wherein the physiological signal transmitter is to receive and transmit a physiological signal from a subcutaneous tissue of a living body, and has a first electrical connecting port connecting to the charging device for charging, comprising:
   a transmitter placing seat including:
      a bearing surface disposing thereon the physiological signal transmitter; and
      a first opening aligning therewith the first electrical connecting port of the physiological signal transmitter;
   a charging module, including:
      a second electrical connecting port disposed in the first opening and moveable between a first position and a second position;
      a third electrical connecting port connectible to a power source; and
      a circuit assembly controlling a charging of the physiological signal transmitter, wherein the circuit assembly is electrically connected to the first electrical connecting port via the second electrical connecting port, and inputs therefrom a power from the power source by connecting to the third electrical connecting port; and a control module controlling an operation between the charging device and the physiological signal transmitter in a safe state and including:

an operating portion mechanically coupled with the second electrical connecting port, the operating portion is controlled to drive the second electrical connecting port to move between the first position and the second position, and is electrically separated or connected with the first electrical connecting port;

a locking portion mechanically coupled with the operating portion, and controlling the operating portion for driving the locking portion to protrude or retract along the bearing surface so as to determine whether the physiological signal transmitter is at a predetermined position to prohibit or allow an access of the physiological signal transmitter, wherein when the physiological signal transmitter is placed on the bearing surface, the operating portion is controlled to drive the second electrical connecting port to move from the first position to the second position to be electrically connected to the first electrical connecting port, and the locking portion is driven to protrude out of the bearing surface to position the physiological signal transmitter for locking the physiological signal transmitter from being removed, so as to prevent the first electrical connecting port and the second electrical connecting port from being damaged while electrically connecting because the physiological signal transmitter is taken out or placed, so as to achieve the safe state;

when the operating portion drives the second electrical connecting port to move from the second position to the first position to separate the first electrical connecting port from the second electrical connecting port, and the operating portion drives the locking portion retracts from the bearing surface for unlocking the physiological signal transmitter, so as to allow the first connection port and the second connection port to be separated before the removal of the physiological signal transmitter to achieve the safe state.

2. The charging device as claimed in claim 1, wherein the locking portion includes a first connecting end, and the operating portion further includes a second connecting end, the first connecting end and the second connecting end are releasably coupled, so that when the operating portion drives the second electrical connecting port to move toward the second position, the locking portion is driven to protrude out of the bearing surface.

3. The charging device as claimed in claim 1, wherein the operating portion further includes a first guiding element, and the second electrical connecting port further includes a second guiding element, wherein the first guiding element is coupled with the second guiding element for guiding the second electrical connecting port to electrically connect to the first electrical connecting port.

4. The charging device as claimed in claim 1, wherein the power source is an external power source, and the third electrical connecting port is a USB port or a power adapter.

5. The charging device as claimed in claim 1, wherein the physiological signal transmitter further includes a first matching portion, and the transmitter placing seat further includes a second matching portion, and when the first matching portion and the second matching portion combine with each other, the first connecting port and the first opening are correctly aligned.

6. The charging device as claimed in claim 1, wherein the transmitter placing seat further includes an indication area having a shape corresponding to the first matching portion on an outer surface of the physiological signal transmitter for visually indicating a placing direction of the physiological signal transmitter.

7. The charging device as claimed in claim 1, wherein the transmitter placing seat further includes a cover to form a slot for inserting the physiological signal transmitter laterally.

8. The charging device as claimed in claim 1, further comprising a housing, wherein the housing further includes a second opening, wherein the operating portion is coupled to the third connecting port, and when the operating portion guides the second electrical connecting port to move toward the second position, the third electrical connecting port is driven to protrude from the second opening.

9. A charging device for a physiological signal transmitter, wherein the physiological signal transmitter is to receive and transmit a physiological signal from a subcutaneous tissue of a living body, and has a first electrical connecting port, comprising:

a transmitter placing seat including:
a bearing surface disposing thereon the physiological signal transmitter; and
a first opening aligning therewith the first electrical connecting port;

a charging module, including:
a second electrical connecting port disposed in the first opening and moveable between a first position and a second position;
a third electrical connecting port connectible to a power source; and
a circuit assembly for performing charging and charging control on the physiological signal transmitter, the circuit assembly is electrically connected to the second electrical connecting port and the third electrical connecting port;

a control module for controlling a safety of electrical connection between the physiological signal transmitter and the charging module, including:
an operating portion coupled with the charging module for driving the second electrical connecting port to move and electrically connect with the first electrical connecting port;
a locking portion being extendable or retractable on the bearing surface for releasably positioning the physiological signal transmitter, wherein, when the physiological signal transmitter is placed on the bearing surface, the operating portion drives the second electrical connecting port to move from the first position to the second position to be electrically connected to the first electrical connecting port, and the locking portion is driven to protrude out of the bearing surface to locate the physiological signal transmitter.

10. The charging device as claimed in claim 9, wherein the operating portion drives the second electrical connecting port to move from the second position to the first position to separate from the first electrical connecting port, and the operating portion drives the locking portion to retract to the bearing surface for unlocking the physiological signal transmitter.

11. The charging device as claimed in claim 9, wherein the locking portion is coupled with the charging module, and the charging module links the locking portion to protrude out of the bearing surface.

12. The charging device as claimed in claim 9, wherein the locking portion is protrudes from the bearing surface for being raised or lowered, the locking portion is pressed downward when the physiological signal transmitter is placed on the bearing surface and passes the locking portion, and the locking portion is protruded from the bearing surface by an elastic restoring force when the physiological signal transmitter has completely left the second locking portion, so as to position the physiological signal transmitter.

13. The charging device as claimed in claim 9, wherein the locking portion is releasably coupled to the operating portion, when the operating portion drives the second electrical connecting port to drive the second electrical connecting port from the first position to the second position, the locking portion is driven to protrude out of the bearing the surface.

14. A charging device for a physiological signal transmitter, wherein the physiological signal transmitter is to receive and externally transmit a physiological signal from a subcutaneous tissue of a living body, and has a first electrical connecting port, comprising:
- a transmitter placing seat including:
  - a bearing surface disposing thereon the physiological signal transmitter; and
  - a first opening aligning therewith the first electrical connecting port of the physiological signal transmitter; and
- a charging module, including:
  - a second electrical connecting port disposed in the first opening and moveable between a first position and a second position;
  - a third electrical connecting port for connecting thereto a power source;
  - a circuit component for performing charging and charging control on the physiological signal transmitter, the circuit assembly is electrically connected to the second electrical connecting port and the third electrical connecting port;
- a locking module being extendable or retractable on the bearing surface for releasably positioning the physiological signal transmitter,
- wherein the charging module is driven to move the second electrical connecting port from the first position to the second position to be electrically connected to the first electrical connecting port, and the locking module is driven to protrude out of the bearing surface to fix the transmitter.

15. The charging device as claimed in claim 14, wherein when the charging module is driven to move the second electrical connecting port from the second position to the first position to separate the first electrical connecting port, the locking module is driven to retract to the bearing surface to unlock the physiological signal transmitter.

16. The charging device as claimed in claim 14, wherein the locking module is combined with the charging module, and the charging module is used for driving the locking module to protrude out of the bearing surface.

17. The charging device according to claim 14, wherein the charging module is provided with a driving end for an external force to drive the second electrical connecting port to protrude out of the opening to be electrically connected to the first electrical connecting port.

18. The charging device according to claim 16, wherein the locking portion is operable to be raised beyond and lowered beneath the bearing surface, during a placing procedure of the physiological signal transmitter, the locking portion is initially pressed down, and after the placing procedure is completed, the physiological signal transmitter completely passes over the locking portion, and the positioning module is protruded beyond the bearing surface by an elastic restoring force to confine the physiological transmitter.

* * * * *